United States Patent
Arhancet et al.

(10) Patent No.: US 10,457,660 B2
(45) Date of Patent: *Oct. 29, 2019

(54) HETEROATOM CONTAINING CYCLIC DIMERS

(71) Applicant: Novus International Inc., St. Charles, MO (US)

(72) Inventors: Graciela B. Arhancet, St. Charles, MO (US); Matthew Mahoney, St. Charles, MO (US); Xiaojun Wang, St. Charles, MO (US)

(73) Assignee: Novus International, Inc., St. Charles, MO (US)

(*) Notice: Subject to any disclaimer, the term of this patent is extended or adjusted under 35 U.S.C. 154(b) by 483 days.

This patent is subject to a terminal disclaimer.

(21) Appl. No.: 14/639,668

(22) Filed: Mar. 5, 2015

(65) Prior Publication Data
US 2015/0191444 A1 Jul. 9, 2015

Related U.S. Application Data

(62) Division of application No. 13/763,101, filed on Feb. 8, 2013, now Pat. No. 9,011,832.

(60) Provisional application No. 61/596,843, filed on Feb. 9, 2012, provisional application No. 61/597,444, filed on Feb. 10, 2012.

(51) Int. Cl.
| | |
|---|---|
| *C07D 319/12* | (2006.01) |
| *C08G 75/02* | (2016.01) |
| *C08G 67/00* | (2006.01) |
| *C08G 63/688* | (2006.01) |
| *C08G 63/85* | (2006.01) |
| *C08L 67/04* | (2006.01) |
| *C07D 265/33* | (2006.01) |
| *A23K 20/10* | (2016.01) |
| *A23K 50/10* | (2016.01) |
| *A23K 50/75* | (2016.01) |
| *C08L 67/00* | (2006.01) |

(52) U.S. Cl.
CPC ............ *C07D 319/12* (2013.01); *A23K 20/10* (2016.05); *A23K 50/10* (2016.05); *A23K 50/75* (2016.05); *C07D 265/33* (2013.01); *C08G 63/6882* (2013.01); *C08G 63/85* (2013.01); *C08G 67/00* (2013.01); *C08G 75/02* (2013.01); *C08L 67/00* (2013.01); *C08L 67/04* (2013.01)

(58) Field of Classification Search
CPC .................................................. C07D 319/12
See application file for complete search history.

(56) References Cited

U.S. PATENT DOCUMENTS

| | | |
|---|---|---|
| 2,787,595 A | 4/1957 | Webb |
| 3,272,860 A | 9/1966 | Nufer |
| 3,288,859 A | 12/1966 | Lyness |
| 3,290,254 A | 12/1966 | Anderson |
| 3,329,617 A | 7/1967 | von Doering |
| 3,761,518 A | 9/1973 | Haglid |
| 3,773,927 A | 11/1973 | Cummins |
| 3,960,152 A * | 6/1976 | Augurt ................. A61L 17/105 606/230 |
| 4,033,938 A | 7/1977 | Augurt |
| 4,095,029 A | 6/1978 | Fields |
| 4,235,942 A | 11/1980 | Heller et al. |
| 4,310,690 A | 1/1982 | Cummins |
| 4,317,779 A | 3/1982 | Crawford |
| 4,353,942 A | 10/1982 | Carey |
| 4,388,327 A | 6/1983 | Cummins |
| 4,395,363 A | 7/1983 | Crawford |
| 4,399,665 A | 8/1983 | Evans et al. |
| 4,419,198 A | 12/1983 | Breda |
| 4,435,527 A | 3/1984 | Cuscurida |
| 4,451,486 A | 5/1984 | Baker |
| 4,524,077 A | 6/1985 | Ruest |
| 4,579,962 A | 4/1986 | Takano |
| 4,720,484 A | 1/1988 | Vincent |
| 4,727,163 A | 2/1988 | Bellis |
| 4,777,289 A | 10/1988 | Ruest |
| 4,835,293 A | 5/1989 | Bhatia |
| 4,855,495 A | 8/1989 | Takano |
| 4,883,911 A | 11/1989 | Ruest |
| 5,274,073 A | 12/1993 | Gruber |
| 5,294,605 A | 3/1994 | Houghten |
| 5,310,599 A | 5/1994 | Ford |
| 5,326,887 A | 7/1994 | Di Cosirno |
| 5,357,001 A | 10/1994 | Grosse-Bley |
| 2,703,316 A | 3/1995 | Schneider |

(Continued)

FOREIGN PATENT DOCUMENTS

| | | |
|---|---|---|
| CN | 104754956 A | 7/2015 |
| EP | 0079164 A1 | 5/1983 |

(Continued)

OTHER PUBLICATIONS

Huthmacher, K. "Polyhydroxymethionine." Biopolymers. (2003), vol. 9, pp. 81-87.*
Gerhardt, W.W., et al. "Functional Lactide Monomers: Methodology and Polymerization." Biomacromolecules. (2006), vol. 7, pp. 1735-1742, referenced in IDS of Sep. 21, 2015.*
PubChem. "Stannous Octoate." © 2005. Available from: <https://pubchem.ncbi.nlm.nih.gov/compound/stannous_octoate >.*
"Hydroxyl Protecting Groups Stability." (c) Feb. 9, 2010. Available from: <https://web.archive.org/web/20100209010543/http://www.organic-chemistry.org/protectivegroups/hydroxyl.shtm >.*

(Continued)

*Primary Examiner* — Noble E Jarrell
*Assistant Examiner* — John S Kenyon
(74) *Attorney, Agent, or Firm* — Polsinelli PC

(57) ABSTRACT

The present invention provides cyclic dimers of alpha acids and polymers derived therefrom. Also provided are processes for preparing and methods of using the cyclic dimers and the polymers derived from the cyclic dimers.

31 Claims, 10 Drawing Sheets
(1 of 10 Drawing Sheet(s) Filed in Color)

(56) References Cited

U.S. PATENT DOCUMENTS

| | | |
|---|---|---|
| 5,503,852 A | 4/1996 | Steiner |
| 5,602,229 A | 2/1997 | Malabrba |
| 6,008,261 A | 12/1999 | Genova |
| 6,008,409 A | 12/1999 | Hasselberg |
| 6,172,067 B1 | 1/2001 | Ito |
| 6,180,643 B1 | 1/2001 | Zablocki |
| 6,518,243 B1 | 2/2003 | Kahne |
| 6,727,285 B1 | 4/2004 | Haik, Jr. |
| 6,939,693 B2 | 9/2005 | Lorbert |
| RE39,403 E | 11/2006 | Robert |
| 7,250,433 B2 | 7/2007 | Barta |
| 7,381,416 B2 | 6/2008 | Erdelmeir |
| 7,714,077 B2 | 5/2010 | Tanaka |
| 7,989,532 B2 | 8/2011 | Li |
| 9,011,832 B2 | 4/2015 | Arhancet |
| 9,284,294 B2 | 3/2016 | Arhancet |
| 9,410,036 B2 | 8/2016 | Arhancet |
| 9,447,068 B2 | 9/2016 | Arhancet |
| 9,452,143 B2 | 9/2016 | Smith |
| 2003/0143366 A1 | 7/2003 | Foley |
| 2003/0143661 A1 | 7/2003 | Lorbert |
| 2007/0053866 A1 | 3/2007 | Abou-Nemeh |
| 2007/0231377 A1 | 10/2007 | Abou-Nemeh |
| 2008/0019860 A1 | 1/2008 | Abou-Nemeh |
| 2008/0241223 A1 | 10/2008 | Nivaggioli |
| 2009/0200511 A1 | 8/2009 | Allen |
| 2010/0048586 A1 | 2/2010 | Deigin |
| 2010/0098801 A1 * | 4/2010 | Kobler .............. A23K 1/1634 426/2 |
| 2011/0021461 A1 | 1/2011 | Vazquez-Anon |
| 2011/0070188 A1 | 3/2011 | Flowers |
| 2011/0295006 A1 | 12/2011 | Kobler |
| 2012/0035341 A1 * | 2/2012 | Diehl ................. C07D 319/12 528/223 |
| 2012/0128616 A1 | 5/2012 | Voisin |
| 2013/0209391 A1 | 8/2013 | Arhancet |

FOREIGN PATENT DOCUMENTS

| | | |
|---|---|---|
| EP | 2812313 | 8/2013 |
| EP | 2812372 | 8/2013 |
| EP | 2871973 | 5/2015 |
| JP | S50-101367 | 8/1975 |
| JP | H7-126358 | 5/1995 |
| JP | H10-114769 | 5/1998 |
| JP | 11-029628 | 2/1999 |
| JP | 2004001190 A | 1/2004 |
| JP | 2005232046 A | 2/2005 |
| JP | 2005232047 A | 9/2005 |
| JP | 2008239601 A | 10/2008 |
| JP | 2012-001634 | 1/2012 |
| JP | 2015508076 A | 3/2015 |
| WO | 9215547 A1 | 9/1992 |
| WO | 9509142 A1 | 4/1995 |
| WO | 9636314 A2 | 11/1996 |
| WO | 1998032735 A1 | 7/1998 |
| WO | 9851260 A2 | 11/1998 |
| WO | 1999004647 A1 | 2/1999 |
| WO | 0142333 A2 | 6/2001 |
| WO | 0149273 A2 | 7/2001 |
| WO | 03010157 A1 | 2/2003 |
| WO | 2003082836 A1 | 10/2003 |
| WO | 2005077882 | 8/2005 |
| WO | 2005077882 A1 | 8/2005 |
| WO | 2009088879 A1 | 7/2009 |
| WO | 2009127009 A1 | 10/2009 |
| WO | 2010012712 A1 | 2/2010 |
| WO | 2010048586 A1 | 4/2010 |
| WO | 2010100390 A1 | 9/2010 |
| WO | WO-2010100390 A1 * | 9/2010 ........... C07D 319/12 |
| WO | 2011084466 A1 | 7/2011 |
| WO | 2011084620 A2 | 7/2011 |
| WO | 2011028007 A2 | 10/2011 |
| WO | 2013119955 A1 | 8/2013 |
| WO | 2013119959 A1 | 8/2013 |
| WO | 2014011857 A1 | 1/2014 |

OTHER PUBLICATIONS

"Protective Groups in Organic Synthesis." EBSCO Publishing. (c) 1999.*

"Polydispersity Index: How Accurately Does It Measure the Breadth of the Molecular Weight Distribution?" Chem. Mater. (2005), vol. 17, p. 926.*

Albertsson, A-C., et al. "Recent Developments in Ring Opening Polymerization of Lactones for Biomedical Applications." Biomacromolecules (2003), vol. 4, pp. 1466-1486. (Year: 2003).*

Leemhuis, M., et al. "Functionalized Poly(alpha-hydroxy acid)s via Ring-Opening Polymerization: Toward Hydrophilic Polyesters with Pendant Hydroxyl Groups." Macromolecules (2006), vol. 39, pp. 3500-3508. (Year: 2006).*

Shasteen, C., et al. "Controlling Degradation Rate of Poly(lactic acid) for Its Biomedical Applications." Biomed Eng Lett (2011), vol. 1, pp. 163-167. (Year: 2011).*

Huthmacher, K. "Polyhydroxymethionine." Biopolymers. (2003), vol. 9, pp. 81-87. (Year: 2003).*

"Ring-Opening Polymerization of 3(S)-[(Benzyloxycarbonyl)methyl]-1,4-dioxane-2,5-dione: A New Route to a Poly($\alpha$-hydroxy acid) with Pendant Carboxyl Groups." Macromolecules. (1988), vol. 21, pp. 3338-3340. (Year: 1988).*

Leemhuis, A versatile Route to Functionalized Dilactones as Monomers for the Synthesis of Poly(a-Hydroxy) Acids, Eur. J. Org. chem, 2003, pp. 3344-3349.

United States Patent and Trademark Office; U.S. Appl. No. 14/937,416; Notice of Allowance dated Dec. 16, 2015.

European Patent Office; PCT/US2013/050051, Extended European Search Report dated Nov. 12, 2015.

Bentley et al. "Action of Nitrogen on certain Proteins II. Synthesis of Methionine Sulphoximine and other Sulphoximines," 1950, 265-272.

Brenner et al. "Isolation of enzymatically manufactured L-methionyl-L-methionine and L-methionyl-L-methionyl-L-methionine; a comparison with synthetic products" Helv. Chim. Acta 1951; 34;2085-2096 (German language document, no translation available).

Bruyer, "Oligomers In Equilibrium in DL-2-Hydroxy-4-Methylthio Butanoic Acid (HMB) Solutions." 1987, dated Jan. 26, 14 pgs.

Bueno et al. "1,4-Dioxane-2,5-dione-type monomers derived from L-ascorbic and D-isoascorbic acids Synthesis and Polymerisation," Carbohydrate Research (2009), 344(15). 2100-2104.

Chen et al. "ProSAR: A new Methodology for Combinatorial Library Design" J. Chem. Inf. Model 2009, 49, 603-614.

Cohen-Arazi, et al. "Preparation of New [alpha]-hydroxy Acids Derived from Amino Acids and Their Corresponding Polyesters," Oct. 28, 2008 Macromolecules, vol. 41, No. 20, 7259-7263, supplemental data.

Dechy-Cabaret, "Controlled Ring-Opening Polymerization of Lactide and Glycolide" Chem. Rev. 2004 104 (12), 6147-6176.

Franz et al. "Synthesis of Functional Polydepsipeptides via Direct Ring-Opening Polymerization and Post-Polymerization Modification" Macromolecular Journals; Macromol. Chem. Phys. 2010, 211, 809-820.

Hutamacher, "Polyhydroxymethionine" Biopolymers, vol. 9, pp. 81-87, 2003 Wiley-VCH.

Jiang et al. "Clickable" Polyglycolides: Tunable Synthons for Thermoresponsive, Degradable Polymers; Macromolecules 2008, 41, 1937-1944.

Jing et al. "Cyclohexyl-substituted polyglycolides with high glass transition temperatures" Macromolecules (2007), 40 (26), 9304-9312.

Jost et al. "Papain catalyzed oligomerization of $\alpha$-amino acids. Synthesis and characterization of water-insoluble oligomers of L-methionine" Helv. Chim. Acta. 1980;63:375-384.

Kasai et al. "Correlation between molecular weight distribution of oligo-L-methionine prepared by papain-catalyzed polymerization and its supplementary in a low protein diet." 1992 Biosci., Biotechnol., Biochem. 56: 1884-1885.

(56) References Cited

OTHER PUBLICATIONS

Kolitz et al. "Biodegradable Polyesters Derived from Amino Acid," Macromolecules Article 2009, 42, 4520-4530.
Lee et al. "Papain catalyzed polymerization of L-α-amino acid methyl esters with hydrophobic side chains," Chem. Express 1990; 5:741-744.
Leemhuis et al. "Synthesis and characterization of allyl functionalized poly(α-hydroxy)acids and their further dihydroxylation and epoxidation, "European Polymer Journal (2008), 44(2), 308-317.
Nguyen et al. "Polydepsipeptides: Investigation of Secondary Structure" PMSE Preprints Fall 2009, vol. 101, 16-20, vol. 2 of 2, 798-799, American Chemical Society Division of Polymeric Materials: Science and Engineering Fall 2009.
Noga et al. "Synthesis and Modification of functional Poly(lactide) Copolymers: Toward Biofunctional Materials" Biomacromolecules 2008, 9, 2056-2062.
Ouchi et al. "Design of Lactide-Based Copolymers for Biomaterials," Polymer Preprints Fall 2002, 43 (2) 648-649.
Ouchi et al. "Preparation of Poly(L-lactide)—Based Microspheres Having a Cationic or Anionic Surface Using Biodegradable Surfactants" Published by the American Chemical Society, Sep./Oct. 2002; vol. 3 No. 5, 885-888.
Ouchi et al. "Synthesis of a block copolymer of L-lactide and depsipetide with pendant thiol groups," Designed Monomers and Polymers, vol. 3, No. 3. pp. 279-287 (2000).
Pounder et al. "Synthesis and Organocatalytic Ring-Opening Polymerization of Cyclic Esters Derived from L-Malic Acid," Biomacromolecules (2010), 11, 1930-1939.
Qi et al. "Cytotoxicity and Cellular Uptake Evaluation of Mitoxantrone-Loaded Poly(lactic acid-co-lysine) Arginine-Glycine-Aspartic Acid Nanoparticles," Journal of Applied Science 2010, vol. 119, 1011-1015.
Rajesh et al. "Enzymatic Synthesis and Characterization of L-Methionine and 2-Hydroxy-4(methylthio)butanoic Acid (HMB) Co-oligomers," 2003 J. Agric. Food Chem. 51, 2461-2467.
Reynal, "Omasal Flow of Soluble Proteins, Peptides, and Free Amino Acids in Dairy Cows Fed Diets Supplemented with Proteins of Varying Ruminal Degradabilities" (2007) J. Dairy Sci. 90: 1887-1903.
Ristic et al. "The Properties of Poly(L-Lactide) Prepared by Different Synthesis Procedure," Journal of Polymers and the Environment (2011), 19(2), 419-430.
Rubenshtein et al. "Facile Procedure for Generating Side Chain Functionalized Poly(r-hydroxyacid) Copolymers from Aldehydes via a Versatile Passerini-Type Condensation," Org. Lett, 2010, vol. 12, No. 15, pp. 3560-3563.
Yan et al. "Synthesis and RGD peptide of Poly {(lactic acid)-co-[(glycolic axid)-alt-L-lysine)]}" 2008, e-Polymers, No. 028, 12 pgs.
Williams et al. "Synthesis of functionalized biodegradable polyesters" Tutorial Review 2007, vol. 36, 1573-1580.
Yin et al. "Preparation and Characterization of Substituted Polylactides" Macromolecules (Nov. 16, 1999), 32(23), 7711-7718.
Yin et al. "Synthesis and characterization of substituted polylactides," Polymer Preprints (1998). 39(2), 158-159, American Chemical Society.
Yu et al. "Synthesis of 3-benzyl-glyceric acid: a key intermediate of a novel cyclic ester monomer" Chinese Journal of Polymer Science (2002), 20(2), 177-180.
International Search Report and Written Opinion for PCT/US2013/025355 dated Apr. 22, 2013.
International Search Report and Written Opinion for PCT/US2013/025351 dated Apr. 22, 2013.
International Search Report and Written Opinion for PCT/US2013/50051 dated Dec. 6, 2013.
Balg et al., "Inhibition of Helicobacter pylori Aminoacyl-tRNA Amidotransferase by Puromycin Analogues," J. Am. Chem. Soc., 2008, pp. 3264-3265. vol. 130, No. 11.

Clint et al., "Thermodynamics of Micellization of Homologous Series of n-Alkyl Methyl Sulphoxides and n-Alkyl (dimethyl)phosphine Oxides," J. Chem. Soc., Faraday Transactions 1, 1975, pp. 946-954, vol. 71.
Evans et al. "Nanomolar-Affinity, Non-Peptide Oxytocin Receptor Antagonists," Journal of Medicinal Chemistry, 1993, pp. 3993-4005, vol. 36, No. 25.
Hennaux et al., "Novel nonionic polymerisable surfactants based on sulfoxides. 1. Monomer synthesis and general surfactant behaviour," Colloid Polym. Sci., 2001, pp. 1149-1159, vol. 379.
Hennaux et al., "Novel nonionic surfactants based on sulfoxides. 2. Homo- and copolymers," Colloid Polym. Sci., 2003. pp. 807-814, vol. 281.
Ignasiak et al., "Characterization by mass spectrometry and IRMPD spectroscopy of the sulfoxide group in oxidized methionine and related compounds," Chemical Physics Letters, 2011, pp. 29-36, vol. 502.
International Search Report and Written Opinion for PCT/US2012/072016 dated Mar. 5, 2013.
John, "Synthese and Modification of New Biodegradable Copolymers: Serine/Glycolic Acid Based Copolymers, New Biodegradable Copolymers," 1997, pp. 1901-1907.
Komori et al., "Structure Activity Relationships of Synthetic Antibiotic Analogues of Chryscandin," The Journal of Antibiotics, 1985, pp. 1182-1203, vol. 38, No. 9.
Li et al., "High Throughput Synthesis of Peptide α-Thioesters Through the Use of "Volatilizable" Support," Journal of Combinatorial Chemistry. 2008, pp. 613-616, vol. 10, No. 5 (and Supporting Information).
Roenne et al., "Lipase-Catalyzed Esterification of Lactic Acid with Straight-Chain Alcohols," J. American Oil Chemists' Society, 2005, pp. 881-885, vol. 82, No. 12.
Patent Examination Report No. 1 dated May 23, 2016 from related Australian Application No. 2013216832, 6 pgs.
Notice of grant for patent dated Jan. 5, 2017 from related Australian Application No. 2013216832, 1 pg.
Examination Report dated May 4, 2016 from related EP Application 13746592.8, 4 pgs.
Examination Report dated Nov. 30, 2016 from related EP Application 13746592.8, 4 pgs.
Office Action dated Aug. 23, 2016 from related Japanese Application 2014-556731, 7 pgs.
Examination Report dated Sep. 6, 2016 from related Australian Application 2013216828, 2 pgs.
Notice of Acceptance dated Dec. 22, 2016 from related Australian Application 2013216828, 8 pgs.
Examination Report dated Oct. 12, 2016 from related EP Application 13746152.1, 4 pgs.
Office Action dated Oct. 4, 2016 from related Japanese Application 2014-556729, 7 pgs.
Examination Report dated Jan. 27, 2016 from related Australian Application 2013290122, 9 pgs.
Notice of Acceptance dated Aug. 1, 2016 from related Australian Application 2013290122, 7 pgs.
Office Action dated May 25, 2016 from related Chinese Application 201380047090.3, 10 pgs.
Extended Search Report dated Nov. 25, 2015 from related EP Application 13816624.4, 8 pgs.
Office Action dated Jul. 5, 2016 from related U.S. Appl. No. 15/133,448, 7 pgs.
Notice of Allowance dated Jan. 23, 2017 from related U.S. Appl. No. 15/133,448, 7 pgs.
Sato et al., "Oxidation of sulfides to sulfoxides and sulfones with 30% hydrogen peroxide under organic solvent-and halogen-free conditions," Tetrahedron, 2001, pp. 2469-2476. vol. 57.
Third-Party Submission Under 37 CFR 1.290 from related U.S. Appl. No. 13/763,135 dated Apr. 10, 2014 (9 pgs.).
Yoshiizumi et al., "Studies on Scavenger Receptor Inhibitors. Part 1: Synthesis and Structure—Activity Relationships of Novel Derivatives of Sulfatides," Bioorganic & Medicinal Chemistry, 2002, pp. 2445-2460, vol. 10.
United States Patent and Trademark Office; U.S. Appl. No. 14/413,540; Non-Final Rejection dated Oct. 10, 2015.

(56) References Cited

OTHER PUBLICATIONS

Weerden et al., "DL-Methionine and DL-Methionine Hydroxy Analogue Free Acid in Broiler Diets," Institute for Animal Nutrition Research, 1983, pp. 1269-1277.
Koban et al.; J. Agric. Food Chem.; (1984) 32, pp. 393-396.
USDA National Nutrient Database for methionine; 81-pages; downloaded Feb. 11, 2015.
United States Patent and Trademark Office; U.S. Appl. No. 13/763,135; Office Action dated Feb. 18, 2015.
United States Patent and Trademark Office; U.S. Appl. No. 13/763,101; Office Action dated Jun. 24, 2014.
United States Patent and Trademark Office; U.S. Appl. No. 13/763,101; Office Action dated Nov. 22, 2013.
United States Patent and Trademark Office; U.S. Appl. No. 13/763,101; Notice of Allowance dated Dec. 8, 2014.
European Patent Office; PCT/US2013/025351; Extended European Search Report dated Jan. 9, 2015.
European Patent Office; PCT/US2013/025355; Extended European Search Report dated Aug. 24, 2015.
Weerden E J Van et al: "Utilization of the Polymers of Methionine Hydroxy Analog Free Acid (MHA-FA) in Broiler Chicks," Archiv Fuer Gefluegelkunde, Verlag Eugen Ulmer GMBH, DE, vol. 56, No. 2, Jan. 1, 1992, pp. 63-68.
Yoshio Hayashi et al: "Analysis of Amide Bond Formation with an [alpha]-Hydroxy-[beta]-amino Acid Derivative, 3-Amino-2-hydroxy-4-phenylbutanoic Acid, as an Acyl Component: Byproduction of Homobislactone," The Journal of Organic Chemistry, vol. 66, No. 16, Aug. 1, 2001, pp. 5537-5544.
In't Veld P J A et al: "Synthesis of Biodegradable Polyesteramides with Pendant Functional Groups," Makromolekulare Chemie, Macromolecular Chemistry and Physics, Wiley—VCH Verlag GMBH & Co. KGAA, vol. 193, No. 11, Nov. 1, 1992, pp. 2713-2730.
Gu S Y et al., "Synthesis and evaluation of a biodegradable material with cell recognition motives," Carbohydrate Polymers, Applied Science Publishers, Ltd.; Barking, GB, vol. 74, No. 3, Nov. 4, 2008, pp. 572-578.
Hui Yu et al., "Synthesis and characterization of arginine-glycerine-aspartic peptides conjugated poly(lactic acid-co-l-lysine) diblock copolymer," Journal of Materials Science: Materials in Medicine, Kluwer Academic Publishers, B0, vol. 19, No. 3, Aug. 20, 2007, pp. 1275-1281.
Gerhardt W W et al., "Functional lactide monomers," Biomacromolecules, American Chemical Society, US, vol. 7, No. 6. Jan. 1, 2006. pp. 1735-1742.
Andrew D. Abell et al., "Synthesis of a [1,4]dioxane-2,5-dione based-peptidomimetric scaffold," Arkivoc, vol. 2006, No. 3, Jan. 1, 2006, pp. 72-76.
Maryanoff B E et al., "Macrocyclic Peptide inhibitors of serine proteases. Convergent total synthesis of cyclotheonamides a and b via late-stage primary amine intermediate. Study of Thrombin Inhibition Under diverse conditions," Journal of the American Chemical Society. US, vol. 117, No. 4, Jan. 1, 1995, pp. 1225-1239.
Office action dated May 29, 2017 from related EP Application No. 13 746 592.8, 3 pp.
Office action dated Sep. 19, 2017 from related EP Application No. 13 746 152.1, 4 pp.
Office action dated Jun. 16, 2017 from related EP Application No. 13 816 624.4, 6 pp.
English translation of Office action dated Feb. 17, 2017 from related CN Application No. 201380047090.3, 6 pp.
Office action dated Feb. 6, 2018 from related U.S. Appl. No. 15/393,360, 7 pp.
Office action dated Jul. 31, 2017 from related AU Application No. 2016247230, 2 pp.
Office action dated Jan. 29, 2018 from related AU Application No. 2016277562, 3 pp.
Office action dated Aug. 21, 2017 from related AU Application No. 2017202307, 2 pp.
English translation of Office action dated Feb. 20, 2018 from related JP Application No. 2017-085214, 6 pp.
English translation of Office action dated Mar. 4, 2018 from related MX Application No. MX/a/2015/000395, 2 pp.
Office action dated Sep. 28, 2018 from related U.S. Appl. No. 15/393,360, 14 pp.
Jamshidian, Poly-Lactic Acid: Production, Applications, Nanocomposites, and Release Studies, Comprehensive Reviews in Food Science and Food Safety, 2010, vol. 9, 552-571.
Dorwald, Side Reactions in Organic Synthesis a Guide to Successful Synthesis Design, WILEY-VCH Verlag GmbH & Co. KGaA, Weinheim, 2005, p. IX.

* cited by examiner

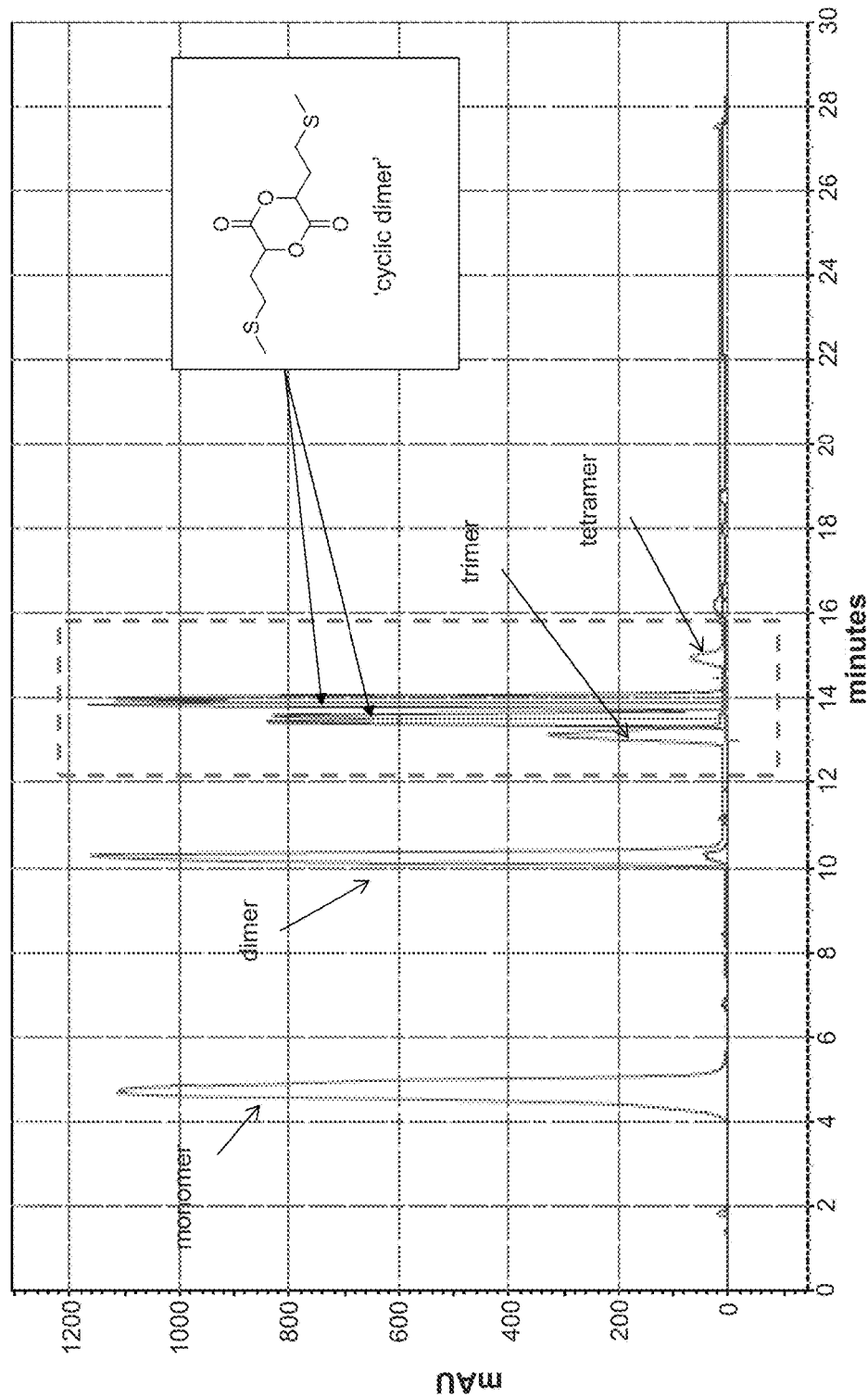

HETEROATOM CONTAINING CYCLIC DIMERS

CROSS-REFERENCE TO RELATED APPLICATIONS

This application is a divisional of U.S. application Ser. No. 13/763,101, which claims priority to U.S. provisional application No. 61/596,843, filed Feb. 9, 2012, and U.S. provisional application No. 61/597,444, filed Feb. 10, 2012, each of which is hereby incorporated by reference in its entirety.

FIELD OF THE INVENTION

The invention relates to cyclic dimers of alpha acids and polymers derived therefrom, processes for preparing and methods of using cyclic dimers and polymers derived therefrom.

BACKGROUND OF THE INVENTION

Alpha acids are important molecules for a variety of purposes including as industrial chemicals, feed additives, therapeutics, and various other uses. Alpha acids include, for example, amino acids and alpha hydroxy acids. When two alpha acids react, they can form linear or cyclic dimers. When alpha acids react to form cyclic dimers the acid moiety is no longer free, and thus the cyclic dimers can have different physical properties such as reactivity, stability, and solubility, that can be advantageous for certain applications.

For example, cyclic dimers can be used as compounds capable of releasing alpha acids. Cyclic dimers of alpha acids also may provide important routes for synthesizing polymers and copolymers of alpha acids. For example, lactic acid cyclic dimers, also called lactides, provide an important route to polylactic acid, an important polymer which has attracted significant interest due to its properties of being biocompatible and biodegradable, and for its suitability for uses in the biomedical and industrial fields. Formation of lactide from lactic acid is complicated by competing oligomerization reactions. Most processes developed for producing lactide compounds involved treatment at high temperatures under a vacuum. For example, U.S. Pat. No. 5,274,073 describes production of lactide by evaporating water from lactic acid to give an oligomer, and then mixing the oligomer with a depolymerization catalyst followed by thermal cracking to produce the lactide as a vapor.

Unlike lactide, cyclic dimers of alpha acids with heteroatom side chain moieties have not been synthesized using the thermal cracking process. Heteroatom substituted cyclic dimers are desirable compounds because they can provide important functionalities for the numerous applications of the cyclic compounds. For example, substituted cyclic dimers may provide routes to functionalized and structurally diverse (i.e. branched, star, block) polymers and copolymers, which may have different or enhanced properties over polylactic acid. Other methods for synthesizing cyclic dimers have also failed for heteroatom containing alpha acids. A theoretical route to forming the cyclic compounds from reaction of the halogen substituted monomers give poor yields because the halogenated monomer is unstable. Thus, routes to functionalized cyclic dimers of alpha acids remain a synthetic challenge.

Thus, there is a need for heteroatom containing cyclic dimers as well as processes for making them.

SUMMARY OF THE INVENTION

The present invention relates to cyclic dimers of alpha acids, polymers prepared from cyclic dimers of alpha acids, methods for preparing cyclic dimers and polymers prepared therefrom, and uses of the cyclic dimers and polymers.

A first aspect of the invention encompasses a compound comprising Formula (I):

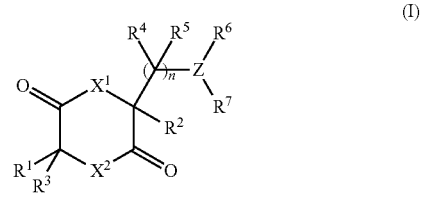

wherein, $X^1$ and $X^2$ are chosen from nitrogen and oxygen, provided that both $X^1$ and $X^2$ are not nitrogen;

$R^1$, $R^2$, $R^3$, $R^4$, and $R^5$ are independently chosen from hydrogen, hydrocarbyl, and substituted hydrocarbyl;

$R^6$ is chosen from hydrogen, hydrocarbyl, and substituted hydrocarbyl;

$R^7$ is optionally present, when present it is chosen from hydrogen, hydrocarbyl, and substituted hydrocarbyl;

Z is chosen from nitrogen, sulfur, sulfone, sulfoxide, and selenium; and n is an integer ≥ 1;

provided that when Z is sulfur and n is 1, then $R^1$ and $R^3$ are other than hydrogen; and when Z is nitrogen, n is from 2 to 4, and $R^3$ is hydrogen, then $R^1$ is other than hydrogen or methyl.

Another aspect of the present disclosure provides a process for preparing a compound comprising Formula (IX). The process comprises (a) contacting a compound comprising Formula (VI) with a compound comprising Formula (VII) or a compound comprising Formula (VIII) and an acid catalyst and (b) dehydrating the resulting reaction mixture to form the compound comprising Formula (IX), the compounds comprising Formula (IX), (VI), (VII), and (VIII):

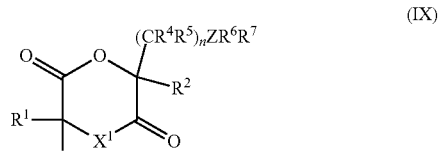

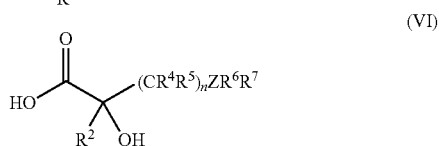

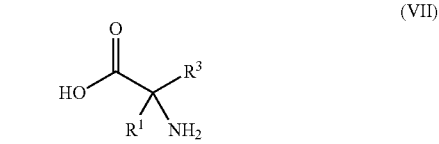

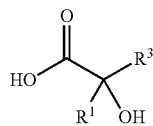

(VIII)

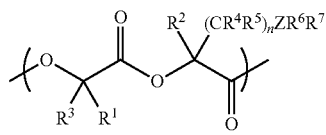

(XX)

wherein:
R¹, R², R³, R⁴, and R⁵ are independently chosen from hydrogen, hydrocarbyl, and substituted hydrocarbyl;
R⁶ is chosen from hydrogen, hydrocarbyl, and substituted hydrocarbyl;
R⁷ is optionally present, when present it is chosen from hydrogen, hydrocarbyl, and substituted hydrocarbyl;
Z is chosen from nitrogen, sulfur, sulfone, sulfoxide, and selenium; and
n is an integer≥1.

Still another aspect of the present disclosure provides a polymer comprising Formula (XXI):

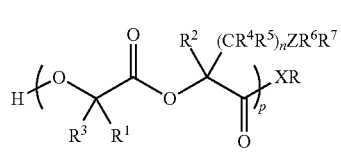

(XXI)

wherein:
R is chosen from hydrogen, hydrocarbyl, and substituted hydrocarbyl;
X is chosen from oxygen and nitrogen; and
p is an integer greater than 1.

An additional aspect of the disclosure encompasses a process for forming a polymer. The process comprises contacting a plurality of compounds comprising Formula (II):

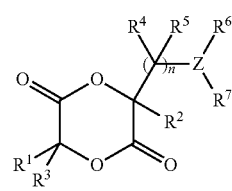

(II)

with a catalyst to form the polymer comprising a repeat unit comprising Formula (XX):

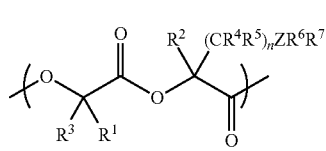

(XX)

wherein:
R¹, R², R³, R⁴, and R⁵ are independently chosen from hydrogen, hydrocarbyl, and substituted hydrocarbyl;
R⁶ is chosen from hydrogen, hydrocarbyl, and substituted hydrocarbyl;
R⁷ is optionally present, when present it is chosen from hydrogen, hydrocarbyl, and substituted hydrocarbyl;

wherein,
X¹ is chosen from oxygen and nitrogen,
R¹, R², R³, R⁴, and R⁵ are independently chosen from hydrogen, hydrocarbyl, and substituted hydrocarbyl;
R⁶ is chosen from hydrogen, hydrocarbyl, and substituted hydrocarbyl;
R⁷ is optionally present, when present it is chosen from hydrogen, hydrocarbyl, and substituted hydrocarbyl;
Z is chosen from nitrogen, sulfur, sulfone, sulfoxide, and selenium; and
n is an integer≥1.

A further aspect of the disclosure encompasses another method for preparing a compound comprising Formula (IX). The process comprises (a) heating a compound comprising Formula (VI) with a compound comprising Formula (VII) or a compound comprising Formula (VIII) to form a polymer and (b) heating the polymer at a temperature of about 200° C. and a pressure of less ban about 1 Torr to form the compound comprising Formula (IX), the compounds comprising Formula (IX), (VI), (VII), and (VIII):

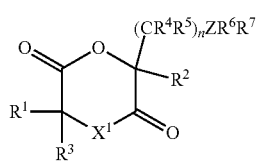

(IX)

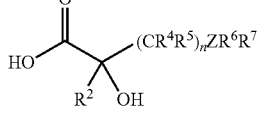

(VI)

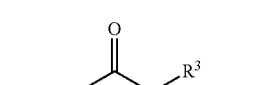

(VII)

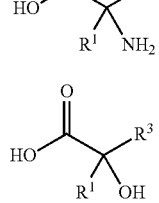

(VIII)

wherein,
X¹ is chosen from oxygen and nitrogen,
R¹, R², R³, R⁴, and R⁵ are independently chosen from hydrogen, hydrocarbyl, and substituted hydrocarbyl;
R⁶ is chosen from hydrogen, hydrocarbyl, and substituted hydrocarbyl;
R⁷ is optionally present, when present it is chosen from hydrogen, hydrocarbyl, and substituted hydrocarbyl;
Z is chosen from nitrogen, sulfur, sulfone, sulfoxide, and selenium; and
n is an integer≥1.

Yet another aspect provides a polymer comprising a repeat unit comprising Formula (XX).

Z is chosen from nitrogen, sulfur, sulfone, sulfoxide, and selenium; and n is an integer≥1.

Other features and iterations of the invention are described in more detail herein.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 1A-B shows the products formed after reaction of 2-hydroxy-4-(methylthio)-butanoic acid (HMTBA) with hydrochloric acid. (FIG. 1A) shows an HPLC chromatogram in which the different products are identified. (FIG. 1B) shows the same chromatogram as in (FIG. 1A) that is overlayed with a chromatogram showing the elution profile of 3,6-bis(2-methylthio)ethyl-1,4-dioxane-2,5 dione.

(FIG. 2A) shows an HPLC chromatogram in which the different compounds are identified. (FIG. 2B) shows the same chromatogram as in (FIG. 2A) that is overlayed with a chromatogram showing the elution profile of 3,6-bis(2-methylthio)ethyl-1,4-dioxane-2,5 dione.

DETAILED DESCRIPTION OF THE INVENTION

Figure 1A:
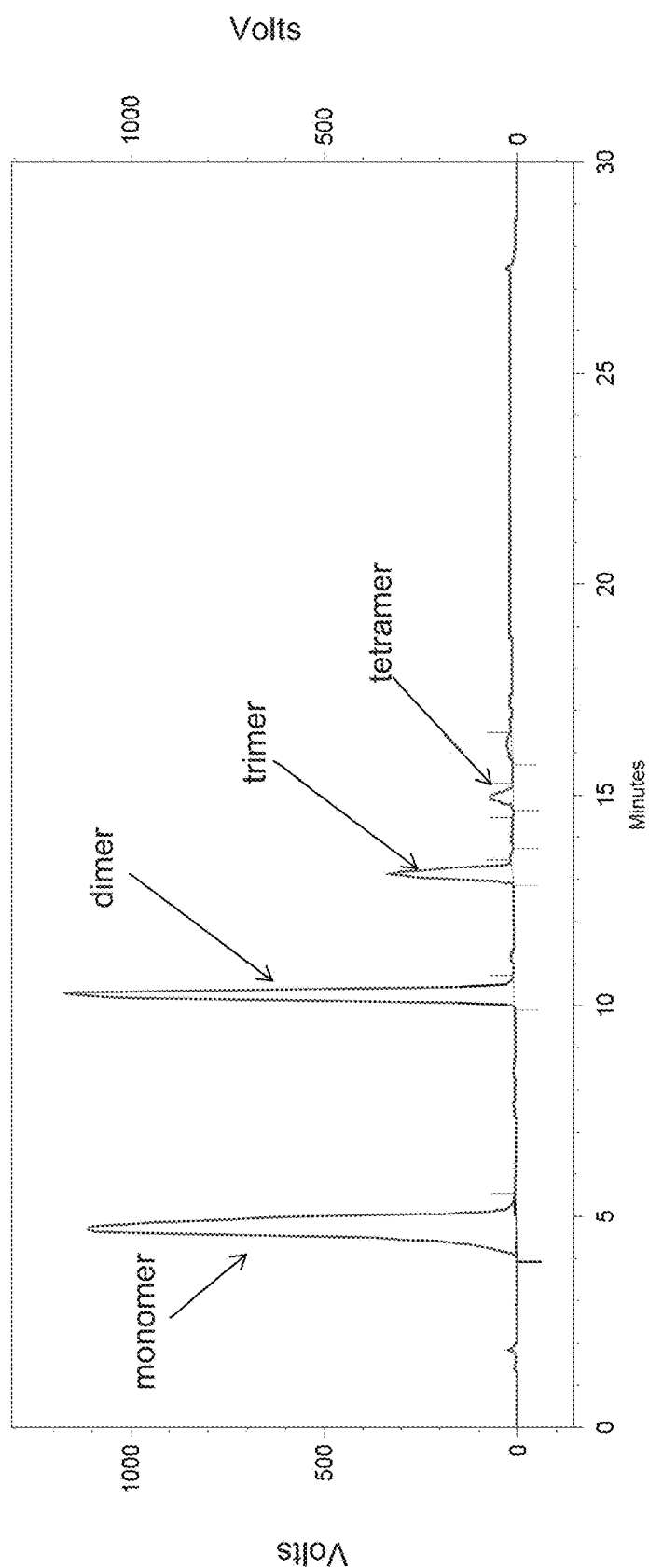

The present invention provides cyclic dimers of alpha acids that may be used for many purposes. The invention also provides methods for making the cyclic dimers, compositions comprising the cyclic dimers, and methods of using the cyclic dimers. Also provided are polymers prepared from the cyclic dimers, methods for preparing the polymers, and compositions comprising the polymers. Advantageously, polymers of very high molecular weight can be prepared from the cyclic dimers. The cyclic dimers and the polymers prepared from these cyclic dimers may be used, for example, as plasticizers, additives, processing aids, nutritive agents, antioxidant agents, antimicrobial agents, and feed additives.

The cyclic dimers of alpha acids, as disclosed herein, have the general structure shown below. For purposes of discussion, the ring atoms are numbered 1 to 6. Substitutions at the 3- and the 6-position may be described as pendant groups to the cyclic structure. Where no stereochemistry is shown, it is intended to represent any stereochemistry.

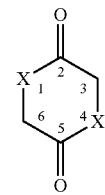

(I) Cyclic Dimer Compounds

One aspect of the invention provides cyclic dimer compounds comprising Formula (I):

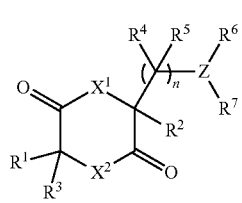

wherein,

X$^1$ and X$^2$ are independently chosen from nitrogen and oxygen, provided that both X$^1$ and X$^2$ are other than nitrogen;

R$^1$, R$^2$, R$^3$, R$^4$, and R$^5$ are independently chosen from hydrogen, hydrocarbyl, and substituted hydrocarbyl;

R$^6$ is chosen from hydrogen, hydrocarbyl, and substituted hydrocarbyl;

R$^7$ is optionally present, when present it is chosen from hydrogen, hydrocarbyl, and substituted hydrocarbyl;

Z is chosen from nitrogen, sulfur, sulfone, sulfoxide, and selenium; and n is an integer≥1;

provided that when Z is sulfur and n is 1, then R$^1$ and R$^3$ are other than hydrogen; and when Z is nitrogen, n is from 2 to 4, and R$^3$ is hydrogen, then R$^1$ is other than hydrogen or methyl.

The heteroatoms, X$^1$ and X$^2$, at the 1- and 4-positions of the ring are independently chosen from nitrogen and oxygen, provided that both are not nitrogen. In some embodiments, the heteroatoms are in their neutral state. Thus, where X$^1$ or X$^2$ is nitrogen, the nitrogen atom may be further substituted with another substituent. Additional substitutions of the heteroatom are preferably hydrogen, but may be chosen from various other groups known in the art. In other embodiments, the heteroatoms may hold a charge. In some embodiments, X$^1$ and X$^2$ are both oxygen. In other embodiments, X$^1$ is nitrogen and X$^2$ is oxygen. In still another embodiment, X$^1$ is oxygen and X$^2$ is nitrogen.

Each of R$^1$, R$^2$, R$^3$, R$^4$, R$^5$, R$^6$, and R$^7$ may be chosen from hydrogen, hydrocarbyl, or substituted hydrocarbyl. In various embodiments, the hydrocarbyl may be, but is not limited to, alkyl, cycloalkyl, alkenyl, alkenoxy, aryl, or alkylaryl. Substituted hydrocarbyl may be, without limit, arylalkoxyl, alkoxy, alkoxycarbonyl, carbonyl, acyl, acyloxy, sulfonyl, sulfonyl halide, sulfonyl ester, carboxyl, carboxylic acid, hydroxyalkyl, alkyl halide, alkyl amine, alkyl amide, substituted alkyl amine, or alkyl amide. In certain embodiments, R$^1$, R$^2$, R$^3$, R$^4$, R$^5$, R$^6$, and R$^7$ may be chosen from hydrogen, alkyl, aryl, alkylaryl, substituted alkyl, substituted aryl, and substituted alkylaryl. In various aspects, one or more of R$^2$, R$^3$, R$^4$, R$^5$, R$^6$, and R$^7$ may be hydrogen. In an exemplary embodiment, each of R$^2$, R$^3$, R$^4$, and R$^5$ is hydrogen.

In some embodiments, $R^2$ and $R^3$ are independently chosen from hydrocarbyl, substituted hydrocarbyl, and hydrogen. In some embodiments, $R^2$ and $R^3$ are lower chain alkyl groups including methyl, ethyl, propyl, butyl, pentyl, and hexyl. In another embodiment $R^2$ and $R^3$ are phenyl, benzyl, or substituted phenyl or benzyl. In preferred embodiments, $R^2$ is hydrogen and $R^3$ is chosen from hydrogen, methyl, ethyl, phenyl, and benzyl. In one embodiment, $R^2$ and $R^3$ are hydrogen.

$R^4$ and $R^5$ are independently chosen from hydrogen, hydrocarbyl, and substituted hydrocarbyl. In some embodiments, $(CR^4R^5)_n$ constitutes a hydrocarbyl chain, which may be linear or branched, with n representing the number of linked carbon atoms in the chain. In various embodiments, n is equal to or greater than 1. In some embodiments, n ranges from 1 to 20 and the hydrocarbyl chain comprises from 1 to 20 linked carbon atoms. In still another embodiment, n is equal to 2, 3, 4, 5, 6, 7, 8, 9, 10, 11, 12, 13, 14, 15, 16, 17, 18, 19, or 20. In exemplary embodiments, n is 1 or 2. In some embodiments, $R^4$ and $R^5$ may be hydrogen throughout the chain, in other aspects $R^4$ and $R^5$ are hydrocarbyl or substituted hydrocarbyl throughout the chain.

$R^6$ may be chosen from hydrogen, hydrocarbyl, substituted hydrocarbyl. Where $R^6$ is a hydrocarbyl, it may be any alkyl chain but is preferably a lower chain alkyl group such as methyl, ethyl, propyl, butyl, pentyl, or hexyl. The lower alkyl groups may additionally be branched or cyclic. Non-limiting examples include isopropyl, isobutyl, sec-butyl, t-butyl, cyclopropyl, cyclobutyl, cyclopentyl, and the like. In another embodiment, $R^6$ is phenyl, benzyl, or substituted phenyl or benzyl. In an exemplary embodiment, $R^6$ is methyl.

$R^7$ may be optionally present in the compound comprising Formula (I). When present, $R^7$ is chosen from hydrocarbyl, substituted hydrocarbyl, and hydrogen. Where $R^7$ is a hydrocarbyl, it may be any alkyl group but is preferably a lower chain alkyl group such as methyl, ethyl, propyl, butyl, pentyl, or hexyl. The lower alkyl groups may additionally be branched or cyclic, non-limiting examples include isopropyl, isobutyl, sec-butyl, t-butyl, cyclopropyl, cyclobutyl, cyclopentyl, and the like. In another embodiment, $R^7$ may be phenyl, benzyl, or substituted phenyl or benzyl. In a further embodiment, $R^7$ may be hydrogen.

The compounds comprising Formula (I) also contain a heteroatom (Z). In some embodiments, Z is nitrogen, selenium, or sulfur atom, including sulfoxide and sulfone groups. The nitrogen, selenium, or sulfur atoms may be charged and/or be present in various oxidation states within the molecule. Where the Z carries a charge, the compound may further comprise a counterion including, but not limited to lithium, sodium, potassium, calcium, magnesium, and the like.

In certain embodiments, when Z is sulfur and n is 1, then $R^1$ and $R^3$ are other than hydrogen. In other embodiments, when Z is nitrogen, n is from 2 to 4, and $R^3$ is hydrogen, then $R^1$ is other than hydrogen or methyl.

In some embodiments, $R^1$ comprises $(CR^8R)_mYR^{10}R^{11}$ and the compound comprises Formula (Ia):

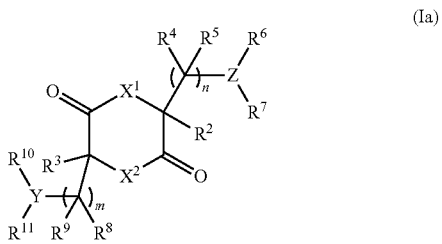

wherein:
$R^2$, $R^3$, $R^4$, $R^5$, $R^6$, $R^7$, $X^1$, $X^2$, Z, and n are as described above for the compound comprising Formula (I);
$R^8$, $R^9$, and $R^{10}$ are independently chosen from hydrogen, hydrocarbyl, and substituted hydrocarbyl;
$R^{11}$ is optionally present, when present it is chosen from hydrogen, hydrocarbyl, and substituted hydrocarbyl;
Y is chosen from nitrogen, sulfur, sulfone, sulfoxide, and selenium; and
m is an integer $\geq 1$.

Each of $R^8$, $R^9$, $R^{10}$, and $R^{11}$ may be chosen from hydrogen, hydrocarbyl, and substituted hydrocarbyl. The hydrocarbyl may be, without limit, alkyl, cycloalkyl, alkenyl, alkenoxy, aryl, or alkylaryl. The substituted hydrocarbyl may be, without limit, arylalkoxyl, alkoxy, alkoxycarbonyl, carbonyl, acyl, acyloxy, sulfonyl, sulfonyl halide, sulfonyl ester, carboxyl, carboxylic acid, hydroxyalkyl, alkyl halide, alkyl amine, alkyl amide, substituted alkyl amine, or alkyl amide. In certain embodiments, each of $R^8$, $R^9$, $R^{10}$, and $R^{11}$ may be chosen from hydrogen, alkyl, aryl, alkylaryl, substituted alkyl, substituted aryl, and substituted alkylaryl. In various aspects, one or more of $R^8$, $R^9$, $R^{10}$, and $R^{11}$ may be hydrogen. In an exemplary embodiment, $R^3$, $R^8$, and $R^9$ are hydrogen.

Where $R^{10}$ is a hydrocarbyl, it may be any alkyl chain but is preferably a lower chain alkyl group such as methyl, ethyl, propyl, butyl, pentyl, or hexyl. The lower alkyl groups may additionally be branched or cyclic. Non-limiting examples include isopropyl, isobutyl, sec-butyl, t-butyl, cyclopropyl, cyclobutyl, cyclopentyl, and the like. In another embodiment, $R^{10}$ is phenyl, benzyl, or substituted phenyl or benzyl. In an exemplary embodiment, $R^{10}$ is methyl.

$R^{11}$ may be optionally present in the compound comprising Formula (Ia). When present, $R^{11}$ is chosen from hydrocarbyl, substituted hydrocarbyl, and hydrogen. Where $R^{11}$ is hydrocarbyl, it may be any alkyl group but is preferably a lower chain alkyl group such as methyl, ethyl, propyl, butyl, pentyl, or hexyl. The lower alkyl groups may additionally be branched or cyclic, non-limiting examples include isopropyl, isobutyl, sec-butyl, t-butyl, cyclopropyl, cyclobutyl, cyclopentyl, and the like. In another embodiment, $R^{11}$ may be phenyl, benzyl, or substituted phenyl or benzyl. In a further embodiment, $R^{11}$ may be hydrogen.

In some embodiments, $(CR^8R^9)_m$ constitutes a hydrocarbyl chain, which may be linear or branched, with m representing the number of linked carbon atoms in the chain. In various embodiments, m is equal to or greater than 1. In some embodiments, m ranges from 1 to 20 and the hydrocarbyl chain comprises from 1 to 20 linked carbon atoms. In still another embodiment, m is equal to 2, 3, 4, 5, 6, 7, 8, 9, 10, 11, 12, 13, 14, 15, 16, 17, 18, 19, or 20. In exemplary embodiments, m is 1 or 2. In some embodiments, $R^8$ and $R^9$ may be hydrogen throughout the chain, in other aspects $R^8$ and $R^9$ are hydrocarbyl or substituted hydrocarbyl throughout the chain.

The compounds comprising Formula (Ia) also contain a heteroatom (Y). In some embodiments, Y is nitrogen, selenium, or sulfur atom, including sulfoxide and sulfone groups. The nitrogen, selenium, or sulfur atoms may be charged and/or be present in various oxidation states within the molecule. Where the Y carries a charge, the compound may further comprise a counterion including, but not limited to lithium, sodium, potassium, calcium, magnesium, and the like.

In one embodiment, $R^2$, $R^3$, $R^4$, $R^5$, $R^8$ and $R^9$ are hydrogen, n and m independently range from 1 to 10; Z and Y are independently chosen from sulfur, sulfone, sulfoxide, and selenium. In some iterations, $R^6$ and $R^{10}$ are lower chain alkyl, and $R^7$ and $R^{11}$, if present, are independently hydrogen or lower chain alkyl.

Non-limiting compounds comprising Formula (I) or Formula (Ia) are listed in Table 1.

TABLE 1

Exemplary compounds comprising Formulas (I) or (IIa).

| # | $X^1$ | $X^2$ | Z | n | $R^1$ | $R^3$ | $R^4$ | $R^5$ | $R^6$ | $R^7$ |
|---|---|---|---|---|---|---|---|---|---|---|
| 1 | N | O | S | 1 | $(CH_2)_2SCH_3$ | H | H | H | $CH_3$ | — |
| 2 | N | O | S | 1 | $CH_2SCH3$ | H | H | H | $CH_2CH_3$ | — |
| 3 | N | O | S | 2 | $CH_3$ | H | H | H | $CH_3$ | $CH_3$ |
| 4 | N | O | S | 2 | $CH_2Ph$ | H | H | H | $CH_2CH_3$ | $CH_3$ |
| 5 | N | O | SO | 1 | $CH_3$ | H | H | H | $CH_3$ | — |
| 6 | N | O | SO | 1 | $(CH_2)_2SCH_3$ | H | H | H | $CH_3$ | — |
| 7 | N | O | SO | 2 | $(CH_2)_2SOCH_3$ | H | H | H | $CH_3$ | — |
| 8 | N | O | SO | 2 | $(CH_2)_2SeCH_3$ | H | H | H | $CH_2CH_3$ | — |
| 9 | N | O | $SO_2$ | 1 | $CH_2Ph$ | H | H | H | $CH_2CH_3$ | — |
| 10 | N | O | $SO_2$ | 1 | $CH_3$ | H | H | H | $CH_3$ | — |
| 11 | N | O | $SO_2$ | 2 | $(CH_2)_2SCH_3$ | H | H | H | Ph | — |
| 12 | N | O | $SO_2$ | 2 | $(CH_2)_2SOCH_3$ | H | H | H | $CH_2CH_3$ | — |
| 13 | N | O | $SO_2$ | 2 | $(CH_2)_2SOCH_3$ | H | H | H | $CH_3$ | — |
| 14 | N | O | $SO_2$ | 2 | $(CH_2)_2SO_2CH_3$ | H | H | H | $CH_3$ | — |
| 15 | N | O | SO | 2 | $(CH_2)_2SO_2CH_3$ | H | H | H | $CH_3$ | — |
| 16 | N | O | N | 1 | $(CH_2)_2N(CH_3)CH_2CH_3$ | H | H | H | $CH_2CH_3$ | $CH_3$ |
| 17 | N | O | Se | 1 | $CH_2SeCH_3$ | H | H | H | $CH_3$ | — |
| 18 | N | O | Se | 2 | $(CH_2)_2SeCH_3$ | H | H | H | $CH_3$ | — |
| 19 | O | N | S | 1 | $(CH_2)_2SCH_3$ | H | H | H | $CH_3$ | — |
| 20 | O | N | S | 1 | $CH_2SCH3$ | H | H | H | $CH_2CH_3$ | — |
| 21 | O | N | S | 2 | $CH_3$ | H | H | H | $CH_3$ | $CH_3$ |
| 22 | O | N | S | 2 | $CH_2Ph$ | H | H | H | $CH_2CH_3$ | $CH_3$ |
| 23 | O | N | SO | 1 | $CH_3$ | H | H | H | $CH_3$ | — |
| 24 | O | N | SO | 1 | $(CH_2)_2SCH_3$ | H | H | H | $CH_3$ | — |
| 25 | O | N | SO | 2 | $(CH_2)_2SO_2CH_3$ | H | H | H | $CH_3$ | — |
| 26 | O | N | SO | 2 | $(CH_2)_2SeCH_3$ | H | H | H | $CH_2CH_3$ | — |
| 27 | O | N | $SO_2$ | 1 | $CH_2Ph$ | H | H | H | $CH_2CH_3$ | — |
| 28 | O | N | $SO_2$ | 1 | $CH_3$ | H | H | H | $CH_3$ | — |
| 29 | O | N | $SO_2$ | 2 | $(CH_2)_2SCH_3$ | H | H | H | $CH_3$ | — |
| 30 | O | N | $SO_2$ | 2 | $(CH_2)_2SOCH_3$ | H | H | H | $CH_2CH_3$ | — |
| 31 | O | N | $SO_2$ | 2 | $(CH_2)_2SOCH_3$ | H | H | H | $CH_3$ | — |
| 32 | O | N | $SO_2$ | 2 | $(CH_2)_2SO_2CH_3$ | H | H | H | $CH_3$ | — |
| 33 | O | N | N | 1 | $(CH_2)_2N(CH_3)CH_2CH_3$ | H | H | H | $CH_2CH_3$ | $CH_3$ |
| 34 | O | N | Se | 1 | $CH_2SeCH_3$ | H | H | H | $CH_3$ | — |
| 35 | O | N | Se | 2 | $(CH_2)_2SeCH_3$ | H | H | H | $CH_3$ | — |
| 36 | O | O | S | 1 | $(CH_2)_2SCH_3$ | H | H | H | Ph | — |
| 37 | O | O | S | 1 | $CH_2SCH3$ | H | H | H | $CH_2CH_3$ | — |
| 38 | O | O | S | 2 | $CH_3$ | H | H | H | $CH_3$ | $CH_3$ |
| 39 | O | O | S | 2 | $CH_2Ph$ | H | H | H | $CH_2CH_3$ | $CH_3$ |
| 40 | O | O | SO | 1 | $CH_3$ | H | H | H | $CH_3$ | — |
| 41 | O | O | SO | 1 | $(CH_2)_2SCH_3$ | H | H | H | $CH_3$ | — |
| 42 | O | O | SO | 2 | $(CH_2)_2SO_2CH_3$ | H | H | H | $CH_3$ | — |
| 43 | O | O | SO | 2 | $(CH_2)_2SOCH_3$ | H | H | H | $CH_3$ | — |
| 44 | O | O | SO | 2 | $(CH_2)_2SeCH_3$ | H | H | H | $CH_2CH_3$ | — |
| 45 | O | O | SO | 2 | $(CH_2)_2SOCH_3$ | H | H | H | $CH_3$ | — |
| 46 | O | O | $SO_2$ | 1 | $CH_2Ph$ | H | H | H | $CH_2CH_3$ | — |
| 47 | O | O | $SO_2$ | 1 | $CH_3$ | H | H | H | $CH_3$ | — |
| 48 | O | O | $SO_2$ | 2 | $(CH_2)_2SCH_3$ | H | H | H | $CH_3$ | — |
| 49 | O | O | $SO_2$ | 2 | $(CH_2)_2SOCH_3$ | H | H | H | $CH_2CH_3$ | — |
| 50 | O | O | $SO_2$ | 2 | $(CH_2)_2SO_2CH_3$ | H | H | H | $CH_3$ | — |
| 51 | O | O | N | 1 | $(CH_2)_2NCH_3CH_2CH_3$ | H | H | H | $CH_2CH_3$ | $CH_3$ |
| 52 | O | O | Se | 1 | $CH_2SeCH_3$ | H | H | H | Ph | — |
| 53 | O | O | Se | 2 | $(CH_2)_2SeCH_3$ | H | H | H | $CH_3$ | — |

54 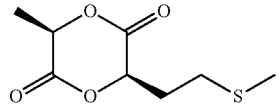

TABLE 1-continued

Exemplary compounds comprising Formulas (I) or (IIa).

| # | X¹ | X² | Z | n | R¹ | R³ | R⁴ | R⁵ | R⁶ | R⁷ |
|---|---|---|---|---|---|---|---|---|---|---|
| 55 | | | | | 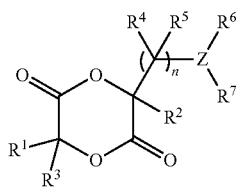 | | | | | |
| 56 | | | | | | | | | | |
| 57 | | | | | | | | | | |

In an alternative embodiment, the compound comprises Formula (II):

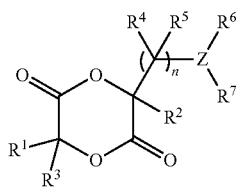

wherein, $R^1$, $R^2$, $R^3$, $R^4$, and $R^5$ are independently chosen from hydrogen, hydrocarbyl and substituted hydrocarbyl;

$R^6$ is chosen from hydrogen, hydrocarbyl, and substituted hydrocarbyl;

$R^7$ is optionally present, when present it is chosen from hydrogen, hydrocarbyl, and substituted hydrocarbyl;

Z is chosen from nitrogen, sulfur, sulfone, sulfoxide, and selenium; and n is an integer ≥ 1;

provided that when Z is sulfur and n is 1, then $R^1$ and $R^3$ are other than hydrogen; and when Z is nitrogen, n is 2 or 4, and $R^3$ is hydrogen, then $R^1$ is other than methyl.

Each of $R^1$, $R^2$, $R^3$, $R^4$, $R^5$, $R^6$, $R^7$, Z, and n may be chosen as described for Formula (I). In some embodiments of the compound comprising Formula (II), when Z is nitrogen, then either both $R^1$ and $R^3$ are methyl or neither $R^1$ nor $R^3$ is methyl. In another embodiment in which Z is sulfur, then $R^6$ is not hydrogen or benzyl. In yet another embodiment in which Z is sulfur and n is 1, then $R^6$ is not hydrogen, benzyl, or paramethoxybenzyl.

In one embodiment, the compound comprises Formula (IIb):

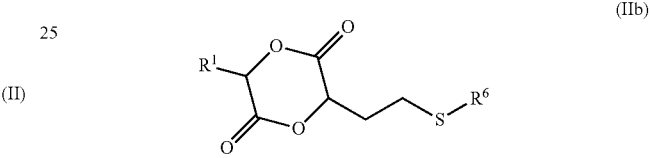

wherein;

$R^1$ and $R^6$ are independently chosen from hydrogen, alkyl, aryl, alkylaryl, substituted alkyl, substituted aryl, and substituted alkylaryl.

In some embodiments, $R^1$ is chosen from methyl, ethyl, phenyl, and benzyl; and $R^6$ is chosen from hydrogen, methyl, and ethyl. In an exemplary embodiment, both $R^1$ and $R^6$ are methyl, as in the compound comprising Formula (IIc):

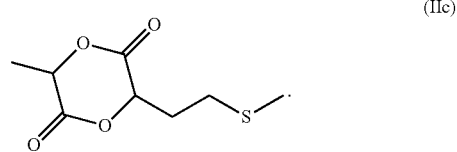

The atoms at the 3- and 6-positions of the ring of the compound comprising Formula (IIb) or Formula (IIc) may have a configuration chosen from RR, RS, SR, and SS, respectively.

In additional embodiments, $R^1$ of the compound comprising Formula (II) comprises $(CR^8R^9)_m YR^{10}R^{11}$ such that the compound comprises Formula (IIa):

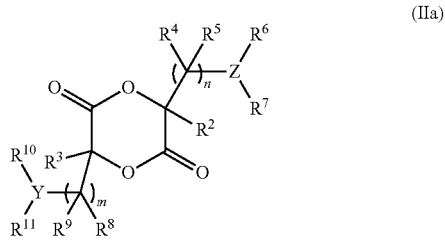

wherein:

R², R³, R⁴, R⁵, R⁶, R⁷, Z, and n are as described above for the compounds comprising Formula (II);

R⁸, R⁹, and R¹⁰ are independently chosen from hydrogen, hydrocarbyl, and substituted hydrocarbyl;

R¹¹ is optionally present, when present it is chosen from hydrogen, hydrocarbyl, and substituted hydrocarbyl;

Y is chosen from nitrogen, sulfur, sulfone, sulfoxide, and selenium; and m is an integer≥1.

Each of R², R³, R⁴, R⁵, R⁶, R⁷, Z, and n may be chosen as described for compounds comprising Formula (I), and each of R⁸, R⁹, R¹⁰, R¹¹, Y and m may be chosen as described for compounds comprising Formula (Ia).

In some embodiments of the compound comprising Formula (IIa), the two pendant groups do not comprise a lysine or lysine derivative. In some embodiments, when Z and Y are nitrogen, and n and m are 4 or 5, then R⁶ and R¹⁰ are not hydrogen or COOR⁸, and R⁸ and R¹¹ are chosen from hydrogen, benzyl, and t-butyl.

In various embodiments, R², R³, R⁴, R⁵, R⁸ and R⁹ are hydrogen, n and m independently range from 1 to 10; Z and Y are independently chosen from sulfur, sulfone, sulfoxide, and selenium. In some iterations, R⁶ and R¹⁰ are lower chain alkyl, and R⁷ and R¹¹, if present, are independently hydrogen or lower chain alkyl. In an exemplary embodiment, each of R², R³, R⁴, R⁵, R⁸ and R⁹ are hydrogen, both n and m are 2, both Z and Y are sulfur, both R⁶ and R¹⁰ are methyl, and neither R⁷ nor R¹¹ are present.

Non-limiting examples of compounds comprising Formula (II) or Formula (IIa) are shown in Table 2.

TABLE 2

Exemplary compounds comprising Formulas (II) or (IIa).

1

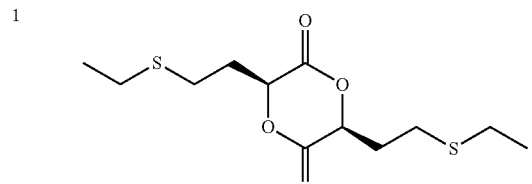

2

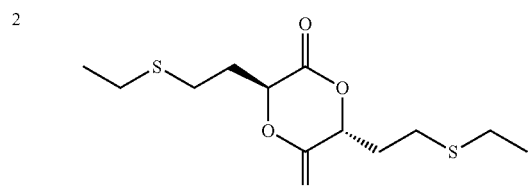

3

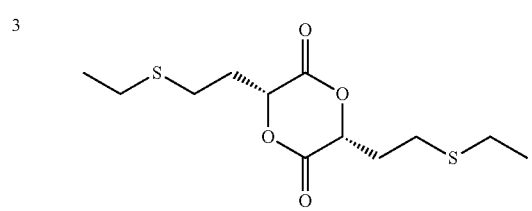

TABLE 2-continued

Exemplary compounds comprising Formulas (II) or (IIa).

4

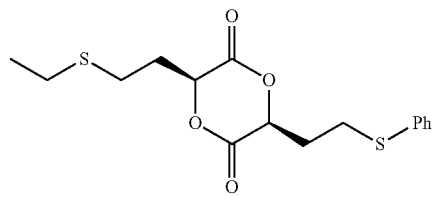 [SMILES: CCSCC[C@@H]1OC(=O)[C@H](CCSc2ccccc2)OC1=O]

5

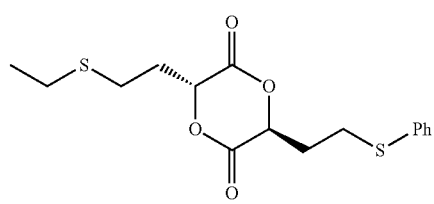 [SMILES: CCSCC[C@H]1OC(=O)[C@H](CCSc2ccccc2)OC1=O]

6

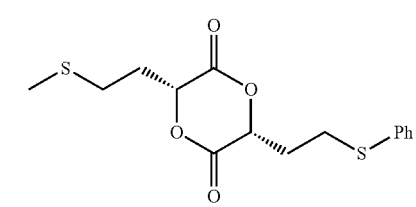 [SMILES: CSCC[C@H]1OC(=O)[C@@H](CCSc2ccccc2)OC1=O]

7

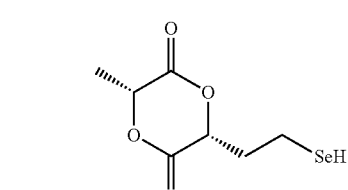

8

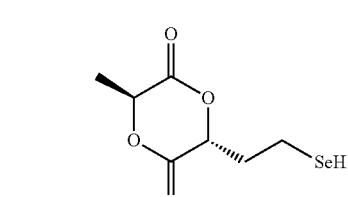

9

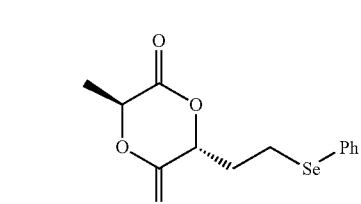

10

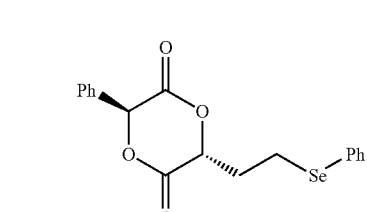

TABLE 2-continued
Exemplary compounds comprising Formulas (II) or (IIa).
11 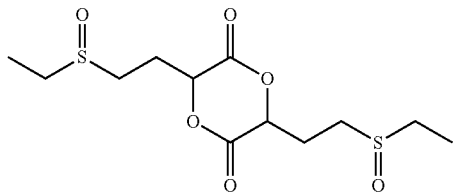 [SMILES: CCS(=O)CCC1OC(=O)C(CCS(=O)CC)OC1=O]
12 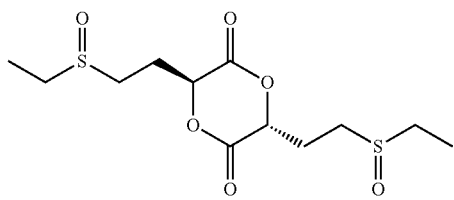 [SMILES: CCS(=O)CC[C@@H]1OC(=O)[C@@H](CCS(=O)CC)OC1=O]
13 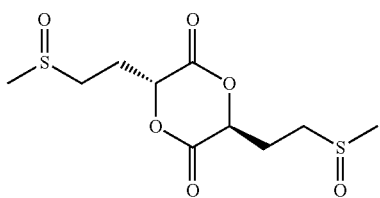
14 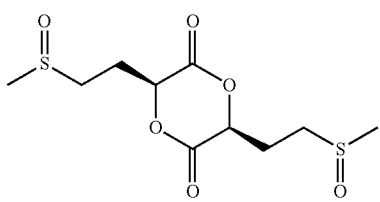
15 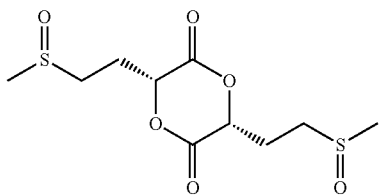
16 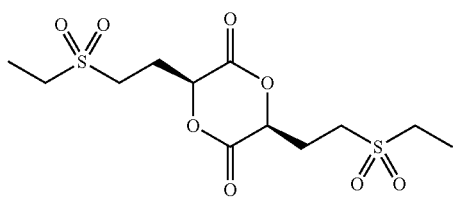 [SMILES: CCS(=O)(=O)CC[C@@H]1OC(=O)[C@H](CCS(=O)(=O)CC)OC1=O]
17 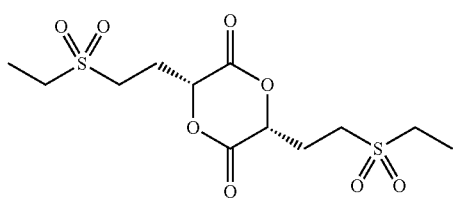 [SMILES: CCS(=O)(=O)CC[C@H]1OC(=O)[C@@H](CCS(=O)(=O)CC)OC1=O]
TABLE 2-continued
Exemplary compounds comprising Formulas (II) or (IIa).
18 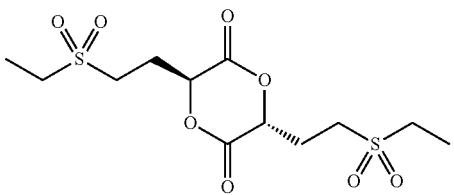 [SMILES: CCS(=O)(=O)CC[C@@H]1OC(=O)[C@@H](CCS(=O)(=O)CC)OC1=O]
19 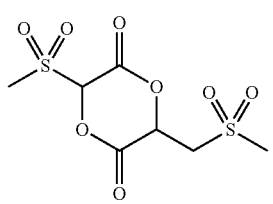
20 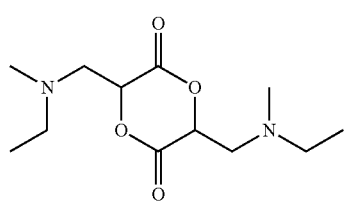 [SMILES: CCN(C)CC1OC(=O)C(CN(C)CC)OC1=O]
21 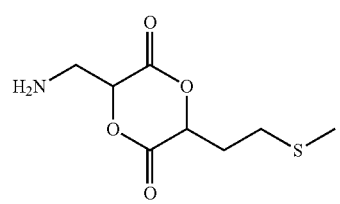
22 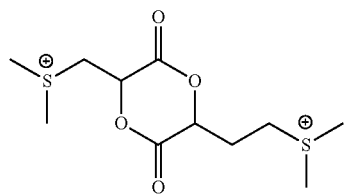
23 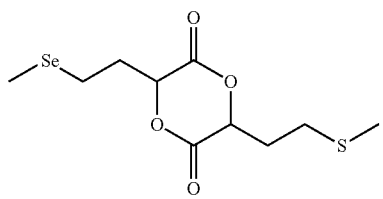
24 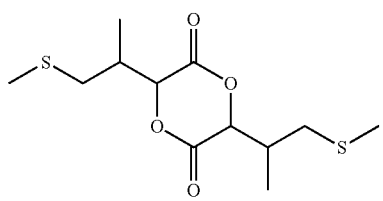

TABLE 2-continued

Exemplary compounds comprising Formulas (II) or (IIa).

| 25 | 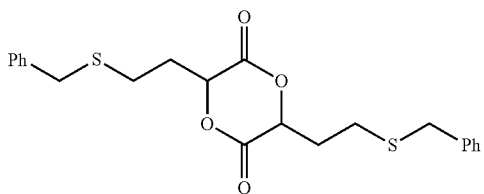 |
| --- | --- |
| 26 | 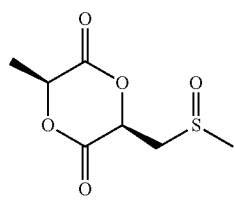 |
| 27 | 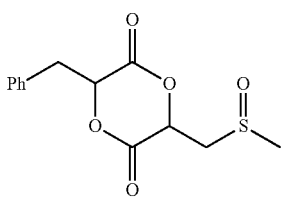 [SMILES: CS(=O)CC1OC(=O)C(Cc2ccccc2)OC1=O] |
| 28 | 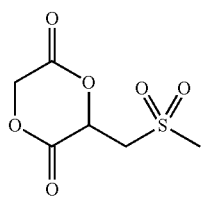 |
| 29 | 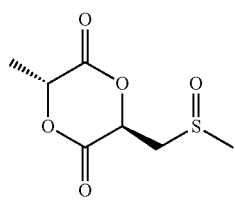 |
| 30 | 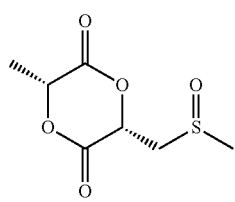 |

In still other embodiments, the compound comprises Formula (III):

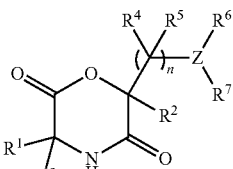

(III)

wherein, $R^1$, $R^2$, $R^3$, $R^4$, and $R^5$ are independently chosen from hydrogen, hydrocarbyl and substituted hydrocarbyl;

$R^6$ is chosen from hydrogen, hydrocarbyl, and substituted hydrocarbyl;

$R^7$ is optionally present, when present it is chosen from hydrogen, hydrocarbyl, and substituted hydrocarbyl;

Z is chosen from nitrogen, sulfur, sulfone, sulfoxide, and selenium; and n is an integer≥to 1.

Each of $R^1$, $R^2$, $R^3$, $R^4$, $R^5$, $R^6$, $R^7$, Z, and n may be chosen as described for Formula (I).

In some embodiments, $R^1$ of the compound comprising Formula (III) comprises $(CR^8R^9)_mYR^{10}R^{11}$ and the compound comprises Formula (IIIa):

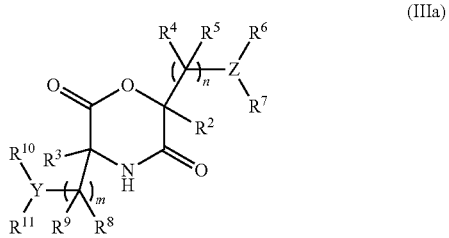

(IIIa)

wherein:

$R^2$, $R^3$, $R^4$, $R^5$, $R^6$, $R^7$, Z, and n are as described above for the compound comprising Formula (III);

$R^8$, $R^9$, and $R^{10}$ are independently chosen from hydrogen, hydrocarbyl, and substituted hydrocarbyl;

$R^{11}$ is optionally present, when present it is chosen from hydrogen, hydrocarbyl, and substituted hydrocarbyl;

Y is chosen from nitrogen, sulfur, sulfone, sulfoxide, and selenium; and m is an integer≥1.

Each of $R^2$, $R^3$, $R^4$, $R^5$, $R^6$, $R^7$, Z, and n may be chosen as described for compounds comprising Formula (I), and each of $R^8$, $R^9$, $R^{10}$, $R^{11}$, Y, and m may be chosen as described for compounds comprising Formula (Ia).

In various embodiments, $R^2$, $R^3$, $R^4$, $R^5$, $R^8$ and $R^9$ are hydrogen, n and m independently range from 1 to 10; Z and Y are independently chosen from sulfur, sulfone, sulfoxide, and selenium. In some iterations, $R^6$ and $R^{10}$ are lower chain alkyl, and $R^7$ and $R^{11}$, if present, are independently hydrogen or lower chain alkyl.

Non-limiting compounds comprising Formula (III) or Formula (IIIa) are presented in Table 3.

TABLE 3
Exemplary compounds comprising Formulas (III) or (IIIa).
1
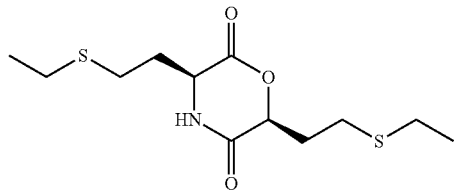 [SMILES: CCSCC[C@@H]1NC(=O)[C@H](CCSCC)OC1=O]
2
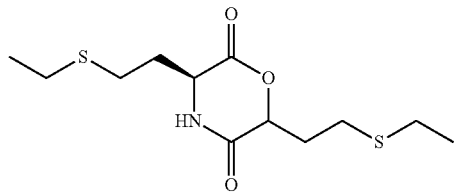 [SMILES: CCSCCC1OC(=O)[C@H](CCSCC)NC1=O]
3
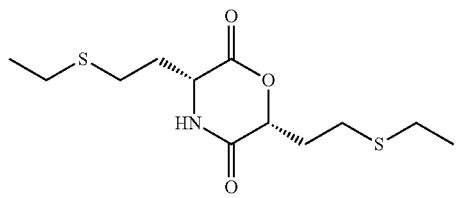 [SMILES: CCSCC[C@H]1NC(=O)[C@@H](CCSCC)OC1=O]
4
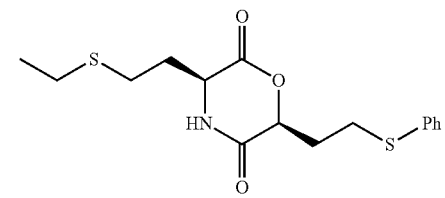 [SMILES: CCSCC[C@@H]1NC(=O)[C@H](CCSc2ccccc2)OC1=O]
5
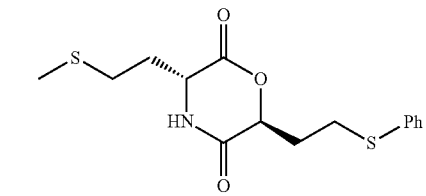 [SMILES: CSCC[C@H]1NC(=O)[C@H](CCSc2ccccc2)OC1=O]
6
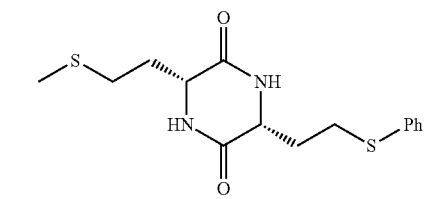 [SMILES: CSCC[C@H]1NC(=O)[C@@H](CCSc2ccccc2)NC1=O]
7
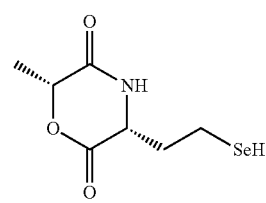
TABLE 3-continued
Exemplary compounds comprising Formulas (III) or (IIIa).
8
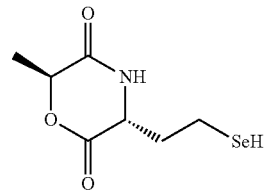
9
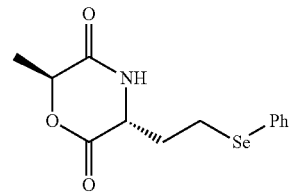 [SMILES: C[C@@H]1OC(=O)[C@@H](CC[Se]c2ccccc2)NC1=O]
10
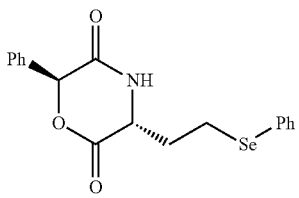 [SMILES: O=C1N[C@H](CC[Se]c2ccccc2)C(=O)O[C@H]1c1ccccc1]
11
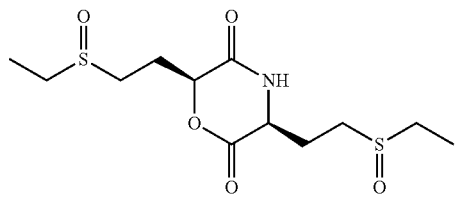 [SMILES: CCS(=O)CC[C@@H]1NC(=O)[C@H](CCS(=O)CC)OC1=O]
12
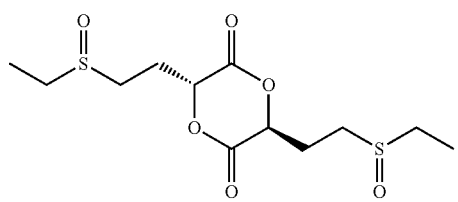 [SMILES: CCS(=O)CC[C@@H]1OC(=O)[C@@H](CCS(=O)CC)OC1=O]
13
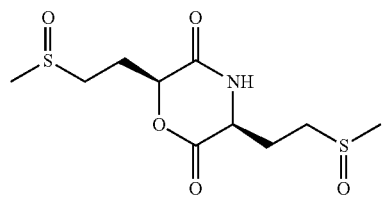
14
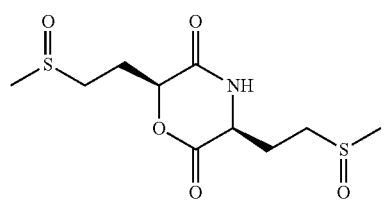

TABLE 3-continued
Exemplary compounds comprising Formulas (III) or (IIIa).
15 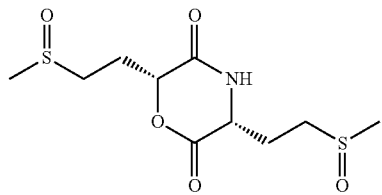
16 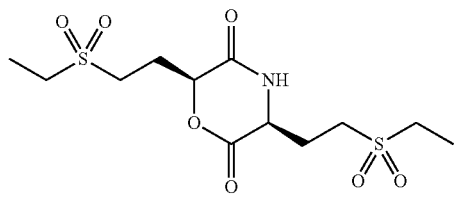 [SMILES: CCS(=O)(=O)CC[C@@H]1NC(=O)[C@H](CCS(=O)(=O)CC)OC1=O]
17 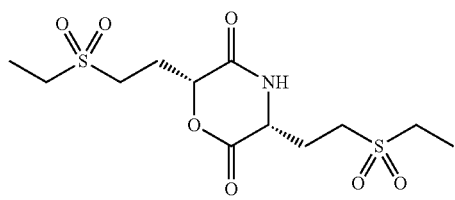 [SMILES: CCS(=O)(=O)CC[C@H]1NC(=O)[C@@H](CCS(=O)(=O)CC)OC1=O]
18 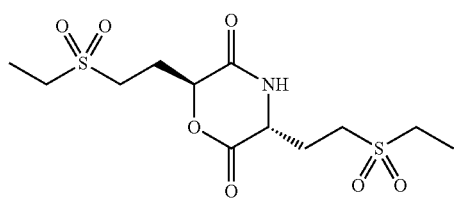 [SMILES: CCS(=O)(=O)CC[C@@H]1OC(=O)[C@@H](CCS(=O)(=O)CC)NC1=O]
19 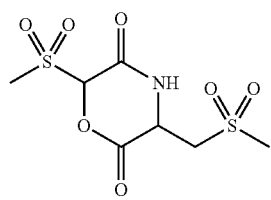
20 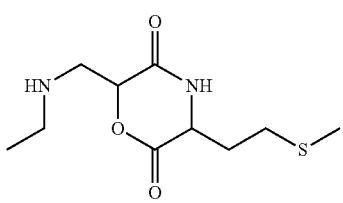 [SMILES: CCNCC1OC(=O)C(CCSC)NC1=O]
21 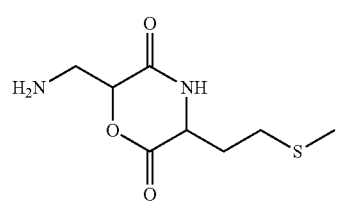
TABLE 3-continued
Exemplary compounds comprising Formulas (III) or (IIIa).
22 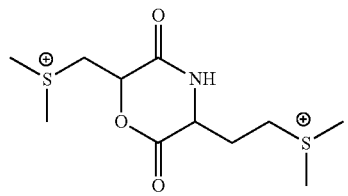
23 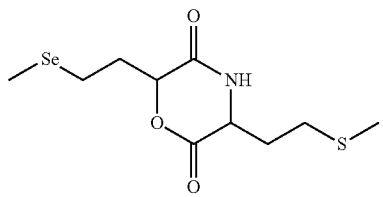
24 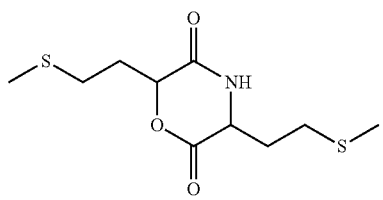
25 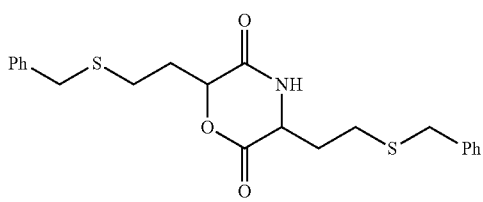 [SMILES: O=C1OC(CCSCc2ccccc2)C(=O)NC1CCSCc1ccccc1]
26 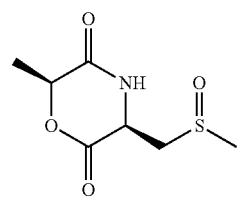
27 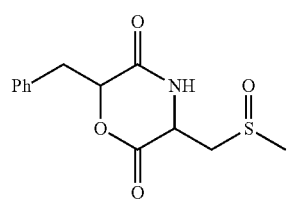 [SMILES: CS(=O)CC1NC(=O)C(Cc2ccccc2)OC1=O]
28 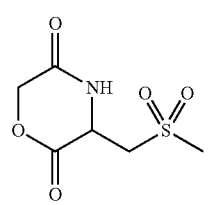

TABLE 3-continued

Exemplary compounds comprising Formulas (III) or (IIIa).

29 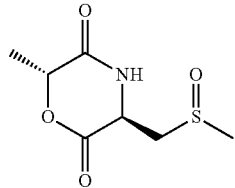

30 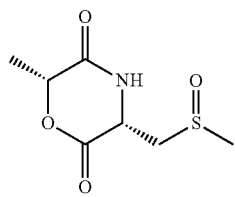

Yet another embodiment provides a compound comprising Formula (IV):

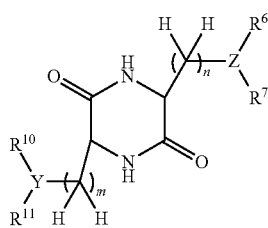

(IV)

wherein,

R$^6$ and R$^{10}$ are independently chosen from hydrogen, hydrocarbyl, and substituted hydrocarbyl;

R$^7$ and R$^{11}$ are optionally present, when present each is independently chosen from hydrogen, hydrocarbyl, and substituted hydrocarbyl;

Z and Y are independently chosen from sulfone, sulfoxide, and selenium; and n and m are integers≥1;

provided that when Z and Y are sulfoxide, then R$^6$ and R$^{10}$ are other than methyl.

Each of R$^6$, R$^7$, R$^{10}$, R$^{11}$, Y, Z, n, and m may be chosen as described above for compounds comprising Formulas (I) and (Ia).

In one embodiment of the compound comprising Formula (IV), Y and Z are selenium, R$^6$ and R$^{10}$ are lower alkyl, and R$^7$ and R$^{11}$ are not present. In another embodiment, Y and Z are selenium, R$^6$ and R$^{10}$ are methyl, and R$^7$ and R$^{11}$ are not present. Table 4 lists non-limiting examples of compounds comprising Formula (IV).

TABLE 4

Exemplary compounds comprising Formula (IV).

1 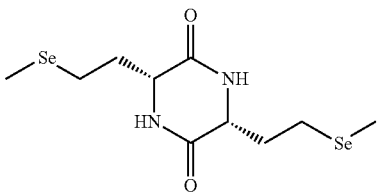

2 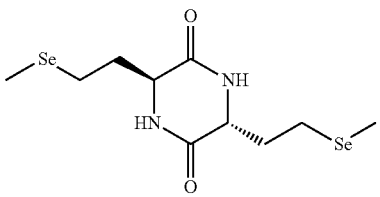

3 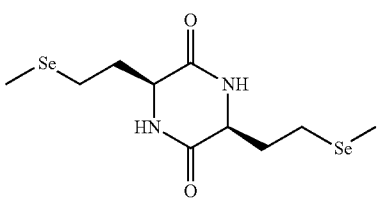

4 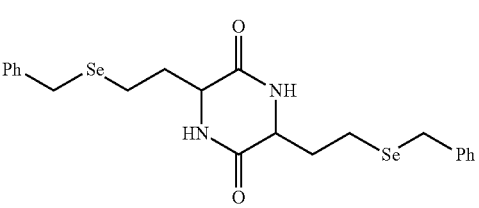 [SMILES: O=C1NC(CC[Se]Cc2ccccc2)C(=O)NC1CC[Se]Cc1ccccc1]

5 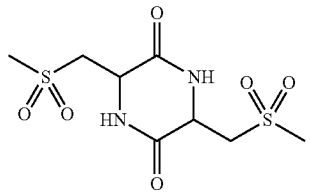

6 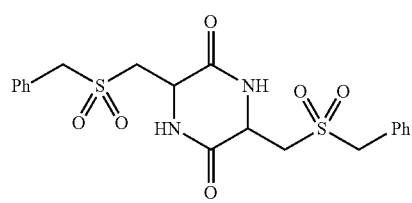 [SMILES: O=C1NC(CS(=O)(=O)Cc2ccccc2)C(=O)NC1CS(=O)(=O)Cc1ccccc1]

7 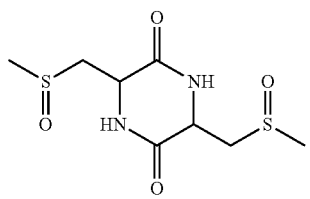

TABLE 4-continued

Exemplary compounds comprising Formula (IV).

| 8 | |
| --- | --- |
| 9 | |
| 10 | |

In exemplary embodiments, the compound of the invention comprises Formula (V):

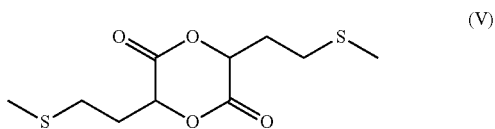

(V)

TABLE 5

Exemplary compounds comprising Formula (V).

| 1 | |
| --- | --- |
| 2 | |
| 3 | |
| 4 | |

In some aspects of the invention, the compounds comprise one or more chiral centers. Each chiral center of the compounds comprising Formulas (I), (II), (III), (IV), and (V) may have an R or an S configuration. In some embodiments, where the carbon atom at the 3-position and the 6-position has four different substituents, the positions are chiral centers. In such embodiments, the configurations at the 3- and 6-positions may be chosen from RR, RS, SR, and SS, respectively. In another aspect, compositions may be mixtures of two or more isomers. In another aspect, the compositions may be optically pure or enriched with one or more isomers. In aspects of the invention where the pendent groups at the 3- and 6-positions are the same, the compounds may comprise the D-isomer, the L-isomer, or the meso isomer. In another embodiment, the composition may be a mixture of two or more of the D-isomer, the L-isomer, and the meso isomer.

The compounds of the invention may also be provided as substantially pure compounds. In some aspects, the compounds are substantially pure in mixtures of stereoisomers that are substantially free from byproducts including monomers, non-cyclic dimers, or other oligomers. In another aspect, the compounds described herein may be provided as a substantially pure enantiomer or diastereomer. By substantially pure, it is meant that the desired compound is present in about 80% purity, about 90% purity, or about 95% purity, about 99% purity, about 99.5% purity, about 99.9% purity, 99.99% purity, or higher. In another embodiment, the compounds may be provided as optically pure compounds, optically pure compounds may have about 80%, about 90%, about 99% optical purity, about 99.9%, or about 99.99% optical purity, or higher.

The compounds provided in this section may have a variety of uses and purposes, in their cyclic forms or as polymers (see below). The compounds or compositions comprising the compounds provided herein may have one set of properties under one set of conditions and different properties under different conditions. In some embodiments, the compounds provided herein may be stable in aqueous solutions under approximately neutral pH. In other embodiments, the compounds provided herein may hydrolyze in aqueous solutions at pH values of less than about 6.0, less than about 5.0, less than about 3.0, less than about 2.0, or less than about 1.0.

(II) Processes for Preparing Cyclic Dimers

Still another aspect of the present disclosure encompasses processes for the preparation of the compounds disclosed herein. In particular, processes for the preparation of the cyclic dimers comprise contacting alpha acids under conditions such that the alpha acids form cyclic dimers.

(a) Preparation of Compounds Comprising Formula (IX)—Condensation

In one aspect, the process for producing a compound comprising Formula (IX) comprises (a) contacting a compound comprising Formula (VI) with a compound comprising Formula (VII) or a compound comprising Formula (VIII) and an acid catalyst and (b) dehydrating the resulting reaction mixture to form the compound comprising Formula (IX). The compounds comprising Formula (IX), (VI), (VII), and (VIII) have the following structures:

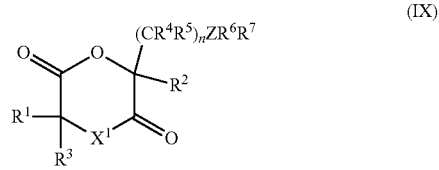

(IX)

-continued

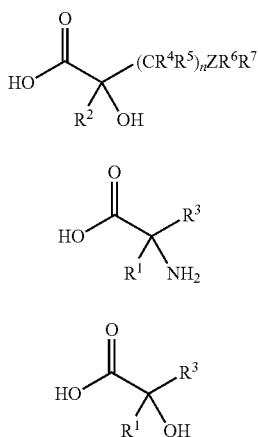

wherein,

X¹ is chosen from oxygen and nitrogen,

R¹, R², R³, R⁴, and R⁵ are independently chosen from hydrogen, hydrocarbyl, and substituted hydrocarbyl;

R⁶ is chosen from hydrogen, hydrocarbyl, and substituted hydrocarbyl;

R⁷ is optionally present, when present it is chosen from hydrogen, hydrocarbyl, and substituted hydrocarbyl;

Z is chosen from nitrogen, sulfur, sulfone, sulfoxide, and selenium; and n is an integer≥1.

R¹, R², R³, R⁴, R⁵, R⁶, R⁷, Z, and n may be chosen as described above for the compound comprising Formula (I) in section (I). In some embodiments, R¹ may be (CR⁸R⁹)$_m$YR¹⁰R¹¹, wherein R⁸, R⁹, R¹⁰, R¹¹, Y, and m may be chosen as described for compounds comprising Formula (Ia) in section (I).

In some embodiments, the process proceeds according to Reaction Scheme 1(a) to form the compound comprising Formula (II):

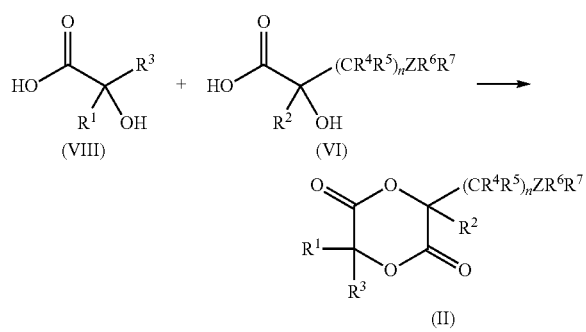

wherein R¹, R², R³, R⁴, R⁵, R⁶, R⁷, Z, and n are as defined above.

In still other embodiments, the reaction proceeds according to Reaction Scheme 1(b) to form the compound comprising Formula (III):

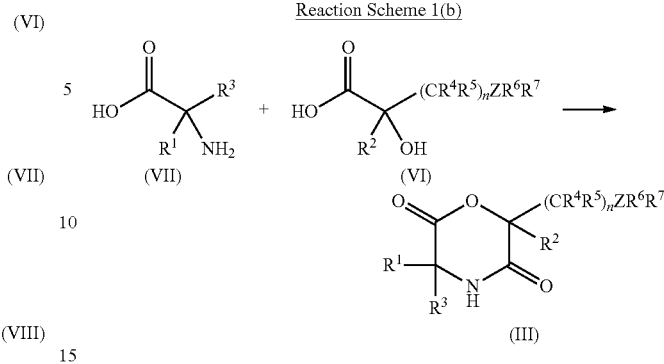

wherein R¹, R², R³, R⁴, R⁵, R⁶, R⁷, Z, and n are as defined above.

The compound comprising Formula (VII) may be an amino acid. Non-limiting examples of suitable amino acids include glycine, alanine, valine, leucine, isoleucine, phenylalanine, serine, threonine, lysine, Δ-hydroxylysine, ornithine, aspartic acid, glutamic acid, cysteine, cystine, methionine, selenomethionine, tyrosine, thyroxine, proline, hydroxyproline, and tryptophan. In some aspects, the amino acid does not require protection. In other aspects, the amino acid may be protected, for example on the side chain side chain or at the N-terminus by means known in the art.

The process comprises contacting the compound comprising Formula (VI) with a compound comprising Formula (VII) or a compound comprising Formula (VIII). In general, the two compounds are provided to the reaction in an approximately equal molar ratio. In some embodiments, the compound comprising Formula (VI) may be provided in a molar ratio with respect to the compound comprising Formula (VII) or Formula (VIII) of about 0.1:1, 0.2:1, 0.3:1, 0.4:1, 0.5:1, 0.6:1; 0.7:1, 0.8:1, 0.9:1, 1:1.0, 1:1.1, 1:1.2, 1:1.3, 1:1.4, 1:1.5, 1:1.6, 1:1.7, 1:1.8, 1:2.0, 1:2.5, 1:3, or about 1:3.5. In a preferred embodiment, the compound comprising Formula (VI) is provided in a 1:1 molar ratio with the compound comprising Formula (VII) or Formula (VIII).

In some aspects, the reaction may be conducted under dehydration conditions in the presence of an acid catalyst. In some embodiments, the starting materials are purified to a low water concentration prior to the contacting step. For example, the starting materials comprising the compounds of Formulas (VI) and (VII) or (VIII) may be provided to the reaction mixture with a water content below about 5%, below about 3%, below about 2%, or below about 1%.

A variety of acid catalysts may be suitable to produce the compound comprising Formula (IX). In some embodiments, the acid catalyst may be chosen from organic acids, inorganic acids, and solid resins. Exemplary acid catalysts include, without limitation, phosphoric acid, acetic acid, boric acid, hydrochloric acid, trifluoroacetic acid, methanesulfonic acid, ortho-meta- and para-toluenesulfonic acid, polyphosphoric acid, sulfuric acid, tosylic acid, xylenesulfonic acid, Dowex resins, Amberlyst resins, Zn dust, and Sn based catalysts (such as, for example, Sn dust, tin oxide, tin (II) chloride, dibutyltin dilaurate, and stannous octoate), germanium dioxide, antimony trioxide, zinc oxide, iron (III) oxide, aluminum oxide, silicon dioxide, titanium dioxide, mixtures and combinations thereof.

The acid catalyst may be added in a range of ratios to the compounds comprising Formulas (VI) and (VII) or (VIII). In some aspects the amount of catalyst added may range from 0.0001 mol % of the amount of the compounds comprising Formulas (VI) and (VII) or (VIII) to about 5 mol % of the compounds comprising Formulas (VI) and (VII) or (VIII). In some embodiments, the acid catalyst is added in an amount below 5 mol %, below 2 mol %, or below 1 mol %. More preferably, the acid catalyst is provided in the reaction in a molar ratio of about 0.001, 0.002, 0.003, 0.004, 0.005, 0.006, 0.007, 0.008, 0.009, or 0.010 mol % to the compound comprising Formula (VI).

The reaction may be conducted under dehydration conditions to promote formation of the cyclic dimer. In certain embodiments, dehydration may be accomplished via distillation. For example, the reaction may be subjected to simple distillation, fractional distillation, azeotropic distillation, steam distillation, vacuum distillation, distillation using a Dean Stark trap or another similar trap, azeotropic distillation using a Dean Stark or another similar trap, and the like. In other embodiments, dehydration may be accomplished via a drying reagent which may include molecular sieves, calcium sulfate, magnesium sulfate, sodium sulfate, potassium hydroxide, potassium carbonate, and the like.

The temperature at which the reaction takes place may vary in different embodiments and over the course of the reaction. In one embodiment, the reaction may be carried out at a temperature ranging from about 100° C. and about 200° C. In another embodiment, the reaction may be conducted at a temperature of about 100° C., 110° C., 120° C., 130° C., 140° C., 150° C., 160° C., 170° C., 180° C., 190° C., 200° C., or at a range between and including any two of these values. In another embodiment, the temperature may range from about 130° C. and about 150° C. In yet another embodiment, the temperature may range from about 110° C. and about 120° C. In general, the reaction is conducted at atmospheric pressure, but in certain embodiments, the reaction may also be conducted above or below atmospheric pressure.

The process may be performed in the presence of a solvent or the reaction may be performed neat. Where the reaction includes a solvent, the type of solvent may vary depending upon the identities of the reactants. Thus, the solvent may be a nonpolar solvent, a protic polar solvent, an aprotic polar solvent, or a combination thereof. Non-limiting examples of suitable nonpolar solvents include anisole, benzene, butyl acetate, tert-butyl methyl ether, chlorobenzene, chloroform, chloromethane, cyclohexane, dichloromethane, dichloroethane, di-tert-butyl ether, di methyl ether, diethylene glycol, diethyl ether, diglyme, diisopropyl ether, ethyl tert-butyl ether, ethylene oxide, fluorobenzene, heptane, hexane, methyl tert-butyl ether, toluene, xylene and combinations thereof. Examples of suitable protic polar solvents include without limit water, alcohols (e.g., methanol, ethanol, isopropanol, n-propanol, isobutanol, n-butanol, s-butanol, t-butanol), diols (e.g., propylene glycol and the like), organic acids (e.g., formic acid, acetic acid, and so forth), amides (e.g., formamide, acetamide, and the like), and combinations of any of the above. Non-limiting examples of suitable aprotic polar solvents include acetone, acetonitrile, diethoxymethane, N,N-dimethylformamide (DMF), dimethyl sulfoxide (DMSO), N,N-dimethylpropionamide, 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, N,N-dimethylacetamide (DMAC), N-methyl-2-pyrrolidinone (NMP), 1,4-dioxane, ethyl acetate, ethyl formate, formamide, hexachloroacetone, hexamethylphosphoramide, methyl acetate, N-methylacetamide, methylethyl ketone, methylisobutyl ketone, N-methylformamide, methylene chloride, methoxyethane, morpholine, nitrobenzene, nitromethane, propionitrile, propyl acetates, sulfolane, tetramethylurea, tetrahydrofuran (THF), 2-methyl tetrahydrofuran, tetrahydropyran, trichloromethane, and combinations thereof. In exemplary embodiments, the solvent is chosen from toluene, xylene, anisole, and mixtures thereof.

The weight-to-weight ratio of the solvent to the compounds comprising Formulas (VI) and (VII) or (VIII) can and will vary. Typically, the weight-to-weight ratio of the solvent to the compounds comprising Formulas (VI) and (VII) or (VIII) may range from about 1:1 to about 100:1. In various embodiments, the weight-to-weight ratio of the solvent to the compounds comprising Formulas (VI) and (VII) or (VIII) may range from about 1:1 to 5:1, from about 5:1 to about 20:1, from about 20:1 to about 40:1, from about 40:1 to about 80:1, or from about 80:1 to about 100:1. In some embodiments, the weight-to-weight ratio of the solvent to the compounds comprising Formulas (VI) and (VII) or (VIII) may be about 30:1, or about 60:1.

The duration of the reaction can and will vary. In general, the reaction may be allowed to proceed from several hours to several days. Typically, however, the reaction is allowed to proceed for a sufficient period of time until the reaction is complete, as determined by means well known to those of skill in the art. In this context, the final reaction mixture contains a significantly diminished amount of the compounds comprising Formulas (VI) and (VII) or (VIII) and a significantly increased amount of the compound comprising Formula (IX) compared to the amounts of each present at the beginning of the reaction. In some embodiments, the reaction may be allowed to proceed for a period of time ranging from about 1 hour to about 10 hours. In another embodiment, the reaction may be allowed to proceed for a period of time ranging from about 1 hour to about 5 hours. In a preferred embodiment, the reaction may be allowed to proceed for a period for about 3 hours to about 5 hours.

The yield of the compound comprising Formula (IX) can and will vary. In general, yield of the compound comprising Formula (IX) will be at least about 15%, at least about 20%, 30%, at least about 40%, at least about 50%, at least about 60%, at least about 70%, at least about 80%, or at least about 90%.

The compound comprising Formula (IX) may be isolated from the reaction mixture and/or purified by means including by size exclusion chromatography, high performance liquid chromatography (HPLC), ion-exchange chromatography, chiral chromatography, other types of chromatography, precipitation, distillation, or crystallization.

(b) Preparation of Compounds Comprising Formula (IX)—Polymerization and Thermal Cracking In other embodiments, the compound comprising Formula (IX) may be prepared by (a) heating a compound comprising Formula (VI) with a compound comprising Formula (VII) or a compound comprising Formula (VIII) such that a polymer is formed and then (b) heating the polymer at an increased temperature and reduced pressure to form the cyclic dimer compound comprising Formula (IX). The reactants, i.e., the compounds comprising Formulas (VI), (VII), and (VIII), are described above in section (II)(a).

The first step of this process comprises heating the reactants in the presence or absence of an acid catalyst. Suitable acid catalysts and suitable amounts are detailed above in section (II)(a). In some embodiments, the heating step is performed under a vacuum. The heating step may be performed in the presence of a solvent, as detailed above, or the heating may be performed in the absence of a solvent (i.e., neat). Similar to the method detailed above, the reaction mixture may be heated to and maintained at a temperature ranging from about 100° C. to about 200° C. In exemplary embodiments, the reaction mixture may be heated to about 130° C. to about 160° C. The duration of the heating step may also vary. In some embodiments, the duration of the heating step may range from about 2 hours to about 10 hours, or from about 3 hours to about 5 hours.

The second step of this process comprises additional heating at a higher temperature and under reduced pressure (i.e., thermal cracking). The temperature of the second step may range from about 150° C. to about 250° C. In some embodiments the temperature of the second step may range 150° C. to about 180° C., from about 180° C. to about 200° C., from about 200° C. to about 220° C., or from about 220° C. to about 250° C. In general, the second step is performed under a vacuum. The pressure of the reaction may be less than about 10 Torr, less than about 1 Torr, less than about 500 mTorr, or less than about 200 mTorr. In various embodiments, the pressure of the second step of the reaction may range from about 200 mTorr to about 500 mTorr, or may range from about 0.5 Torr to about 1 Torr. The duration of the second step of the process may range from about 1 hour to about 5 hours. In one embodiment, the duration of the second step of the process may range from about 2 hours to about 3 hours. During the second step of the process, the compound comprising Formula (IX) may be distilled as detailed above in section (II)(a).

The yield of the compound comprising Formula (IX) prepared by the polymerization/thermal cracking process can and will vary depending upon a variety of factors. In various embodiments, the yield of the compound comprising Formula (IX) in distillates from the reaction mixture may be at least about 15%, at least about 20%, at least about 30%, at least about 40%, at least about 50%, at least about 60%, at least about 70%, at least about 80%, at least about 90%, at least about 95%, or at least about 99%.

The compound comprising Formula (IX) may be isolated from the reaction mixture and/or purified by means including by size exclusion chromatography, HPLC, ion-exchange chromatography, chiral chromatography, other types of chromatography, precipitation, distillation, or crystallization.

(c) Preparation of Compounds Comprising Formula (IV)

The method for preparing the compound comprising Formula (IV) comprises contacting a compound comprising Formula (X) and a compound comprising Formula (XI) according to Reaction Scheme 2:

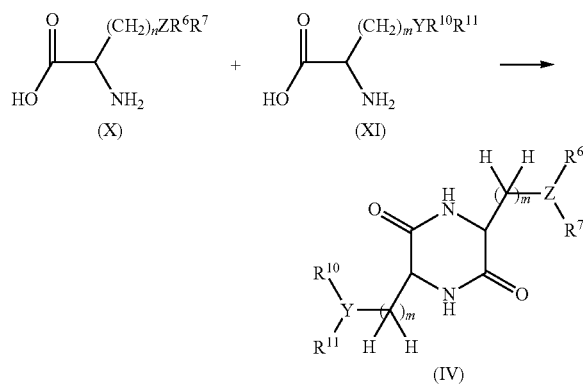

wherein,
$R^6$ and $R^{10}$ are independently chosen from hydrogen, hydrocarbyl, and substituted hydrocarbyl,
$R^7$ and $R^{11}$ are optionally present, when present each is independently chosen from hydrogen, hydrocarbyl, and substituted hydrocarbyl;
Y and Z are independently chosen from sulfone, sulfoxide, and selenium; and
n and m are integers≥1.

In general, the compound comprising Formula (IV) may be produced by subjecting compounds comprising Formulas (X) and (XI) to conditions such that the compounds form a cyclic dimer. $R^6$, $R^7$, $R^{10}$, $R^{11}$, Y, Z, n and m of the compounds comprising Formulas (X), (XI), and (IV) may generally be as set out in Section (I).

The compounds comprising Formulas (X) and (XI) may be provided to the reaction in an approximately equal molar ratio. In some embodiments, the compounds comprising Formulas (X) and (XI) may be provided in a molar ratio of about 0.1:1, 0.2:1, 0.3:1, 0.4:1, 0.5:1, 0.6:1; 0.7:1, 0.8:1, 0.9:1, 1:1.0, 1:1.1, 1:1.2, 1:1.3, 1:1.4, 1:1.5, 1:1.6, 1:1.7, 1:1.8, 1:2.0, 1:2.5, 1:3, or 1:3.5. In a preferred embodiment, the compounds comprising Formulas (X) and (XI) are provided in an equal molar ratio.

A variety of acid catalysts may be used in the reaction. In some embodiments, the acid catalyst may be chosen from organic acids, inorganic acids, and solid resins. Exemplary acid catalysts include, without limitation, acetic acid, hydrochloric acid, trifluoroacetic acid, methanesulfonic acid, ortho-meta- and para-toluenesulfonic acid, sulfuric acid, phosphoric acid, xylenesulfonic acid, Dowex resins, Amberlyst resins, Zn dust, and Sn dust.

The acid catalyst may be added in a range of ratios to the compounds comprising Formulas (X) and (XI). In some aspects the amount of catalyst added ranges from about 0.0001 mol % of the amount of the compounds comprising Formulas (X) and (XI) to about 5 mol % of the compounds comprising Formulas (X) and (XI). In some embodiments, the acid catalyst may be added in an amount below 5 mol %, below 2 mol %, or below 1 mol %. More preferably, the acid catalyst may be provided in the reaction in a molar ratio of about 0.001, 0.002, 0.003, 0.004, 0.005, 0.006, 0.007, 0.008, 0.009, or 0.010 mol % to the compounds comprising Formulas (X) and (XI).

The temperature at which the reaction takes place may vary in different embodiments and/or over the course of the reaction. In some aspects, the reaction may be conducted at a temperature of 100° C., 110° C., 120° C., 130° C., 140° C., 150° C., 160° C., 170° C., 180° C., 190° C., 200° C., or at a range between and including any two of these values. In one embodiment, the reaction may be carried out at a temperature ranging from about 100° C. and about 200° C. In another embodiment, the temperature may range from about 130° C. and about 150° C. In general, the reaction is conducted at atmospheric pressure, but in certain embodiments, the reaction may also be conducted above or below atmospheric pressure.

The process may be performed in the presence of a solvent, while in other aspects the reaction may be performed neat. Where a solvent is present, the solvent may be chosen, by way of non-limiting example, from the solvents listed in section (II)(a). In one embodiment, the solvent is chosen from toluene, xylene, anisole, and mixtures thereof.

The weight-to-weight ratio of the solvent to the compounds comprising Formulas (X) and (XI) can and will vary. Typically, the weight-to-weight ratio of the solvent to the compounds comprising Formulas (X) and (XI) may range from about 1:1 to about 100:1. In various embodiments, the weight-to-weight ratio of the solvent to the compounds comprising Formulas (X) and (XI) may range from about 1:1 to 5:1, from about 5:1 to about 20:1, from about 20:1 to about 40:1, from about 40:1 to about 80:1, or from about 80:1 to about 100:1

The duration of the reaction can and will vary. In general, the reaction may be allowed to proceed from several hours to several days. Typically, however, the reaction is allowed to proceed for a sufficient period of time until the reaction is complete, as determined by means well known to those of skill in the art. In this context, the final reaction mixture contains a significantly diminished amount of the compounds comprising Formulas (X) and (XI) and a significantly increased amount of the compound comprising Formula (IV) compared to the amounts of each present at the beginning of the reaction. In some embodiments, the reaction may be allowed to proceed for a period of time ranging from about 1 hour to about 10 hours.

The yield of the compound comprising Formula (IV) can and will vary. In general, yield of the compound comprising Formula (IV) will be at least about 15%, at least about 20%, 30%, at least about 40%, at least about 50%, at least about 60%, at least about 70%, at least about 80%, or at least about 90%.

(d) Preparation of the Compound Comprising Formula (V)

In one embodiment, a process for producing the compound comprising Formula (V) is provided, which proceeds according to Reaction Scheme 3:

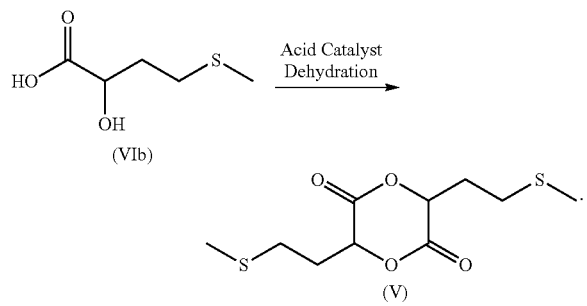

In exemplary embodiments, the acid catalyst is p-toluenesulfonic acid. The compound comprising Formula (VIb) is heated to 110-115° C. in the presence of the acid catalyst in toluene for 3-5 hours with continuous removal of water using a Dean Stark trap.

In some embodiments, the process provides the compound comprising Formula (V) as a racemic mixture comprising stereoisomers of the compound comprising Formula (V) (i.e., D-, L-, and meso isomers; see compounds 2, 3, and 4, respectively, in Table 5). The racemic mixture may be separated into individual diastereomers of the compound comprising Formula (V). In some embodiments, the D-, and L-isomers may be first separated from the meso isomer by methods known in the art including, but not limited to, recrystallization, distillation, and chromatography. The D- and L-isomers may then be separated by means known in the art including, but not limited to, chiral chromatography, recrystallization, and distillation. In other embodiments, the D-, L-, and meso isomers may be separated by chiral chromatography (see Example 4).

(III) Applications

The cyclic dimer compounds detailed above in section (I) may be used in a variety of applications. Suitable applications include, without limit, use as plasticizers, emulsifiers, additives, processing aids, nutritive agents, antioxidant agents, antimicrobial agents, anticorrosive agents, and feed additives.

In some embodiments, the cyclic dimer compounds may be used as a source of alpha acids. In some embodiments, the compounds disclosed herein may be used as feed additives or included in feed compositions or feed premixes. In other embodiments, the compounds described above in section (I) may be part of a composition comprising at least one nutritive and/or pharmaceutical agent.

The compositions comprising the cyclic dimer compounds may be administered to human or animal subjects. Non-limiting examples of suitable animal subjects include companion animals such as cats, dogs, rabbits, horses, and rodents such as gerbils; agricultural animals such as cows, dairy cows, dairy calves, beef cattle, pigs, goats, sheep, horses, deer; zoo animals such as primates, elephants, zebras, large cats, bears, and the like; research animals such as rabbits, sheep, pigs, dogs, primates, mice, rats and other rodents; avians, including but not limited to chickens, ducks, turkeys, ostrich, and emu; and aquatic animals chosen from fish and crustaceans including, but not limited to, salmon, shrimp, carp, tilapia, and shell fish. The subject may be monogastric or a ruminant. When the subject is a ruminant the compounds described in section (I) may remain substantially intact in the rumen such that the compound is not broken down in the rumen. Thus, the feed composition may have an increased digestional efficiency for ruminant subjects. In some aspects, the compounds described in section (I) remain substantially intact in the rumen. In other aspects, the compounds described in section (I) may hydrolyze after passage through the rumen.

(IV) Compositions Comprising Cyclic Dimers

In yet another aspect, the present invention provides compositions comprising at least one cyclic dimer compound detailed above in section (I). The compositions may further comprise at least one nutritive and/or pharmaceutical agent.

(a) Feed Compositions

In some embodiments, the composition may be a feed composition or a feed premix. The feed composition comprises one or more of the compounds described in section (I) and at least one nutritive agent. The nutritive agent may be a hydrolysis product of the cyclic dimer. The compounds described in section (I) may hydrolyze after passage from through the stomach or rumen of a subject. For example, the compounds in section (I) may hydrolyze under conditions where the compounds are subjected to a pH of about 4.5, 4.0, 3.5, 3.0, 2.5, 2.0, 1.5, 1.0, or 0.5, or any pH between and including the listed values. A substantially hydrolyzed composition, as used herein, refers to a solution where greater than 50% of the compounds in section (I) of the composition are in a noncyclical form. In some embodiments, substantially hydrolyzed refers to greater than 60%, or greater than 70%, or greater than 80%, or greater than 90% hydrolyzed.

In other embodiments, the nutritive agent may be a carbohydrate source, a fat source, a protein source, an amino acid, and alpha hydroxy acid, or combinations thereof. Suitable carbohydrate sources may be chosen from those known in the art and include, without limitation, alginate, arrowroot, barley, canola, cassava, corn, corn syrup, cottonseed meal, fructose, glucose, galactose, grain sorghum, kelp meal, lactose, maize, maltose, mannose, potatoes, oats, rice, rye, sago, sorbitol, soybeans, tapioca, wheat, wheat gluten, yam, and combinations thereof.

The fat source may be an inert fat or a non-inert fat. Non-limiting examples of non-inert fats include plant derived oils (e.g., canola oil, corn oil, cottonseed oil, palm oil, peanut oil, safflower oil, soybean oil, and sunflower oil), fish oils (e.g., menhaden oil, anchovy oil, albacore tuna oil, cod liver oil, herring oil, lake trout oil, mackerel oil, salmon oil, and sardine oil), animal fats (e.g., poultry fat, beef tallow, butter, pork lard, and whale blubber), yellow grease (i.e., waste grease from restaurants and low-grade fats from rendering plants), and combinations thereof. The non-inert fat source may also be a high fat product such as fish meal (e.g., menhaden meal, anchovy meal, herring meal, pollack meal, salmon meal, tuna meal, and whitefish meal), oilseeds (e.g., canola seeds, cottonseeds, flax seeds, linseeds, Niger seeds, sesame seeds, soy beans, and sunflower seeds), or distillers grains (e.g., dried distillers grains and solubles (DDGS) and wet distillers grains). The fat source may be a ruminally inert fat. Suitable examples of ruminally inert fats include calcium salts of palm fatty acids (e.g., MEGA-LAC®), saturated free fatty acids, or hydrogenated tallow (e.g., ALIFET®).

Suitable protein sources may be animal-derived proteins, plant-derived proteins, or combinations thereof. In some embodiments, suitable sources of animal derived protein include blood meal, bone meal, fish meal, fish processing by-products, meat meal, meat and bone meal, poultry by-produce meal, feather meal, and combinations thereof. In other embodiments, suitable sources of plant-derived proteins include grains such as corn, oats, soybean, and the like; grain protein concentrates such as soy protein concentrate; legumes such as peas, lupine, alfalfa; distiller's grains; oilseed meals such as canola meal, cottonseed meal, flaxseed meal, soybean meal, sunflower seed meal; and combinations thereof.

In some embodiments, the feed composition/premix may include one or more alpha acids including amino acids and alpha hydroxy acids. Suitable examples of amino acids, depending upon the formulation, include alanine, arginine, asparagines, aspartate, cysteine, glutamate, glutamine, glycine, histidine, isoleucine, leucine, lysine, methionine, selenomethionine, phenylalanine, proline, serine, threonine, tryptophan, tyrosine, and valine. Other amino acids usable as feed additives include, by way of non-limiting example, N-acylamino acids, hydroxy homologue compounds, and physiologically acceptable salts thereof, such as hydrochlorides, hydrosulfates, ammonium salts, potassium salts, calcium salts, magnesium salts and sodium salts of amino acids. The feed compositions may further include an alpha hydroxy acid. In some aspects the alpha hydroxy acids are alpha hydroxy analogs of amino acids. In one aspect, the alpha acid is the hydroxy analog of methionine.

The feed composition may be formulated as a liquid, an emulsion, dry pellets, or a powder, and may be mixed with various other ingredients.

(b) Combinations with Nutritive and/or Pharmaceutical Agents

In other embodiments, the composition comprises at least one compound detailed in section (I) in combination with at least one nutritive and/or pharmaceutical agent. Nutritive agents may comprise any agent that provides nutritive value when administered to a subject. Non-limiting examples of nutritive agents include vitamins, minerals (e.g., organic or inorganic), antioxidants, organic acids, poly unsaturated fatty acids ("PUFA"), prebiotics, probiotics, herbs, and pigments.

Suitable vitamins include vitamin C, vitamin A, vitamin E, vitamin B12, vitamin K, riboflavin, niacin, vitamin D, vitamin B6, folic acid, pyridoxine, thiamine, pantothenic acid, and biotin. The form of the vitamin may include salts of the vitamin, derivatives of the vitamin, compounds having the same or similar activity of a vitamin, and metabolites of a vitamin.

Suitable organic trace mineral may comprise a metal chelate comprising metal ions and an amino acid ligand. Alternatively, the organic trace mineral may be a metal salt comprising metal ions and an amino acid anion. The metal ions may be selected from the group consisting of zinc ions, copper ions, manganese ions, iron ions, chromium ions, cobalt ions, magnesium ions, calcium ions, and combinations thereof. In a preferred embodiment, the metal ions are zinc ions, manganese ions, and copper ions. The amino acids may be selected from the group comprising alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine, or their hydroxy analogs. In certain embodiments, the copper and zinc ions are preferably divalent, i.e., each ion carries a charge of $2^+$. The molar ratio of amino acids to metal ions in the chelate molecule may generally vary from 1:1 to 3:1 or higher. Typically, a metal chelate may comprise a mixture of 1:1, 2:1 and 3:1 species. Preferably, the molar ratio of amino acids to metal ion in the chelate molecule may generally vary from 1.5:1 to 2.5:1. In an aqueous medium, the relative proportions of these species are determined by the applicable stability constants. Where the number of ligands equates to the charge on the metal ion, the charge is typically balanced because the carboxyl moieties of the amino acids are in deprotonated form. For example, in the chelate species wherein the metal cation carries a charge of 2+ and the amino acid to metal ratio is 2:1, each of the hydroxy or amino groups is understood to be bound by a coordinate covalent bond to the metal ion. Where the number of ligands exceeds the charge on the metal ion, e.g., in a 3:1 chelate of a divalent metal ion, the amino acids in excess of the charge typically may remain in a protonated state to balance the charge. On the other hand, where the positive charge on the metal ion exceeds the number of amino acids, the charge may be balanced by the presence of another anion such as, for example, chloride, bromide, iodide, bicarbonate, hydrogen sulfate, di hydrogen phosphate and combinations thereof. Divalent anions may also be present. In an exemplary embodiment, the metal chelate comprises 2-hydroxy-4-methylthiobutanoic acid.

The mineral may also be an inorganic trace mineral. Suitable inorganic trace minerals include, for example, metal sulfates, metal oxides, metal carbonates, and metal halides. By way of non-limiting example, the inorganic trace mineral may be copper sulfate, copper oxide, copper chloride, or copper carbonate. Alternatively, the inorganic trace mineral may be manganese sulfate, manganese chloride, or manganous oxide. In another embodiment, the inorganic trace mineral may be zinc sulfate, zinc oxide, zinc chloride, or zinc carbonate. In yet an additional embodiment, the inorganic trace mineral may be sodium selenite or sodium selenate.

Suitable antioxidants include, but are not limited to, ascorbic acid and its salts, ascorbyl palmitate, ascorbyl stearate, anoxomer, n-acetylcysteine, benzyl isothiocyanate, m-aminobenzoic acid, o-aminobenzoic acid, p-aminobenzoic acid (PABA), butylated hydroxyanisole (BHA), butylated hydroxytoluene (BHT), caffeic acid, canthaxantin, alpha-carotene, beta-carotene, beta-caraotene, beta-apocarotenoic acid, carnosol, carvacrol, catechins, cetyl gallate, chlorogenic acid, citric acid and its salts, clove extract, coffee bean extract, p-coumaric acid, 3,4-dihydroxybenzoic acid, N,N'-diphenyl-p-phenylenediamine (DPPD), dilauryl thiodipropionate, distearyl thiodipropionate, 2,6-di-tert-butylphenol, dodecyl gallate, edetic acid, ellagic acid, erythorbic acid, sodium erythorbate, esculetin, esculin, 6-ethoxy-1,2-dihydro-2,2,4-trimethylquinoline (ethoxyquin), ethyl gallate, ethyl maltol, ethylenediaminetetraacetic acid (EDTA), eucalyptus extract, eugenol, ferulic acid, flavonoids (e.g., catechin, epicatechin, epicatechin gallate, epigallocatechin (EGC), epigallocatechin gallate (EGCG), polyphenol epigallocatechin-3-gallate, flavones (e.g., apigenin, chrysin, luteolin), flavonols (e.g., datiscetin, myricetin, daemfero), flavanones, fraxetin, fumaric acid, gallic acid, gentian extract, gluconic acid, glycine, gum guaiacum, hesperetin, alpha-hydroxybenzyl phosphinic acid, hydroxycinammic acid, hydroxyglutaric acid, hydroquinone, n-hydroxysuccinic acid, hydroxytryrosol, hydroxyurea, rice bran extract, lactic acid and its salts, lecithin, lecithin citrate; R-alpha-lipoic acid, lutein, lycopene, malic acid, maltol, 5-methoxy tryptamine, methyl gallate, monoglyceride citrate; monoisopropyl citrate; morin, beta-naphthoflavone, nordihydroguaiaretic acid (NDGA), octyl gallate, oxalic acid, palmityl citrate, phenothiazine, phosphatidylcholine, phosphoric acid, phosphates, phytic acid, phytylubichromel, pimento extract, propyl gallate, polyphosphates, quercetin, trans-resveratrol, rosemary extract, rosmarinic acid, sage extract, sesamol, silymarin, sinapic acid, succinic acid, stearyl citrate, syringic acid, tartaric acid, thymol, tocopherols (i.e., alpha-, beta-, gamma- and delta-tocopherol), tocotrienols (i.e., alpha-, beta-, gamma- and delta-tocotrienols), tyrosol, vanilic acid, 2,6-di-tert-butyl-4-hydroxymethylphenol (i.e., Ionox 100), 2,4-(tris-3',5'-bi-tert-butyl-4'-hydroxybenzyl)-mesitylene (i.e., Ionox 330), 2,4,5-trihydroxybutyrophenone, ubiquinone, tertiary butyl hydroquinone (TBHQ), thiodipropionic acid, trihydroxy butyrophenone, tryptamine, tyramine, uric acid, vitamin K and derivates, vitamin Q10, wheat germ oil, zeaxanthin, or combinations thereof.

A variety of organic acids comprised of carboxylic acids are suitable. In one embodiment, the organic acid may contain from about one to about twenty-five carbon atoms. In another embodiment, the organic acid may have from about three to about twenty-two carbon atoms. In a further embodiment, the organic acid may contain from about three to about twelve carbon atoms. In yet another embodiment, the organic acid may contain from about eight to about twelve carbon atoms. In still another embodiment, the organic acid may contain from about two to about six carbon atoms. Suitable organic acids, by way of non-limiting example, include formic acid, acetic acid, propionic acid, butanoic acid, benzoic acid, lactic acid, malic acid, tartaric acid, mandelic acid, citric acid, fumaric acid, sorbic acid, boric acid, succinic acid, adipic acid, glycolic acid, cinnamaldehyde, and glutaric acid.

Salts of organic acids comprising carboxylic acids are also suitable for certain embodiments. Representative suitable salts include the ammonium, magnesium, calcium, lithium, sodium, potassium, selenium, iron, copper, and zinc salts of organic acids. In one embodiment, the organic acid is an ammonium, magnesium, calcium, lithium, sodium, potassium, selenium, iron, copper, or zinc salt of formic acid. In another embodiment, the organic acid is an ammonium, magnesium, calcium, lithium, sodium, potassium, selenium, iron, copper, or zinc salt of acetic acid. In yet another embodiment, the organic acid is an ammonium, magnesium, calcium, lithium, sodium, potassium, selenium, iron, copper, or zinc salt of propionic acid. In an additional embodiment, the organic acid is an ammonium, magnesium, calcium, lithium, sodium, potassium, selenium, iron, copper, or zinc salt of butanoic acid. In a further embodiment, the organic acid is an ammonium, magnesium, calcium, lithium, sodium, potassium, selenium, iron, copper, or zinc salt of benzoic acid. In still another embodiment, the organic acid is an ammonium, magnesium, calcium, lithium, sodium, potassium, selenium, iron, copper, or zinc salt of lactic acid. In yet another embodiment, the organic acid is an ammonium, magnesium, calcium, lithium, sodium, potassium, selenium, iron, copper, or zinc salt of malic acid. In still another embodiment, the organic acid is an ammonium, magnesium, calcium, lithium, sodium, potassium, selenium, iron, copper, or zinc salt of tartaric acid. In a further embodiment, the organic acid is an ammonium, magnesium, calcium, lithium, sodium, potassium, selenium, iron, copper, or zinc salt of mandelic acid. In yet another embodiment, the organic acid is an ammonium, magnesium, calcium, lithium, sodium, potassium, selenium, iron, copper, or zinc salt of citric acid. In an additional embodiment, the organic acid is an ammonium, magnesium, calcium, lithium, sodium, potassium, selenium, iron, copper, or zinc salt of fumaric acid. In an additional embodiment, the organic acid is an ammonium, magnesium, calcium, lithium, sodium, potassium, selenium, iron, copper, or zinc salt of sorbic acid. In another embodiment, the organic acid is an ammonium, magnesium, calcium, lithium, sodium, potassium, selenium, iron, copper, or zinc salt of boric acid. In yet another embodiment, the organic acid is an ammonium, magnesium, calcium, lithium, sodium, potassium, selenium, iron, copper, or zinc salt of succinic acid. In another embodiment, the organic acid is an ammonium, magnesium, calcium, lithium, sodium, potassium, selenium, iron, copper, or zinc salt of adipic acid. In yet another embodiment, the organic acid is an ammonium, magnesium, calcium, lithium, sodium, potassium, selenium, iron, copper, or zinc salt of glycolic acid. In an additional embodiment, the organic acid is an ammonium, magnesium, calcium, lithium, sodium, potassium, selenium, iron, copper, or zinc salt of glutaric acid.

Alternatively, the organic acid may be comprised of a substituted carboxylic acid. A substituted carboxylic acid generally has the same features as those detailed above for carboxylic acids, but the hydrocarbyl chain has been modified such that it is branched, is part of a ring structure, or contains some other substitution. In one embodiment, the substituted carboxylic acid may contain one or more additional carboxyl groups. Saturated dicarboxylic acids include malonic acid, succinic acid, glutaric acid, and adipic acid, and unsaturated dicarboxylic acids include maleic acid and fumaric acid. In another embodiment, the substituted carboxylic acid may contain one or more hydroxy groups. A substituted carboxylic acid with a hydroxy group on the alpha carbon, i.e., the carbon adjacent to the carboxyl carbon, is generally called a α-hydroxy carboxylic acid. Examples of suitable α-hydroxy carboxylic acids include glycolic acid, lactic acid, malic acid, and tartaric acid. In an alternate embodiment, the substituted carboxylic acid may contain one or more carbonyl groups. In yet another embodiment, the substituted carboxylic acid may contain an amino group on the alpha carbon, i.e., is an α-amino acid. In one embodiment, the α-amino acid may be one of the twenty standard amino acids or derivatives thereof. In another embodiment, the α-amino acid may be an essential α-amino acid selected from the group consisting of arginine, histidine, isoleucine, leucine, lysine, methionine, phenylalanine, threonine, tryptophan, and valine. Salts of organic acids comprising substituted carboxylic acids are also suitable for certain embodiments. Representative suitable salts include the ammonium, magnesium, calcium, lithium, sodium, potassium, selenium, iron, copper, and zinc salts of organic acids comprising substituted carboxylic acids.

Suitable PUFAs include a long chain fatty acid with at least 18 carbon atoms and at least two carbon-carbon double bonds, generally in the cis-configuration. In an exemplary embodiment, the PUFA is an omega fatty acid. The PUFA may be an omega-3 fatty acid in which the first double bond occurs in the third carbon-carbon bond from the methyl end of the carbon chain (i.e., opposite the carboxyl acid group). Suitable examples of omega-3 fatty acids include all-cis 7,10,13-hexadecatrienoic acid; all-cis-9,12,15-octadecatrienoic acid (alpha-linolenic acid, ALA); all-cis-6,9,12,15,-octadecatetraenoic acid (stearidonic acid); all-cis-8,11,14, 17-eicosatetraenoic acid (eicosatetraenoic acid); all-cis-5,8, 11,14,17-eicosapentaenoic acid (eicosapentaenoic acid, EPA); all-cis-7,10,13,16,19-docosapentaenoic acid (clupanodonic acid, DPA); all-cis-4,7,10,13,16,19-docosahexaenoic acid (docosahexaenoic acid, DHA); all-cis-4,7,10,13,16,19-docosahexaenoic acid; and all-cis-6,9,12,15,18,21-tetracosenoic acid (nisinic acid). In an alternative embodiment, the PUFA may be an omega-6 fatty acid in which the first double bond occurs in the sixth carbon-carbon bond from the methyl end of the carbon chain. Examples of omega-6 fatty acids include all-cis-9,12-octadecadienoic acid (linoleic acid); all-cis-6,9,12-octadecatrienoic acid (gamma-linolenic acid, GLA); all-cis-11,14-eicosadienoic acid (eicosadienoic acid); all-cis-8,11,14-eicosatrienoic acid (di homo-gamma-linolenic acid, DGLA); all-cis-5,8,11,14-eicosatetraenoic acid (arachidonic acid, AA); all-cis-13,16-docosadienoic acid (docosadienoic acid); all-cis-7,10,13,16-docosatetraenoic acid (adrenic acid); and all-cis-4,7,10,13, 16-docosapentaenoic acid (docosapentaenoic acid). In yet another alternative embodiment, the PUFA may be an omega-9 fatty acid in which the first double bond occurs in the ninth carbon-carbon bond from the methyl end of the carbon chain, or a conjugated fatty acid, in which at least one pair of double bonds are separated by only one single bond. Suitable examples of omega-9 fatty acids include cis-9-octadecenoic acid (oleic acid); cis-11-eicosenoic acid (eicosenoic acid); all-cis-5,8,11-eicosatrienoic acid (mead acid); cis-13-docosenoic acid (erucic acid), and cis-15-tetracosenoic acid (nervonic acid). Examples of conjugated fatty acids include 9Z,11E-octadeca-9,11-dienoic acid (rumenic acid); 10E,12Z-octadeca-9,11-dienoic acid; 8E,10E, 12Z-octadecatrienoic acid (α-calendic acid); 8E,10E,12E-octadecatrienoic acid (β-Calendic acid); 8E,10Z,12E-octadecatrienoic acid (jacaric acid); 9E,11E,13Z-octadeca-9,11,13-trienoic acid (α-eleostearic acid); 9E,11E,13E-octadeca-9,11,13-trienoic acid (β-eleostearic acid); 9Z,11Z, 13E-octadeca-9,11,13-trienoic acid (catalpic acid), and 9E,11Z,13E-octadeca-9,11,13-trienoic acid (punicic acid).

Probiotics and prebiotics may include yeast and bacteria that help establish an immune protective rumen or gut microflora as well as small oligosaccharides. By way of non-limiting example, yeast-derived probiotics and prebiotics include yeast cell wall derived components such as β-glucans, arabinoxylan isomaltose, agarooligosaccharides, lactosucrose, cyclodextrins, lactose, fructooligosaccharides, laminariheptaose, lactulose, β-galactooligosaccharides, mannanoligosaccharides, raffinose, stachyose, oligofructose, glucosyl sucrose, sucrose thermal oligosaccharide, isomalturose, caramel, inulin, and xylooligosaccharides. In an exemplary embodiment, the yeast-derived agent may be β-glucans and/or mannanoligosaccharides. Sources for yeast cell wall derived components include *Saccharomyces bisporus, Saccharomyces boulardii, Saccharomyces cerevisiae, Saccharomyces capsularis, Saccharomyces delbrueckii, Saccharomyces fermentati, Saccharomyces lugwigii, Saccharomyces microellipsoides, Saccharomyces pastorianus, Saccharomyces rosei, Candida albicans, Candida cloaceae, Candida tropicalis, Candida utilis, Geotrichum candidum, Hansenula americana, Hansenula anomala, Hansenula wingei,* and *Aspergillus oryzae.*

Probiotics and prebiotics may also include bacteria cell wall derived agents such as peptidoglycan and other components derived from gram-positive bacteria with a high content of peptidoglycan. Exemplary gram-positive bacteria include *Lactobacillus acidophilus, Bifedobact thermophilum, Bifedobat longhum, Streptococcus faecium, Bacillus pumilus, Bacillus subtilis, Bacillus licheniformis, Lactobacillus acidophilus, Lactobacillus casei, Enterococcus faecium, Bifidobacterium bifidium, Propionibacterium acidipropionici, Propionibacteriium freudenreichii,* and *Bifidobacterium pscudolongum.*

Suitable herbals and herbal derivatives, as used herein, refer to herbal extracts, and substances derived from plants and plant parts, such as leaves, flowers and roots, without limitation. Non-limiting exemplary herbals and herbal derivatives include agrimony, alfalfa, aloe vera, amaranth, angelica, anise, barberry, basil, bayberry, bee pollen, birch, bistort, blackberry, black cohosh, black walnut, blessed thistle, blue cohosh, blue vervain, boneset, borage, buchu, buckthorn, bugleweed, burdock, capsicum, cayenne, caraway, cascara sagrada, catnip, celery, centaury, chamomile, chaparral, chickweed, chicory, chinchona, cloves, coltsfoot, comfrey, cornsilk, couch grass, cramp bark, culver's root, cyani, cornflower, damiana, dandelion, devils claw, dong quai, echinacea, elecampane, ephedra, eucalyptus, evening primrose, eyebright, false unicorn, fennel, fenugreek, figwort, flaxseed, garlic, gentian, ginger, ginseng, golden seal, gotu kola, gum weed, hawthorn, hops, horehound, horseradish, horsetail, hoshouwu, hydrangea, hyssop, iceland moss, irish moss, jojoba, juniper, kelp, lady's slipper, lemon grass, licorice, lobelia, mandrake, marigold, marjoram, marshmallow, mistletoe, mullein, mustard, myrrh, nettle, oatstraw, oregon grape, papaya, parsley, passion flower, peach, pennyroyal, peppermint, periwinkle, plantain, pleurisy root, pokeweed, prickly ash, psyllium, quassia, queen of the meadow, red clover, red raspberry, redmond clay, rhubarb, rose hips, rosemary, rue, safflower, saffron, sage, St. John's wort, sarsaparilla, sassafras, saw palmetto, scullcap, senega, senna, shepherd's purse, slippery elm, spearmint, spikenard, squawvine, stillingia, strawberry, taheebo, thyme, uva ursi, valerian, violet, watercress, white oak bark, white pine bark, wild cherry, wild lettuce, wild yam, willow, wintergreen, witch hazel, wood betony, wormwood, yarrow, yellow dock, yerba santa, yucca and combinations thereof.

Suitable non-limiting pigments include actinioerythrin, alizarin, alloxanthin, β-apo-2'-carotenal, apo-2-lycopenal, apo-6'-lycopenal, astacein, astaxanthin, azafrinaldehyde, aacterioruberin, aixin, α-carotine, β-carotine, γ-carotine, β-carotenone, canthaxanthin, capsanthin, capsorubin, citranaxanthin, citroxanthin, crocetin, crocetinsemialdehyde, crocin, crustaxanthin, cryptocapsin, α-cryptoxanthin, β-cryptoxanthin, cryptomonaxanthin, cynthiaxanthin, decaprenoxanthin, dehydroadonirubin, diadinoxanthin, 1,4-diamino-2,3-dihydroanthraquinone, 1,4-dihydroxyanthraquinone, 2,2'-Diketospirilloxanthin, eschscholtzxanthin, eschscholtzxanthone, flexixanthin, foliachrome, fucoxanthin, gazaniaxanthin, hexahydrolycopene, hopkinsiaxanthin, hydroxyspheriodenone, isofucoxanthin, loroxanthin, lutein, luteoxanthin, lycopene, lycopersene, lycoxanthin, morindone, mutatoxanthin, neochrome, neoxanthin, nonaprenoxanthin, OH-Chlorobactene, okenone, oscillaxanthin, paracentrone, pectenolone, pectenoxanthin, peridinin, phleixanthophyll, phoeniconone, phoenicopterone, phoenicoxanthin, physalien, phytofluene, pyrrhoxanthininol, quinones, rhodopin, rhodopinal, rhodopinol, rhodovibrin, rhodoxanthin, rubixanthone, saproxanthin, semi-α-carotenone, semi-β-carotenone, sintaxanthin, siphonaxanthin, siphonein, spheroidene, tangeraxanthin, torularhodin, torularhodin methyl ester, torularhodinaldehyde, torulene, 1,2,4-trihydroxyanthraquinone, triphasiaxanthin, trollichrome, vaucheriaxanthin, violaxanthin, wamingone, xanthin, zeaxanthin, α-zeacarotene and combinations thereof.

Suitable non-limiting pharmaceutically acceptable agents include an acid/alkaline-labile drug, a pH dependent drug, or a drug that is a weak acid or a weak base. Examples of acid-labile drugs include statins (e.g., pravastatin, fluvastatin and atorvastatin), antiobiotics (e.g., penicillin G, ampicillin, streptomycin, erythromycin, clarithromycin and azithromycin), nucleoside analogs [e.g., dideoxyinosine (ddI or didanosine), dideoxyadenosine (ddA), dideoxycytosine (ddC)], salicylates (e.g., aspirin), digoxin, bupropion, pancreatin, midazolam, and methadone. Drugs that are only soluble at acid pH include nifedipine, emonapride, nicardipine, amosulalol, noscapine, propafenone, quinine, dipyridamole, josamycin, dilevalol, labetalol, enisoprost, and metronidazole. Drugs that are weak acids include phenobarbital, phenytoin, zidovudine (AZT), salicylates (e.g., aspirin), propionic acid compounds (e.g., ibuprofen), indole derivatives (e.g., indomethacin), fenamate compounds (e.g., meclofenamic acid), pyrrolealkanoic acid compounds (e.g., tolmetin), cephalosporins (e.g., cephalothin, cephalaxin, cefazolin, cephradine, cephapirin, cefamandole, and cefoxitin), 6-fluoroquinolones, and prostaglandins. Drugs that are weak bases include adrenergic agents (e.g., ephedrine, desoxyephedrine, phenylephrine, epinephrine, salbutamol, and terbutaline), cholinergic agents (e.g., physostigmine and neostigmine), antispasmodic agents (e.g., atropine, methantheline, and papaverine), curariform agents (e.g., chlorisondamine), tranquilizers and muscle relaxants (e.g., fluphenazine, thioridazine, trifluoperazine, chlorpromazine, and triflupromazine), antidepressants (e.g., amitriptyline and nortriptyline), antihistamines (e.g., diphenhydramine, chlorpheniramine, dimenhydrinate, tripelennamine, perphenazine, chlorprophenazine, and chlorprophenpyridamine), cardioactive agents (e.g., verapamil, diltiazem, gallapomil, cinnarizine, propranolol, metoprolol and nadolol), antimalarials (e.g., chloroquine), analgesics (e.g., propoxyphene and meperidine), antifungal agents (e.g., ketoconazole and itraconazole), antimicrobial agents (e.g., cefpodoxime, proxetil, and enoxacin), caffeine, theophylline, and morphine. In another embodiment, the drug may be a biphosphonate or another drug used to treat osteoporosis. Non-limiting examples of a biphosphonate include alendronate, ibandronate, risedronate, zoledronate, pamidronate, neridronate, olpadronate, etidronate, clodronate, and tiludronate. Other suitable drugs include estrogen, selective estrogen receptor modulators (SERMs), and parathyroid hormone (PTH) drugs. In yet another embodiment, the drug may be an antibacterial agent. Suitable antibiotics include aminoglycosides (e.g., amikacin, gentamicin, kanamycin, neomycin, netilmicin, streptomycin, and tobramycin), carbecephems (e.g., loracarbef) a carbapenem (e.g., certapenem, imipenem, and meropenem), cephalosporins (e.g., cefadroxil cefazolin, cephalexin, cefaclor, cefamandole, cephalexin, cefoxitin, cefprozil, cefuroxime, cefixime, cefdinir, cefditoren, cefoperazone, cefotaxime, cefpodoxime, ceftazidime, ceftibuten, ceftizoxime, and ceftriaxone), macrolides (e.g., azithromycin, clarithromycin, dirithromycin, erythromycin, and troleandomycin), monobactam, penicillins (e.g., amoxicillin, ampicillin, carbenicillin, cloxacillin, dicloxacillin, nafcillin, oxacillin, penicillin G, penicillin V, piperacillin, and ticarcillin), polypeptides (e.g., bacitracin, colistin, and polymyxin B), quinolones (e.g., ciprofloxacin, enoxacin, gatifloxacin, levofloxacin, lomefloxacin, moxifloxacin, norfloxacin, ofloxacin, and trovafloxacin), sulfonamides (e.g., mafenide, sulfacetamide, sulfamethizole, sulfasalazine, sulfisoxazole, and trimethoprim-sulfamethoxazole), and tetracyclines (e.g., demeclocycline, doxycycline, minocycline, and oxytetracycline). In an alternate embodiment, the drug may be an antiviral protease inhibitor (e.g., amprenavir, fosamprenavir, indinavir, lopinavir/ritonavir, ritonavir, saquinavir, and nelfinavir). In a still another embodiment, the drug may be a cardiovascular drug. Examples of suitable cardiovascular agents include cardiotonic agents (e.g., digitalis (digoxin), ubidecarenone, and dopamine), vasodilating agents (e.g., nitroglycerin, captopril, dihydralazine, diltiazem, and isosorbide dinitrate), antihypertensive agents (e.g., alpha-methyldopa, chlortalidone, reserpine, syrosingopine, rescinnamine, prazosin, phentolamine, felodipine, propanolol, pindolol, labetalol, clonidine, captopril, enalapril, and lisonopril), beta blockers (e.g., levobunolol, pindolol, timolol maleate, bisoprolol, carvedilol, and butoxamine), alpha blockers (e.g., doxazosin, prazosin, phenoxybenzamine, phentolamine, tamsulosin, alfuzosin, and terazosin), calcium channel blockers (e.g., amlodipine, felodipine, nicardipine, nifedipine, nimodipine, nisoldipine, nitrendipine, lacidipine, lercanidipine, verapamil, gallopamil, and diltiazem), and anticlot agents (e.g., dipyrimadole).

A variety of commonly used excipients in pharmaceutical and nutritive formulations may be utilized with any such agents described above. Non-limiting examples of suitable excipients include an agent selected from the group consisting of non-effervescent disintegrants, a coloring agent, a flavor-modifying agent, an oral dispersing agent, a stabilizer, a preservative, a diluent, a compaction agent, a lubricant, a filler, a binder, taste masking agents, an effervescent disintegration agent, and combinations of any of these agents.

(V) Polymers

Another aspect of the present invention encompasses polymers comprising a repeat unit having Formula (XX):

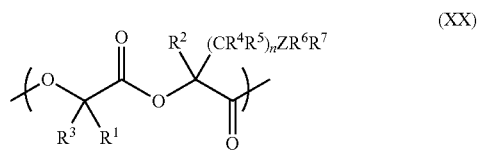

(XX)

wherein,
$R^1$, $R^2$, $R^3$, $R^4$, and $R^5$ are independently chosen from hydrogen, hydrocarbyl, and substituted hydrocarbyl;
$R^6$ is chosen from hydrogen, hydrocarbyl, and substituted hydrocarbyl;
$R^7$ is optionally present, when present it is chosen from hydrogen, hydrocarbyl, and substituted hydrocarbyl;
Z is chosen from nitrogen, sulfur, sulfone, sulfoxide, and selenium; and
n is an integer≥1.

The repeat unit of the polymers disclosed herein, therefore, derives from the cyclic dimer compounds of Formulas (II) or (V). In various embodiments, $R^2$, $R^4$, $R^5$, $R^6$, $R^7$, Z, and n may vary as detailed above in section (I). For example, $R^2$, $R^4$, $R^5$, $R^6$, and $R^7$, when present, may be independently chosen from hydrogen, alkyl, aryl, alkyl aryl, substituted alkyl, substituted aryl, and substituted alkylaryl.

In some embodiments, $R^1$ comprises $(CR^8R^9)_mYR^{10}R^{11}$ and the repeat unit of the polymer comprises Formula (XXa):

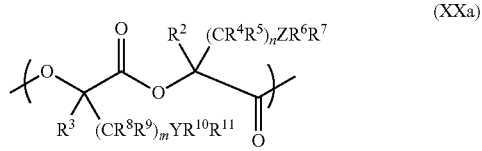

wherein:
$R^2$, $R^3$, $R^4$, $R^5$, $R^6$, $R^8$, $R^9$, and $R^{10}$ are independently chosen from hydrogen, hydrocarbyl, and substituted hydrocarbyl;
$R^7$ and $R^{11}$ are optionally present, when present they are independently chosen from hydrogen, hydrocarbyl, and substituted hydrocarbyl;
Y and Z are independently chosen from nitrogen, sulfur, sulfone, sulfoxide, and selenium; and
n and m are integers≥1.

Each of $R^2$, $R^3$, $R^4$, $R^5$, $R^6$, $R^7$, $R^8$, $R^9$, $R^{10}$, $R^{11}$, Y, Z, n and m may vary as described above in section (I). In various embodiments, $R^2$, $R^3$, $R^4$, $R^5$, $R^8$ and $R^9$ are hydrogen, n and m independently range from 1 to 10; Z and Y are independently chosen from sulfur, sulfone, sulfoxide, and selenium. In some iterations, $R^6$ and $R^{10}$ are lower chain alkyl, and $R^7$ and $R^{11}$, if present, are independently hydrogen or lower chain alkyl. In an exemplary embodiment, each of $R^2$, $R^3$, $R^4$, $R^5$, $R^8$ and $R^9$ are hydrogen, both n and m are 2, both Z and Y are sulfur, both $R^6$ and $R^{10}$ are methyl, and neither $R^7$ nor $R^{11}$ are present.

In exemplary embodiments, the repeat unit comprises Formula (XXV):

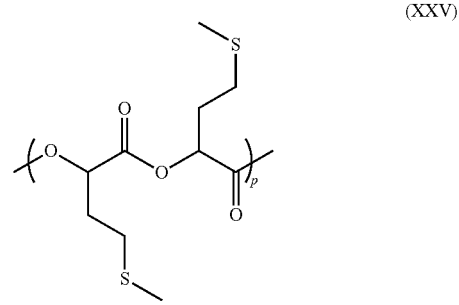

wherein:
p is an integer greater than 1;
provided that when p is less than 4, then the polymer has a polydispersity index of less than about 1.3.

The polymers comprising repeat units having Formulas (XX), (XXa), and (XXV) may have a variety of average molecular weights. In various embodiments, the polymer may be an average molecular weight that ranges from about 200 to about 2,000 Da, from about 2,000 to about 5,000 Da, from about 5,000 to about 10,000 Da, from about 10,000 to about 30,000, from about 30,000 to about 60,000 Da, from about 60,000 to about 100,000 Da, from about 100,000 to about 150,000 Da, from about 150,000 to about 300,000 Da, from about 300,000 to about 600,000 Da, from about 600,000 to about 1,000,000 Da, from about 1 million to about 2 million Da, from about 2 million to about 5 million Da, or greater than about 5 million Da.

The polymers disclosed herein generally have a narrow molar mass distribution. The polydispersity index (PDI), which is equal to Mw/Mn, is generally less than about 1.8. In some embodiments, the PDI is less than about 1.7, less than about 1.6, less than about 1.5, less than about 1.4, less than about 1.3, less than about 1.2, or less than about 1.1. In exemplary embodiments, the polymers have a PDI of less than about 1.3.

The polymers disclosed herein contain essentially no monomer or fraction of a monomer. The monomer may be a compound comprising Formula (II) or (V), which are detailed above in section (I). In certain embodiments, the monomer content of the homopolymer may be less than about 5%, less than about 4%, less than about 3%, less than about 2%, less than about 1% of a monomer, or less than about 0.5%.

The polymers disclosed herein may be linear, ring, branched polymers or copolymers (see below). Branched polymers include be, without limit, star polymers, comb polymers, brush polymers, dendrimers, dendronized polymers, and ladder polymers. Polymers prepared from optically pure monomers may be crystalline or semi-crystalline.

The polymers comprising repeat units having Formulas (XX), (XXa), or (XXV) may have one set of properties under one set of conditions and a different set of properties under different conditions. In some embodiments, the homopolymers provided herein may be stable in aqueous solutions under approximately neutral pH. In other embodiments, the homopolymers provided herein may hydrolyze in aqueous solutions at pH values of less than about 6.0, less than about 5.0, less than about 3.0, less than about 2.0, or less than about 1.0.

In general, the repeat unit of the polymers disclosed herein has at least one chiral center. In particular, the alpha carbon adjacent to the carbonyl unit may be chiral. Depending upon the identities of $R^2$, $R^3$, $R^4$, $R^5$, $R^6$, $R^7$, $R^8$, $R^9$, $R^{10}$, $R^{11}$, Y, and Z, the repeat unit may have additional chiral centers. Each chiral center may have an R or an S configuration. In embodiments in which the repeat unit comprises Formula (XXVI), each repeat unit has two chiral carbons. Thus each repeat unit may have an RR, RS, SR, or SS configuration.

(a) Homopolymers

In some embodiments, the polymer detailed above may be a homopolymer. That is, each repeat unit is identical throughout the length of the polymer.

In some embodiments, the homopolymer comprises Formula (XXI):

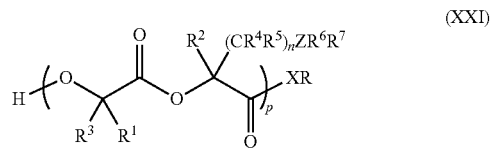

wherein:
R is chosen from hydrogen, hydrocarbyl, and substituted hydrocarbyl;
$R^1$, $R^2$, $R^3$, $R^4$, and $R^5$ are independently chosen from hydrogen, hydrocarbyl, and substituted hydrocarbyl;
$R^6$ is chosen from hydrogen, hydrocarbyl, and substituted hydrocarbyl;
$R^7$ is optionally present, when present it is chosen from hydrogen, hydrocarbyl, and substituted hydrocarbyl;
Z is chosen from nitrogen, sulfur, sulfone, sulfoxide, and selenium;
X is chosen from oxygen and nitrogen;
n is an integer≥1; and
p is an integer greater than 1.

In various embodiments R may be hydrogen, alkyl, aryl, alkylaryl, substituted alkyl, substituted aryl, and substituted alkylaryl. In some embodiments, R is may be alkyl. In other embodiments, R may be polyethylene oxide, polypropylene oxide, polyvinyl alcohol, or another polymer. $R^1$, $R^2$, $R^3$, $R^4$, $R^5$, $R^6$, $R^7$, Z, and n may vary as described above in section (I).

In one embodiment, $R^1$ comprises $(CR^8R^9)_m YR^{10}R^{11}$ and the polymer comprises repeat units comprising Formula (XXa), as detailed above.

In one exemplary embodiment, the polymer comprises Formula (XXV):

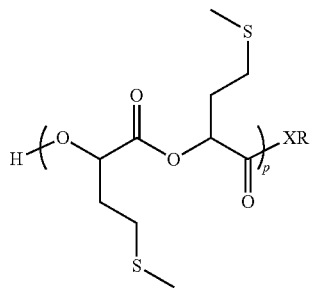

(XXVI)

wherein:
R is chosen from hydrogen, hydrocarbyl, and substituted hydrocarbyl;
X is chosen from oxygen and nitrogen; and
p is an integer greater than 1;
provided that when p is less than 4, then the polymer has a polydispersity index of less than about 1.3.

In some embodiments of the polymer comprising Formula (XXVI), X is oxygen and R is $C_1$ to $C_{20}$ alkyl. In other embodiments of the polymer comprising Formula (XXVI), XR may be an amine.

(b) Copolymers

In some embodiments, the polymer detailed above may further comprise at least one second repeat. That is, the polymer is a copolymer comprising a first repeat unit comprising Formula (XX) and at least one second repeat unit.

In some iterations of this embodiment, the second repeat unit also comprises Formula (XX), however, the second repeat unit is substituted differently in at least one position than the first repeat unit comprising Formula (XX).

In other iterations, the second repeat unit may be an acrylate, an aminoacrylate, an alkylene succinate, an alkylene oxalate, an amide, an amino acid, an anhydride, an arylate, a carbonate, a cellulose, a caprolactone, a cyanoacrylate, a cyclic ether, a dihydropyran, a dioxane, a dioxanone, an ether ether ketone, an ethylene glycol, a fumarate, an hydroxyl alkanoate, an hydroxy ester, an imide, a ketal, a lactide, lactone, a methacrylate, a methyl olefin, an orthoester, a phosphazine, a styrene, a terephthalate, a tetrahydrofuran a trimethylene carbonate, an urethane, a vinyl acetate, a vinyl ketone, a vinyl halide, a derivative of any of the forgoing, or mixtures thereof. In certain embodiments, the second repeat unit a lactide, a lactone, a lactam, an hydroxyl alkanoate, a hydroxyl ester, a cyclic ether, a tetrahydrofuran, a dioxane, a dioxanone, and mixtures thereof. In exemplary embodiments, the second repeat unit may be chosen from lactide and ethylene oxide. In one exemplary embodiment, the first repeat unit comprises Formula (XXVI) and the second repeat unit is lactide. In another exemplary embodiment, the first repeat unit comprises Formula (XXV) and the second repeat unit is ethylene oxide.

The weight ratio of the first repeat unit to the second repeat unit may vary depending on the desired properties of the copolymer. In some aspects, the weight ratio of the first repeat unit comprising Formula (XX) to the second repeat unit may range from about 99.9:0.1 to about 0.1:99.9. In various embodiments the weight ratio of the first repeat unit comprising Formula (XX) to the second repeat unit may be about 99:1, 95:5, 90:10, 85:15, 80:20, 75:25, 70:30, 65:35, 60:40, 55:45, 50:50, 45:55, 40:60, 35:65, 30:70, 25:75, 20:80, 15:85, 10:90, 5:95, or 1:99 weight %. Similarly, in embodiments in which the combination comprises three or more repeat units, the amount of each compound can and will vary.

In various embodiments, the copolymer may be an average molecular weight that ranges from about 200 to about 2,000 Da, from about 2,000 to about 5,000 Da, from about 5,000 to about 10,000 Da, from about 10,000 to about 30,000, from about 30,000 to about 60,000 Da, from about 60,000 to about 100,000 Da, from about 100,000 to about 150,000 Da, from about 150,000 to about 300,000 Da, from about 300,000 to about 600,000 Da, from about 600,000 to about 1,000,000 Da, from about 1 million to about 2 million Da, from about 2 million to about 5 million Da, or greater than about 5 million Da.

The copolymers disclosed herein may be may be alternating copolymers, random copolymers, block copolymers, linear copolymers, graft copolymers, or branched copolymers. Suitable branched copolymers include star polymers, $AB_2$ star polymers, palm-tree $AB_n$ polymers, H-shaped $B_2AB_2$ polymers, dumbbell polymers, star block $AB_n$ polymers, star $A_nB_n$ polymers, comb polymers, brush polymers, dendrimers, dendronized polymers, ladder polymers, and so forth. The copolymers may be crystalline or semi-crystalline.

(VI) Polymerization Processes

A further aspect of the present disclosure provides processes for the formation of the polymers detailed above in section (V).

The polymers detailed in section (V) may be prepared by contacting a plurality of compounds comprising Formula (II) in the presence of a catalyst to form the homopolymer comprising the repeat unit comprising Formula (XX). The compound comprising Formula (II) and the repeat unit comprising Formula (XX) have the following structures:

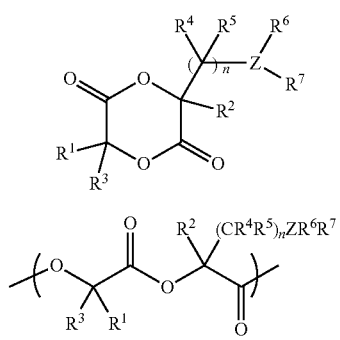

(II)

(XX)

wherein:

R¹, R², R³, R⁴, and R⁵ are independently chosen from hydrogen, hydrocarbyl, and substituted hydrocarbyl;

R⁶ is chosen from hydrogen, hydrocarbyl, and substituted hydrocarbyl;

R⁷ is optionally present, when present it is chosen from hydrogen, hydrocarbyl, and substituted hydrocarbyl;

Z is chosen from nitrogen, sulfur, sulfone, sulfoxide, and selenium; and n is an integer≥1.

Each of $R^1$, $R^2$, $R^4$, $R^5$, $R^6$, $R^7$, Z, and n may be chosen as described above in section (I). In some embodiments, $R^1$ comprises $(CR^8R^9)_m YR^{10}R^{11}$, wherein $R^8$, $R^9$, $R^{10}$, $R^{11}$, Y, and m may be chosen as described in section (I).

In an exemplary embodiment, the reacting compounds comprise Formula (V) and the repeat unit of the polymers comprises Formula (XXVI):

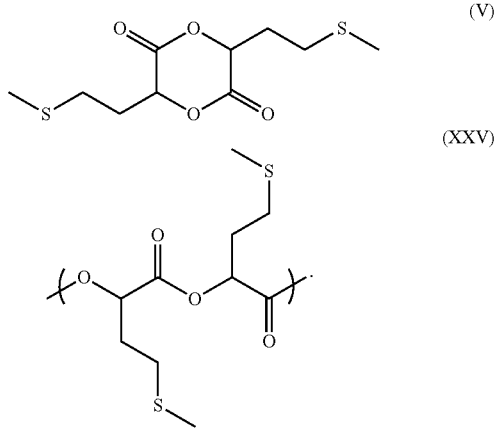

(V)

(XXV)

The process comprises contacting a plurality of compounds comprising Formula (II) or Formula (V) under the appropriate ring opening conditions to facilitate polymerization. In general, the polymerization reaction is conducted in the presence of a catalyst. Suitable catalysts include, without limit, tin(II) octanoate (stannous octanoate), aluminum(III) isopropoxide, zinc(II) lactate, yttrium complexes, bis- and trisaryl tin complexes, heterobimetallic iron(II) complexes, titanium complexes with bridged-biphenolate ligands, cationic aluminum complexes, pyridine catalysts, and the like. In an exemplary embodiment, the catalyst may be stannous octanoate.

The amount of catalyst used in the reaction can and will vary. In general, the amount of catalyst may range from about 0.001 wt % of the amount of the compound comprising Formula (II) or Formula (V) to about 2 wt % of the compound comprising Formula (II) or Formula (V). In some embodiments, the catalyst may be added in an amount below 2 wt %, below 1 wt %, or below 0.1 wt %. More preferably, the catalyst may be provided in the reaction in a weight percentage of about 0.01, 0.02, 0.03, 0.04, 0.05, 0.06, 0.07, 0.08, 0.09, or 0.10 mol % to the compound comprising Formula (IIb).

The reaction may be conducted in the presence of a solvent. Alternatively the reaction may be conducted neat. In embodiments in which a solvent is included in the reaction mixture, the choice of solvent will depend upon the identity of the compounds comprising Formula (II) or Formula (V). Examples of suitable solvents are detailed above in section (IIa). In an exemplary embodiment, the solvent may be toluene. The amount of solvent added to the reaction mixture can and will vary. Typically, the weight-to-weight ratio of the solvent to the compound comprising Formula (II) or Formula (V) may range from about 1:1 to about 100:1. In various embodiments, the weight-to-weight ratio of the solvent to the compound comprising Formula (II) or Formula (V) may range from about 1:1 to 5:1, from about 5:1 to about 20:1, from about 20:1 to about 40:1, from about 40:1 to about 80:1, or from about 80:1 to about 100:1.

The reaction mixture may further comprise a ring opening initiator. The initiator may be any compound (i.e., a small molecule or a polymer) comprising at least one hydroxyl group and/or an amine group. Suitable initiators include water, alcohols, polyols (e.g., glycerol, sugar alcohols, etc.) polymers comprising hydroxyl groups (e.g., polyethylene oxide, polypropylene oxide, polyvinyl alcohol), glycols, polyglycols, and primary or secondary amines of low molecular weight. In exemplary embodiments the initiator may be water, methanol, ethanol, propanol, butanol, pentanol, hexanol, heptanol, octanol, nonanol, decanol, polyethylene oxide, polyvinyl alcohol, and the like.

The temperature of the polymerization reaction may vary. In general, the reaction is conducted at a temperature that ranges from about 100° C. to about 200° C. In various embodiments, the temperature of the reaction may range from about 100° C. to about 120° C., from about 120° C. to abut 140° C., from about 140° C. to about 160° C., from about 160° C. to about 200° C. In exemplary embodiments, the temperature of the reaction may be about 140° C., about 160° C., or any temperature in-between. In general, the reaction is conducted under an inert atmosphere. For example, the reaction may be performed under nitrogen, under argon, or another inert gas.

The duration of the reaction can and will vary. In general, the duration of the reaction may range from about 1 hour to about 3 days. In various embodiment, the duration of the reaction may range from about 1 to 5 hours, from about 5 to 10 hours, from about 10 to 18 hours, from about 18 to 24 hours, from about 24 to about 30 hours, from about 30 to about 40 hours, or from about 40 hours to about 60 hours.

In some embodiments, the polymer may be prepared by an extrusion process. Generally, processes of extrusion involve feeding the reaction mixture into an extruder which heats and shears the mixture. Generally, shearing occurs through an apparatus which pushes the heated polymer through an orifice. The extruder may be chosen from any commercially available extruder and may be a single screw extruder or preferably a twin-screw extruder that mechanically shears the mixture with the screw elements.

In general, substantially all of the compounds comprising Formula (II) or Formula (V) are polymerized and converted into the polymer. In various embodiments, the conversion of the compounds comprising Formula (II) or Formula (V) may be greater than about 90%, greater than about 95%, greater than about 98%, or greater than about 99%. In general, the polymer is substantially free of monomer (i.e., the compound comprising Formula (IIb) or Formula (V)).

The resultant polymer may be isolated and/or purified from the reaction mixture using means well known in the art including size exclusion chromatography, HPLC, ion-exchange chromatography, other types of chromatography, precipitation, and/or crystallization.

The copolymers detailed in section (V)(b) may be prepared by contacting a plurality of compounds comprising Formula (II) or Formula (V) with a plurality of at least one additional type of monomer during the polymerization process. The additional monomers may be added concurrently with the compounds comprising Formula (II) or Formula (V), may be added after the compounds comprising Formula (II) or Formula (V), or may be added alternately with the compounds comprising Formula (II) or Formula (V). Those skilled in the art will appreciate that many variations are possible, considering the many different types of copolymers that can be made.

The additional monomers may be chosen from acrylates, aminoacrylates, alkylene succinates, alkylene oxalates, amides, amino acids, anhydrides, arylates, carbonates, cellulose, caprolactone, caprolactam, cyanoacrylates, cyclic ethers, dihydropyrans, dioxanes, dioxanones, ether ether ketones, ethylene glycol, fumarates, hydroxy alkanoates, hydroxy esters, imides, ketals, lactides, lactones, methacrylates, methyl olefins, orthoesters, phosphazines, styrenes, terephthalates, tetrafurans. trimethylene carbonate, urethanes, vinyl acetates, vinyl ketones, vinyl halides, derivatives, isomers, and mixtures thereof.

The ratio of the additional monomer to the compounds comprising Formula (II) or Formula (V) may range from about 99.9:0.1 to about 0.1:99.9 weight %. For example, additional monomers may be provided in a ratio of 99:1, 95:5, 90:10, 85:15, 80:20, 75:25, 70:30, 65:35, 60:40, 55:45, 50:50, 45:55, 40:60, 35:65, 30:70, 25:75, 20:80, 15:85, 10:90, 5:95, or 1:99 weight % to the compounds comprising Formula (II) or Formula (V). Similarly, in embodiments in which the combination comprises three or more monomers, the amount of each monomer can and will vary.

(VII) Applications

The polymers detailed above in section (V) may be used in a variety of applications. Non-limiting examples of suitable uses include plasticizers, processing aids, adhesives, coatings, lacquers, films, emulsifiers, antioxidant agents, antimicrobial agents, anticorrosive agents, nutritive agents, or feed additives. In various embodiments, the polymers disclosed herein may be used in packaging materials (e.g., trash bags, biodegradable bags, grocery bags, wrappings, food containers, film wrapping, laminated papers, bottles), consumer goods (e.g., fast-food tableware, containers, egg cartons, razor handles, toothbrushes, pens, cartridges, toys), disposable non-wovens (e.g., engineered fabrics; diaper backings, surgical gowns, drapes, and the like), cosmetics, personal care products, home care products, medical applications (e.g., drug delivery, scaffolds for tissue engineering, medical prostheses, wound dressing, sutures, bone replacement, fixation of fractures, fixation of ligaments, cartilage repair, menisci repair, medical devices, stents, orthopedic/surgical materials (e.g., screws, pins, plugs, etc.), haemostatic devices, sensor devices), and agricultural applications (e.g., mulch films, planters).

(VIII) Polymer Compositions

In yet another aspect, the present disclosure encompasses polymer compositions. In some embodiments, the polymer composition comprises a first polymer as described in section (V) and at least one additional polymer to form a polymer blend. As used herein, a blend is a macroscopic homogeneous or miscible mixture of two or more different polymers and is formed by tailoring compositions to meet specific end-use requirements.

In various embodiments, the additional polymer may be selected from crystalline and semicrystalline polymers. Examples of suitable polymers, without limitation, are polymers of acrylates, aminoacrylates, alkylene succinates, alkylene oxalates, amides, amino acids, anhydrides, arylates, carbonates, cellulose, caprolactone, cyanoacrylates, cyclic ethers, dihydropyrans, dioxanes, dioxanones, ether ether ketones, ethylene glycol, fumarates, hydroxy alkanoates, hydroxy esters, imides, ketals, lactides, lactones, methacrylates, methyl olefins, orthoesters, phosphazines, styrenes, terephthalates, tetrafurans. trimethylene carbonate, urethanes, vinyl acetates, vinyl ketones, vinyl halides, derivatives, isomers, and mixtures thereof. In exemplary embodiments, the second polymer may be chosen from poly (lactide), poly(ethyl cellulose), and polyvinyl alcohol.

The additional polymer may vary in molecular weight. In some embodiments, the additional polymer may range from about 500 Da to greater than 1,000,000 Da. In some embodiments, the molecular weight of the additional polymer may be about 2,000 Da, 10,000 Da, 20,000 Da, 30,000 Da, 40,000 Da, 50,000 Da, 60,000 Da, 70,000 Da, 80,000 Da, 90,000 Da, 100,000 Da, 500,000 Da, 1,000,000 Da and may range between and including any two of these values. The additional polymer may be characterized by a weight-average molecular weight. In some aspects, the weight-average molecular weight of the additional polymer used in the blend may be at least 500 Da. In other aspects, the weight-average molecular weight of the additional polymers may be about 1,000 Da to about 1,000,000 Da.

The amount of the first polymer detailed in section (V) and the additional polymer may depend on the desired properties of the combination. In some aspects, the weight ratio of the first polymer to the additional polymer may range from about 99.9:0.1 to about 0.1:99.9 weight %. In various embodiments the weight ratio of the first polymer to the additional polymer may be about 99:1, 95:5, 90:10, 85:15, 80:20, 75:25, 70:30, 65:35, 60:40, 55:45, 50:50, 45:55, 40:60, 35:65, 30:70, 25:75, 20:80, 15:85, 10:90, 5:95, or 1:99 weight %. In some embodiments, the blend comprises more than one additional polymer. In embodiments in which the combination comprises two or more additional polymers, the amount of each polymer can and will vary.

In other embodiments, the polymer composition may be a feed composition comprising a polymer from section (V) and at least one additional agent chosen from one or more of the following: carbohydrates, fats, proteins, amino acids, and alpha hydroxy acids. Suitable sources of carbohydrates fats, proteins, amino acids, and alpha hydroxy acids are detailed above in section (IV)(a). In still other embodiments, the polymer composition may comprise a polymer from section (V) and at least one nutritive and/or pharmaceutical agent. Suitable nutritive and pharmaceutical agents are detailed above in section (IV)(b).

Definitions

When introducing elements of the embodiments described herein, the articles "a", "an", "the" and "said" are intended to mean that there are one or more of the elements. The terms "comprising", "including" and "having" are intended to be inclusive and mean that there may be additional elements other than the listed elements.

The compounds described herein have asymmetric centers. Compounds of the present invention containing an asymmetrically substituted atom may be isolated in optically active or racemic form. All chiral, diastereomeric, racemic forms and all geometric isomeric forms of a structure are intended, unless the specific stereochemistry or isomeric form is specifically indicated.

The term "acyl," as used herein alone or as part of another group, denotes the moiety formed by removal of the hydroxyl group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "allyl," as used herein not only refers to compound containing the simple allyl group ($CH_2$=CH—$CH_2$—), but also to compounds that contain substituted allyl groups or allyl groups forming part of a ring system.

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkoxide" or "alkoxy" as used herein is the conjugate base of an alcohol. The alcohol may be straight chain, branched, cyclic, and includes aryloxy compounds.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The terms "aryl" or "Ar" as used herein alone or as part of another group denote optionally substituted homocyclic aromatic groups, preferably monocyclic or bicyclic groups containing from 6 to 10 carbons in the ring portion, such as phenyl, biphenyl, naphthyl, substituted phenyl, substituted biphenyl, or substituted naphthyl.

The term "copolymer" refers to a polymer containing two or more different repeat units.

The term "crystalline polymer" as used herein refers to a polymer having the characteristic or regular three-dimensional packing.

The term "enrichment" means an amount above the statistical distribution if all chiral centers had an equal probability of being alpha or beta.

The terms "carbocyclo" or "carbocyclic" as used herein alone or as part of another group denote optionally substituted, aromatic or non-aromatic, homocyclic ring or ring system in which all of the atoms in the ring are carbon, with preferably 5 or 6 carbon atoms in each ring. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

The terms "epoxy" or "epoxide" as used herein means a cyclic ether. The ring structure generally comprises from 2 to 5 carbon atoms in the ring.

The terms "halogen" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

The term "homopolymer" refers to a polymer containing a single type of repeat unit.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "protecting group" as used herein denotes a group capable of protecting a particular moiety, wherein the protecting group may be removed, subsequent to the reaction for which the protection is employed, without disturbing the remainder of the molecule. A variety of protecting groups and the synthesis thereof may be found in "Protective Groups in Organic Synthesis" by T. W. Greene and P. G. M. Wuts, John Wiley & Sons, 1999.

The term "semi-crystalline polymer" as used herein refers to a polymer with both regions that are "crystalline" as describe above, and regions that are amorphous, having no regular packing to the three-dimensional structure.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorus, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

Having described the invention in detail, it will be apparent that modifications and variations are possible without departing from the scope of the invention defined in the appended claims.

EXAMPLES

The following examples illustrate various embodiments of the invention.

Example 1: Preparation of 3,6-bis(2-Methylthio)ethyl-1,4-dioxane-2,5 Dione

The cyclic dimer 3,6-bis(2-methylthio)ethyl-1,4-dioxane-2,5 dione was prepared according to the following reaction scheme:

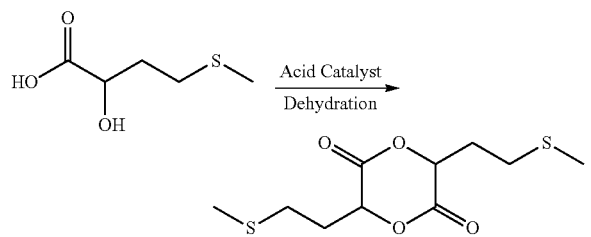

A solution of 524.6 g of Alimet® (88% 2-hydroxy-4-(methylthio)butanoic acid (HMTBa) in toluene (14054 g) was treated with catalytic p-toluene sulfonic acid monohydrate (21.1 g). The reaction flask was fitted with a Dean Stark trap and condenser. The reaction was heated to 110° C. and approximately 95 mL of water was collected over about 5 hours. After 5 hours, the reaction was cooled to room temperature and washed twice with saturated sodium bicarbonate, and twice with water. The toluene was then removed under reduced pressure. The residue was dried to a solid under high vacuum. To the solid residue was then added 300 mL of methyl t-butyl ether, and the solid dissolved at 50° C. The solution was cooled to ambient temperature, and then to 2-4° C. to crystallize. The solution was warmed to ambient temperature and the solid filtered off and washed with minimal methyl t-butyl ether. The solid was dried on high vacuum to give 91.4 g (22 mol) of an off-white solid. LC/MS showed a racemic mixture (2 peaks) both with M+H=265, M+Na=287. $^1$H NMR (500 MHz, CHLOROFORM-d, race-mic mixture) ppm 2.07-2.16 (m, 6H), 2.21-2.46 (m, 4H), 2.65-2.83 (m, 4H), 5.17-5.32 (m, 2H). TLC (25% ethyl acetate/heptanes) rf: 0.16.

Example 2: Distillation of 2-Hydroxy-4-(Methylthio)butanoic Acid

In a flask 11 g of HMTBa and 11 mL of conc. HCl were added. The mixture was heated to 90° C. for 1 hour. The mixture was cooled and then concentrated at 5-10 Torr for 1.25 hrs until the pot temperature reached 100° C. After cooling to room temperature an aliquot of the reaction mixture was analyzed by HPLC. The chromatogram shown in FIG. 1A reveals the presence of monomers, dimers, trimers, and tetramers of HMTBa in the reaction mixture. To confirm that no cyclic dimer was present in the reaction mixture, an aliquot of the cyclic dimer prepared essentially as described in Example 1 was subjected to HPLC (using the same parameters as used for the analysis of the reaction mixture). FIG. 1B presents an overlay of the cyclic dimer chromatogram onto the HMTBa oligomer chromatogram. This analysis revealed that the cyclic dimer had a different elution time than the HMTBa oligomers.

Example 3: Azeotropic Distillation of 2-Hydroxy-4-(Methylthio)butanoic Acid

Figure 2A:
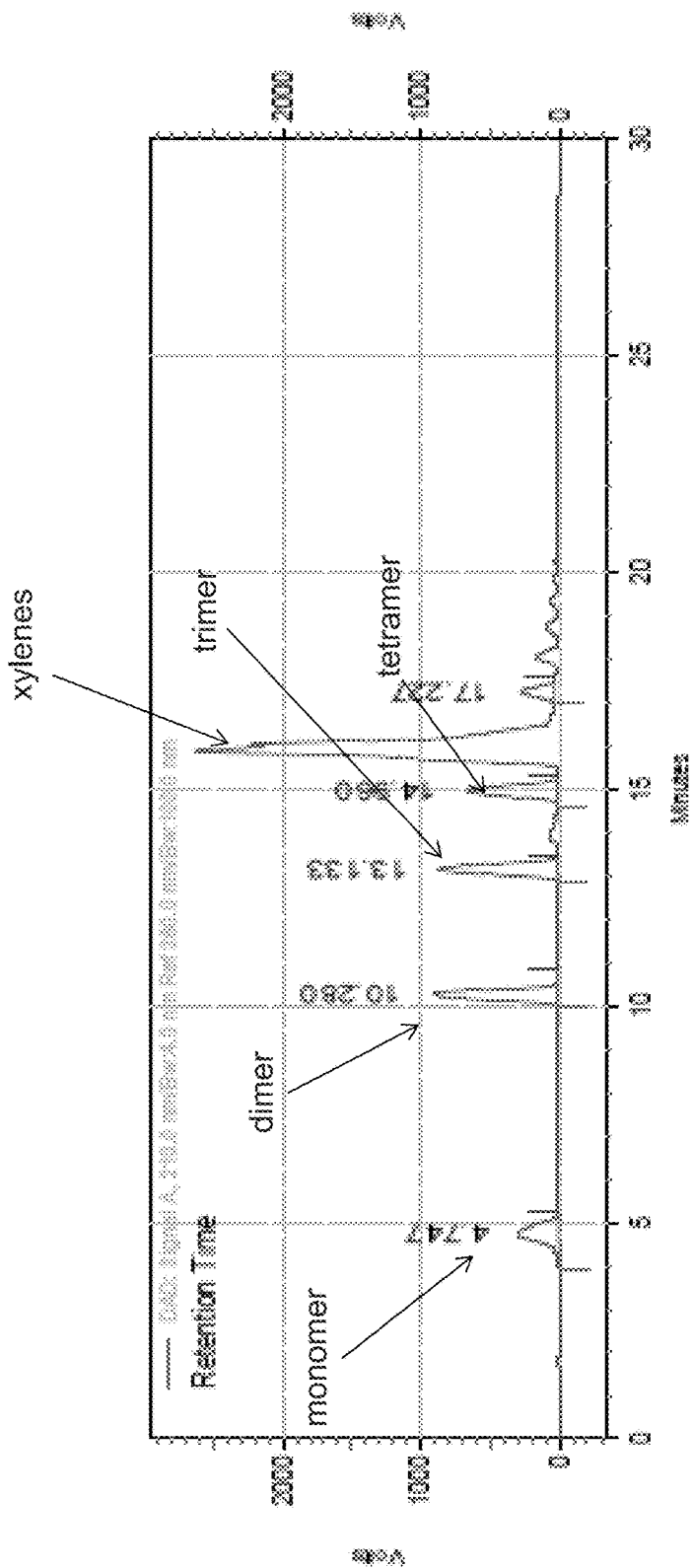
FIG. 2A-B shows the products formed after azeotropic distillation of 2-hydroxy-4-(methylthio)-butanoic acid (HMTBA).
Figure 2B:
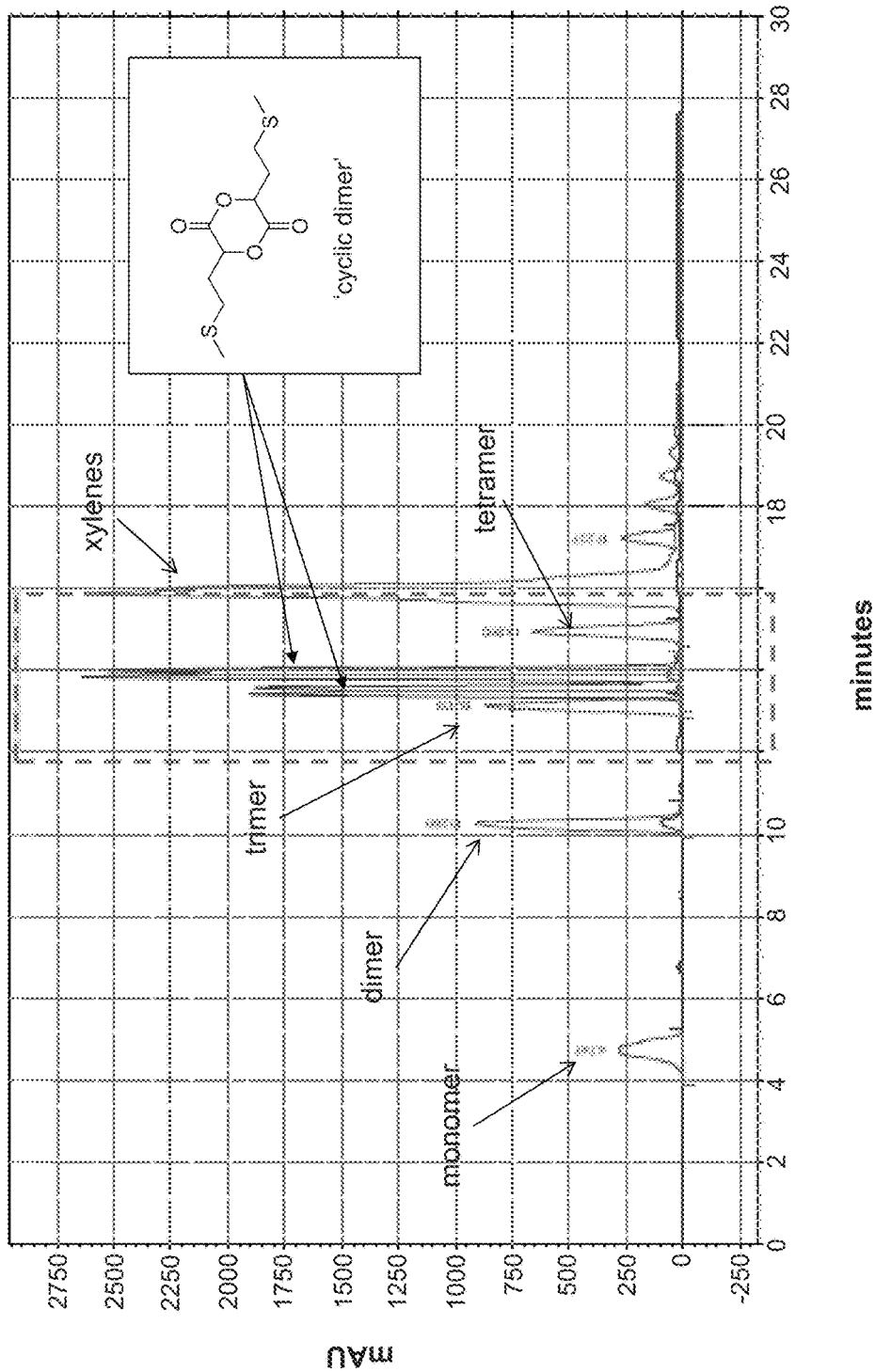

In a flask was added purified HMTBa and xylenes (no acid was present). The mixture was heated and water was removed by azetropic distillation for 4-6 hours. After cooling to room temperature an aliquot of the reaction mixture was analyzed by HPLC. As shown in FIG. 2A, the sample contained monomers, dimers, trimers, and tetramers of HMTBa, but no cyclic dimer. To confirm this, an aliquot of the cyclic dimer prepared essentially as described in Example 1 was subjected to HPLC (using the same parameters as used for the analysis of the reaction mixture). FIG. 2B presents an overlay of the cyclic dimer chromatogram onto the HMTBa oligomer chromatogram. This analysis revealed that the cyclic dimer had a different elution time than the HMTBa oligomers.

Example 4: Separation of Diastereomers

Alimet® and p-toluene sulfonic acid were reacted as described in Example 1. An aliquot (4.7 g) of the resulting solid was subjected to chiral chromatography (Chiralpak IA column, eluted with 70:30 hexane:THF at 25° C., with UV detection at 220 nm) and yielded three samples of the different diastereomers. The samples are detailed in Table 6.

TABLE 6

| Diastereomer Samples | | | |
|---|---|---|---|
| Sample | Diastereomer Excess | Retention time | Recovery* |
| #1 | >99% | 5.323 min | 1.09 g (92.9%) |
| #2 | 99.3% | 6.464 min | 1.18 g (100%) |
| #3 | >99% | 12.295 min | 2.09 g (89.3%) |

*% recovery does not take into account any residual BHT left in the product (−)-3,6-bis(2-methylthio)ethyl-1,4-dioxane-2,5 dione. 315 mg of #1 was suspended in 10 mL of methyl t-butyl ether and then filtered, and dried under high vacuum to give 235 mg of #1 with 98.7% purity (HPLC). $\alpha_D^{25}$ (c=1.042, $CH_2Cl_2$): −250.212. LCMS MH+265, M+Na 287.

(+)-3,6-bis(2-methylthio)ethyl-1,4-dioxane-2,5 dione. 309 mg of #2 was suspended in 10 mL of methyl t-butyl ether and then filtered, and dried under high vacuum to give 190 mg of #2 with >99% purity (HPLC). $\alpha_D^{25}$ (c=1.037, $CH_2Cl_2$): +250.263. LCMS MH+265, M+Na 287.

(meso)-3,6-bis(2-methylthio)ethyl-1,4-dioxane-2,5 dione. 420 mg of #3 was suspended in 10 mL of methyl t-butyl ether and then filtered, and dried under high vacuum to give 250 mg of #3 with 96% purity (HPLC). $\alpha_D^{25}$ (c=1.036, $CH_2Cl_2$): =0° (racemic). LCMS MH+265, M+Na 287.

Example 5: Polymerization of 3,6-bis(2-Methylthio)ethyl-1,4-dioxane-2,5 Dione

Into a 25 ml flask was placed 1.5 grams of 3,6-bis(2-methylthio)ethyl-1,4-dioxane-2,5 dione as prepared in Example 1 and a stirring bar, and then vacuum was applied on this flask for 1.5 h. Then 0.15 ml of catalyst solution (stannous octoate in toluene, 7.63 mM) was injected into the flask, which was filled with nitrogen. The temperature of the mixture was controlled at 140° C. for 48 hours. Analysis of the polymer by gel permeation chromatography (GPC) revealed that the number-average molar mass (Mn) was 3470 g/mol. (Mn=$\Sigma n_i/\Sigma n_i/M_i$). The Polydispersity Index (PDI) was 1.26. (PDI=Mw/Mn; Mw=mass-average molar mass=$\Sigma n_i M_i/\Sigma n_i$).

Example 6: Polymerization—Trial 2

Into a 25 ml flask was placed 1.5 grams of 3,6-bis(2-methylthio)ethyl-1,4-dioxane-2,5 dione and a stirring bar, and then a vacuum was applied on this flask for 1.5 h. Then 0.15 ml of catalyst solution (stannous octoate in toluene, 7.63 mM) was injected into the flask, which was filled with nitrogen, followed by addition of 2.5 mg of 1-octanol. The temperature of the mixture was controlled at 140° C. for 48 hours. Analysis of the resultant polymer revealed that it had a Mn of 2620 g/mol and a PDI of 1.5.

Example 7: Polymerization—Trial 3

Into a 25 ml flask was placed a magnetic stirring bar and 1.5 grams of 3,6-bis(2-methylthio)ethyl-1,4-dioxane-2,5 dione which was dried in vacuum oven at 30° C. for 3 days. The monomer was further dried on a vacuum line at room temperature. After the flask was filled with dry $N_2$, 0.15 ml of catalyst (stannous octoate in toluene, 7.63 mM) was added. The temperature of the polymerization was controlled at 160° C. for 48 hours. Analysis of the polymer resealed that the Mn was 4700 g/mol and the PDI was 1.46.

Example 8: Polymerization—Trial 4

Into a 25 ml flask was placed a magnetic stirring bar and 1.5 grams of 3,6-bis(2-methylthio)ethyl-1,4-dioxane-2,5 dione which was dried in vacuum oven at 30° C. for 3 days. The monomer was further dried on a vacuum line at room temperature. After the flask was filled with dry $N_2$, 0.15 ml of catalyst (stannous octoate in toluene, 7.63 mM) and 3.25 mg octanol was added. The temperature of the polymerization was controlled at 160° C. for 48 hours GPC analysis revealed that the polymer had a Mn of 3500 g/mol and a PDI of 1.69.

Example 9: Polymerization—Trial 5

Figure 3:
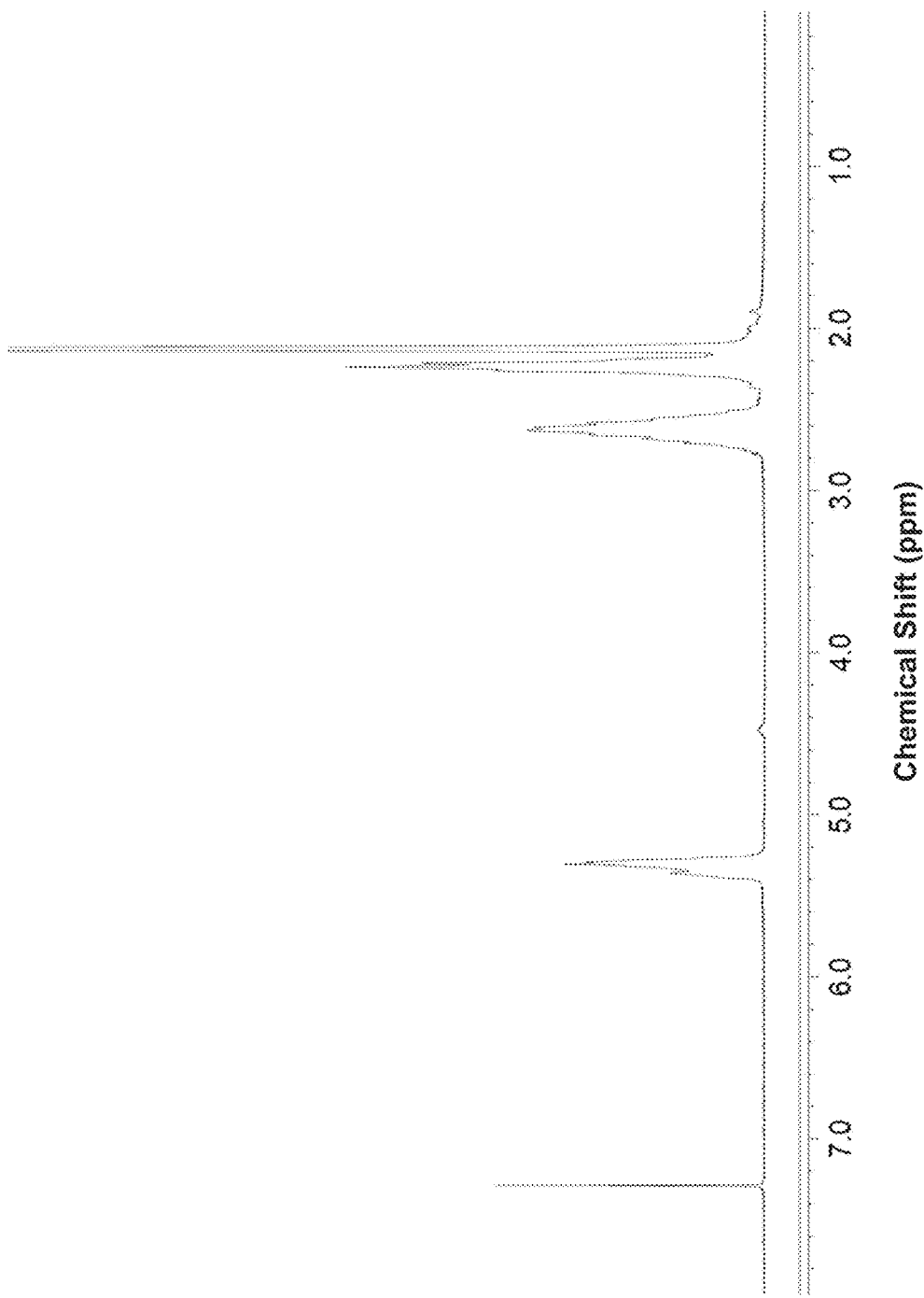
FIG. 3 presents an $^1$H NMR spectrum demonstrating the structure of the polymer prepared from 3,6-bis(2-methylthio)ethyl-1,4-dioxane-2,5 dione.

Into a 25 ml flask was placed a magnetic stirring bar and 1.5 grams of 3,6-bis(2-methylthio)ethyl-1,4-dioxane-2,5 dione which was dried in vacuum oven at 50° C. overnight. The monomer was further dried on a vacuum line at room temperature for 1 hour. After the flask was filled with dry $N_2$, 4.5 mg of stannous octoate was added. The temperature of the polymerization was ramped to and controlled at 140° C. for 28 hours. Analysis revealed that the Mn of the polymer was 8600 g/mol and the PDI was 1.27. The structure of the polymer was analyzed by $^1$H-NMR. FIG. 3 presents the NMR spectrum.

Example 10: Polymerization—Trial 6

Into a 25 ml flask was placed a magnetic stirring bar and 1.5 grams of 3,6-bis(2-methylthio)ethyl-1,4-dioxane-2,5 dione which was dried by vacuum pumping at 50° C. for several days. The monomer was further dried on a vacuum line at room temperature for 1 hour. After the flask was filled with dry $N_2$, 3 mg of stannous octoate was added. The temperature of the polymerization was ramped to and controlled at 140° C. for 22 hours. GPC analysis revealed that the Mn of the polymer was $3.3 \times 10^4$ g/mol and the PDI was 1.22. GPC coupled with light scattering detectors (GPC-LS) revealed that the Mn was $8.8 \times 10^4$ g/mol and the PDI was of 1.34.

Example 11: Polymerization—Trial 7

Into a 25 ml shlenk reaction tube was placed a magnetic stirring bar and 10.24 grams of 3,6-bis(2-methylthio)ethyl-1,4-dioxane-2,5 dione which was thoroughly dried by vacuum at 50° C. for several days. The monomer was further dried on a vacuum line at 58° C. for 2 hour. After the reactor was filled with dry $N_2$, 9 mg of stannous octoate was added. The temperature of the polymerization was ramped to and controlled at 140° C. for 21 hours. GPC analysis revealed an Mn of $6.3 \times 10^4$ g/mol and a PDI was 1.52. GPC-LS analysis revealed that the Mn was $1.1 \times 10^5$ g/mol and the PDI was 1.36.

Example 12: Polymerization—Trial 8

Into a 500 ml shlenk reaction flask was placed 120 grams of dry 3,6-bis(2-methylthio)ethyl-1,4-dioxane-2,5 dione, which was further dried on a vacuum line for 2.5 hours at 60° C. After the flask was filed with dry $N_2$, 0.1 ml of stannous octoate and 19 ml of octanol were injected to initiate the ring opening polymerization of the monomer. The mixture was heated up to and thermostated at 140° C. The reaction was continued for 2.5 hours. The polymer was recovered by pouring the reaction mixture into a container under $N_2$ protection. Conversion of the monomer was 98%. GPC analysis revealed that the Mn of the polymer was $1.3 \times 10^3$ g/mol and the PDI was 1.2.

Example 13: Kinetic Study of Ring Opening Polymerization

Figure 4:
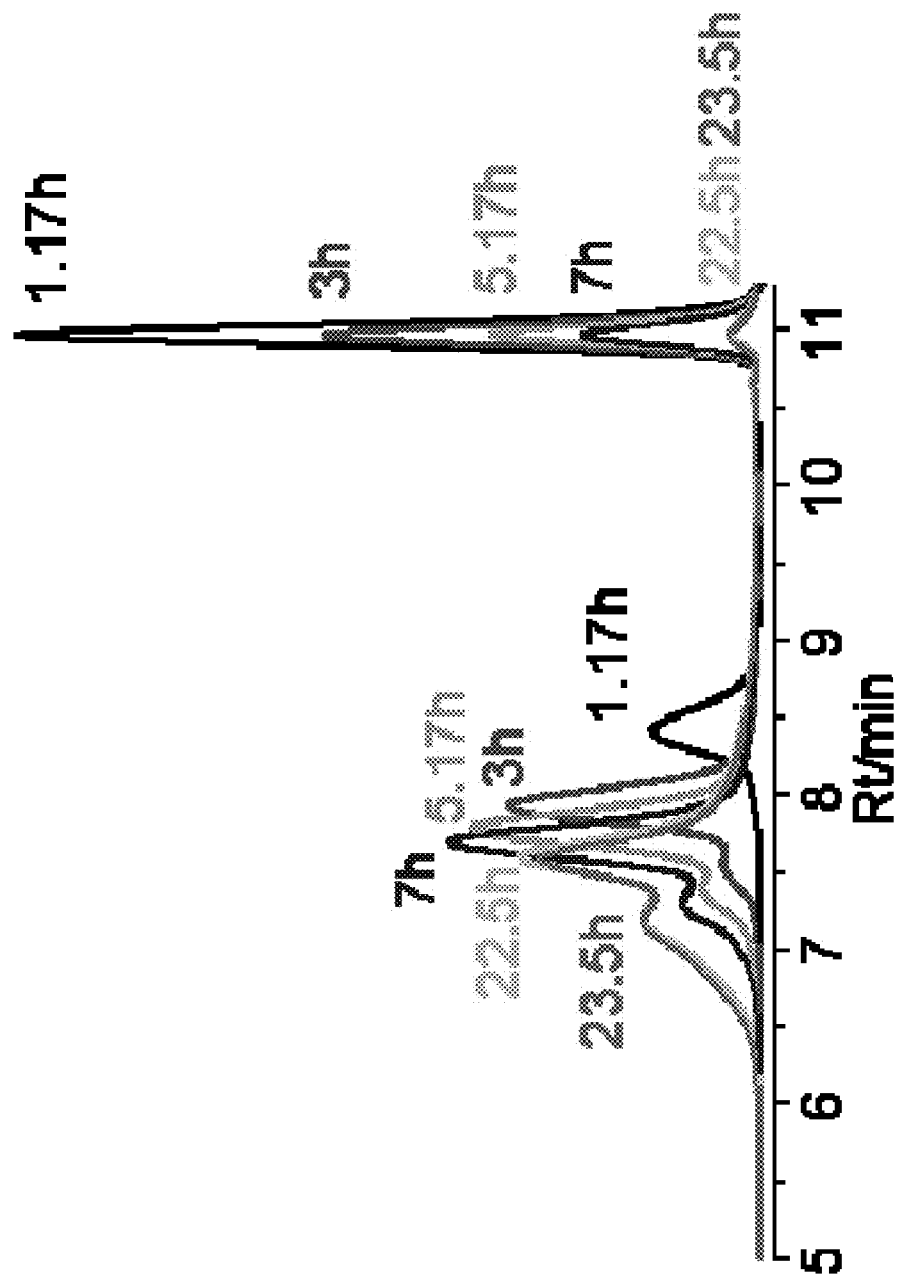
FIG. 4 shows gel permeation chromatograph traces monitoring ring opening polymerization of 3,6-bis(2-methylthio)ethyl-1,4-dioxane-2,5 dione as a function of time.

Into a 500 ml shlenk reaction flask was placed 122 grams of dry 3,6-bis(2-methylthio)ethyl-1,4-dioxane-2,5 dione, which was further dried on a vacuum line for 1 hour at 53-60° C. After the flask was filled with dry $N_2$, 0.1 ml of stannous octoate was injected to catalyze the ring opening polymerization of the monomer. The mixture was heated up to and thermostated at 140° C. The reaction was continued for 23.5 hours. At certain interval of reaction time, aliquots were removed and the molecular weight was analyzed by GPC. The GPC chromatograms from the various time points are shown in FIG. 4. The final polymer was recovered by pouring the reaction mixture into a container under N₂ protection. Conversion of the monomer was 96.1%. The Mn of the polymer was 4.35×10⁴ g/mol and the PDI was 1.58.

Figure 5:
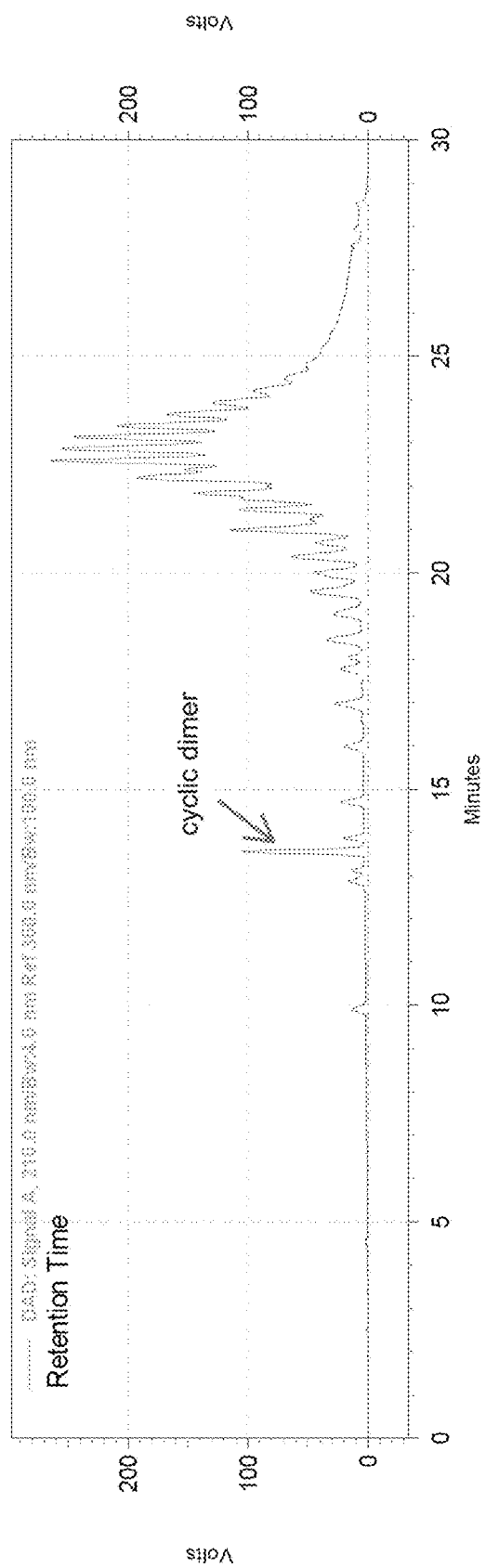
FIG. 5 presents an HPLC chromatogram of the reaction mixture of ring opening polymerization of 3,6-bis(2-methylthio)ethyl-1,4-dioxane-2,5 dione at 24 hours.

Example 14: Depolymerization of Polymer Formed From 3,6-bis(2-Methylthio)ethyl-1,4-dioxane-2,5 Dione First, the polymer was formed by charging 3.5 g of the cyclic dimer (3,6-bis(2-methylthio)ethyl-1,4-dioxane-2,5 dione) into a shlenk reaction flask, followed by injection of 0.15 ml of octanol and 5 droplets of stannous octoate (~15 mg). The reaction mixture was heated up to 140° C. and the reaction was allowed to proceed for 24 hours. An aliquot of the mixture was sampled and the conversion of the cyclic dimer to the polymer was determined to be 95 wt % (the concentration of cyclic dimer in the final mixture was 5%) (see FIG. 5).

Figure 6:
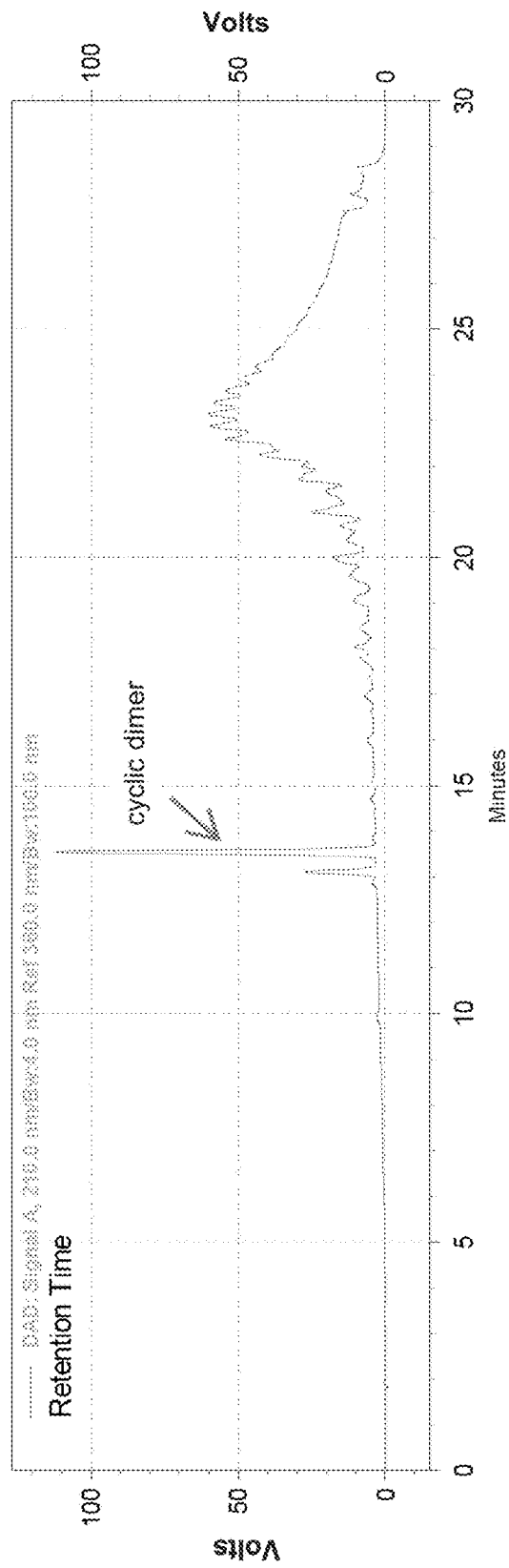
FIG. 6 shows HPLC analysis of the reaction mixture of the product shown in FIG. 5 after 2 hours of distillation at 200° C., 500 mTorr.
Figure 7:
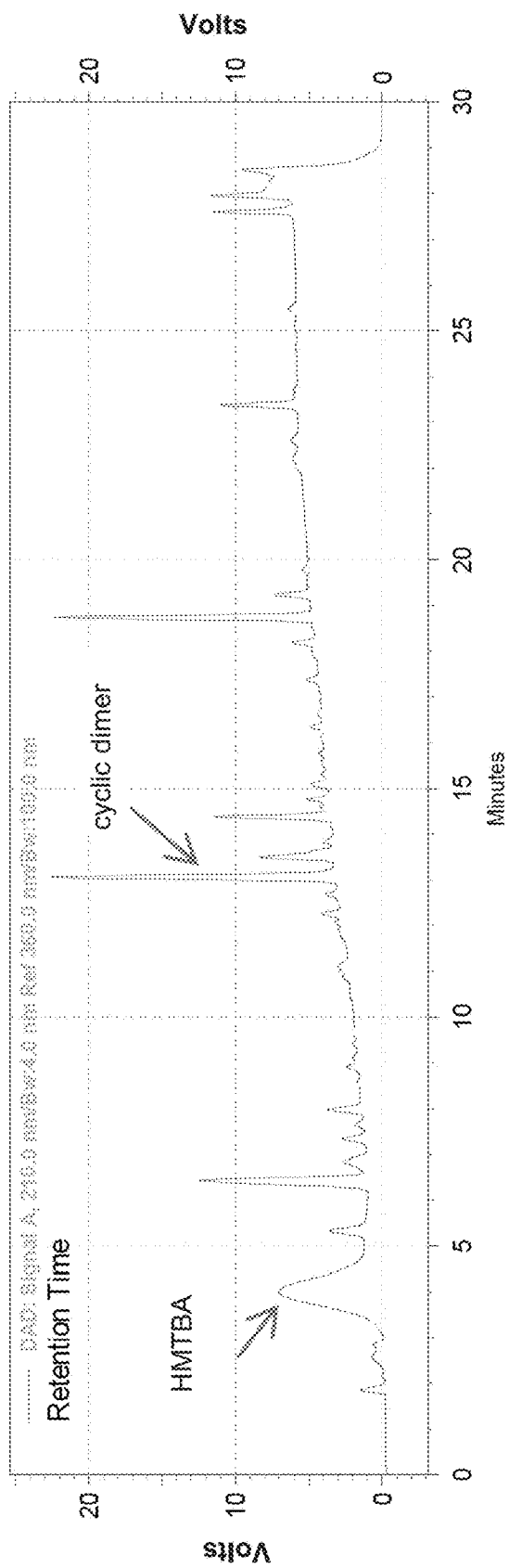
FIG. 7 presents HPLC analysis of distillates of the depolymerization reaction after 2 hours of distillation at 200° C., 500 mTorr.

For the thermal cracking step, the reactor was set up with distillation apparatus. The temperature of the mixture was raised to 200° C. and vacuum (~500 mTorr) was applied. The distillation was continued for 2 hours. An aliquot of the distilled reaction mixture and the distillates were analyzed by HPLC (see FIG. 6 and FIG. 7, respectively). Both HMTBa and the cyclic dimer (3,6-bis(2-methylthio)ethyl-1,4-dioxane-2,5 dione) were detected in the distillates. The mixture in the reaction pot was analyzed by GPC and it was determined that the concentration of cyclic dimer was 8.8%. The increase of the concentration of the cyclic dimer and the presence of HMTBA in the distillate strongly suggests the decomposition of the polymer into monomers during the thermal cracking step.

Example 15: Depolymerization of Polymer

The polymer was formed by charging 3.0 g of cyclic dimer into a shlenk reaction flask, followed by injection of 5 droplets of stannous octoate (~15 mg). The reaction mixture was heated to 140° C. and reacted for 22 hours. An aliquot of the mixture was sampled and the conversion of the cyclic dimer to the polymer was determined to be 97%.

For the thermal cracking step, the reactor was set up with a condenser and connected to a vacuum (200-500 mTorr). The temperature of the mixture was raised to 200° C. and kept for 2.5 h. The final reaction mixture was analyzed by GPC, which revealed that the concentration of the cyclic dimer in the mixture was 7.0%.

Example 16: Depolymerization of Polymer Formed from HMTBa

Figure 8:
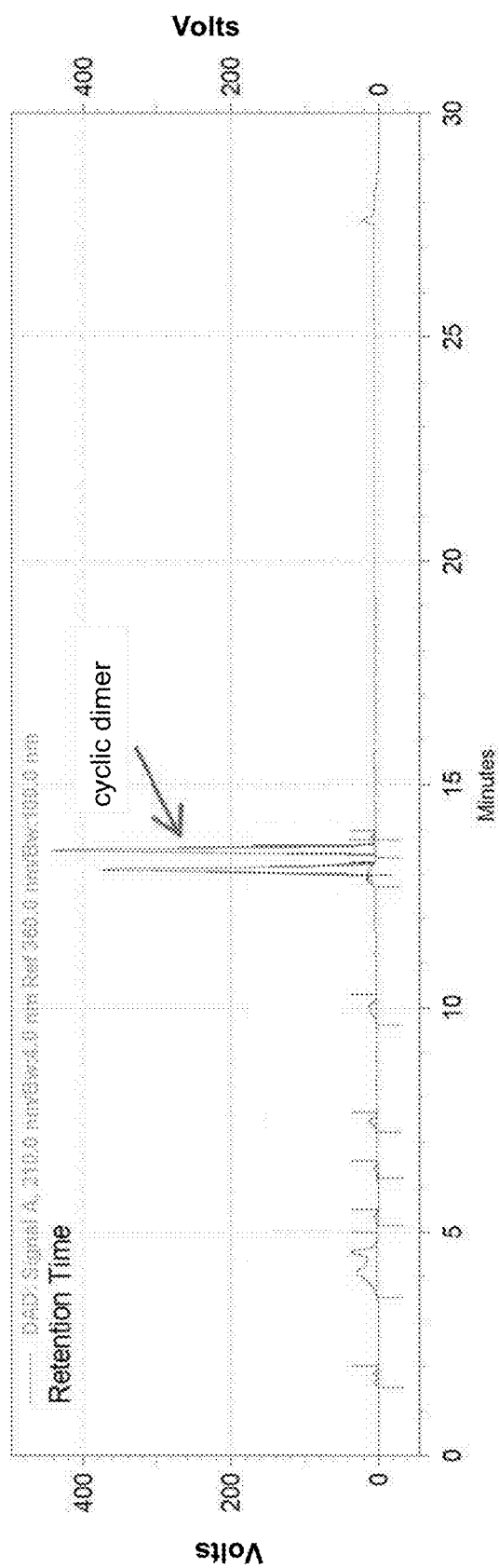
FIG. 8 presents an HPLC chromatogram of distillates of the depolymerization reaction of polymer formed from HMTBa.

To a flask was added 4.0 g of oligomers of HMTBa (Mn=1.0×10³ g/mol) made by polycondensation and the oligomers were dried in a vacuum at 60° C. overnight. The oligomers were heated (further polymerized) at 140° C. for 1 hour. After that, the flask was cooled down and about 15 mg of tin catalyst was added. The flask was transferred to Kugelrohr for depolymerization of the oligomer at 200° C. for 2 hours and under a vacuum (500 mTorr~1 Torr). The distillates were collected. Both of the distillates and the mixture in the flask were analyzed by HPLC and GPC. The distillates had cyclic dimers with 90.7% purity by HPLC, yield 0.62 grams. The cyclic dimer concentration in the reaction mixture was 4.3%. An estimation of cyclic dimer yield in this reaction was 18%. An HPLC spectrum of the distillates is shown in FIG. 8.

What is claimed is:

1. A composition comprising a polymer comprising a repeat unit of Formula (XX):

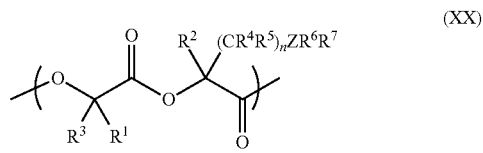

wherein:
R¹, R², R³, R⁴, and R⁵ are independently hydrogen, hydrocarbyl, or substituted hydrocarbyl;
R⁶ is hydrocarbyl or substituted hydrocarbyl;
R⁷ is not present;
Z is sulfur, sulfone, sulfoxide, or selenium;
n is an integer from 1 to 20; and
the composition polymer contains less than about 5% by weight of a monomer.

2. The composition polymer of claim 1, wherein R¹, R², R³, R⁴, and R⁵ are hydrogen; n is from 1 to 10; and R⁶ is C₁-C₆ alkyl.

3. A composition comprising a polymer comprising a repeat unit of Formula (XXa):

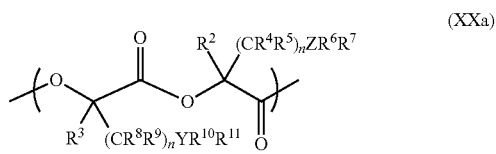

wherein:
R², R³, R⁴, R⁵, R⁸, and R⁹ are independently hydrogen, hydrocarbyl, or substituted hydrocarbyl;
R⁶ and R¹⁰ are independently hydrocarbyl or substituted hydrocarbyl;
R⁷ and R¹¹ are not present;
Y and Z are independently sulfur, sulfone, sulfoxide, or selenium; and
n and m are integers from 1 to 20.

4. The composition of claim 3, wherein R², R³, R⁴, R⁵, R⁸ and R⁹ are hydrogen; each of n and m is from 1 to 10; and R⁶ and R¹⁰ are C₁-C₆ alkyl.

5. The composition of claim 1, wherein the repeat unit comprises Formula (XXV):

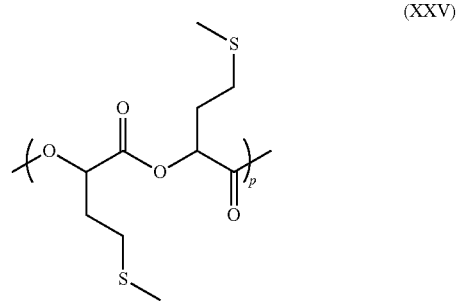

wherein:
p is an integer greater than 1;
provided that when p is less than 4, then the polymer has a polydispersity index of less than about 1.3.

6. The composition of claim 1, wherein the composition contains less than about 3% by weight of the monomer.

7. The composition of claim 1, wherein the polymer has a number average molecular weight of at least about 2000 Da, at least about 10,000 Da, at least about 100,000 Da, or at least about 1,000,000 Da.

8. The composition of claim 1, wherein the polymer hydrolyzes in an aqueous solution at a pH below about 5.0.

9. The composition of claim 1, wherein each repeat unit of the polymer has a configuration chosen from RR, RS, SR, and SS.

10. The composition of claim 1, further comprising a nutritive or pharmaceutical agent.

11. The composition of claim 1, further comprising at least one additional polymer.

12. The composition of claim 1, wherein the polymer comprises a first repeat unit comprising Formula (XX) and a second repeat unit.

13. The composition of claim 12, wherein the second repeat unit comprises Formula (XX), provided the second repeat unit is substituted differently in at least one position than the first repeat unit comprising Formula (XX).

14. The composition of claim 12, wherein the second repeat unit is derived from a lactide, a lactone, a lactam, an hydroxyl alkanoate, or an hydroxyl ester.

15. A process for forming a polymer comprising repeat units of Formula (XX), the process comprising contacting a plurality of compounds of Formula (II):

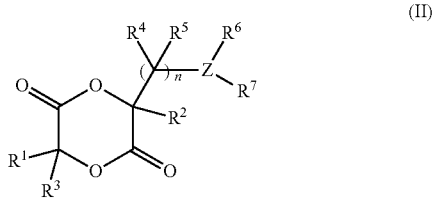

(II)

with a catalyst to form the polymer comprising repeat units of Formula (XX):

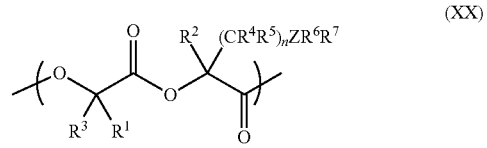

(XX)

wherein:
$R^1$ is $(CR^8R)_m YR^{10}R^{11}$;
$R^2$, $R^3$, $R^4$, $R^5$, $R^8$, and $R^9$ are independently hydrogen or alkyl;
$R^6$ and $R^{10}$ are alkyl;
$R^7$ and $R^{11}$ are not present;
Z and Y are independently sulfur, sulfone, sulfoxide, or selenium; and
n and m are integers from 1 to 20.

16. The process of claim 15, wherein the compounds of Formula (II) have Formula (V) and the repeat units of Formula (XX) have-Formula (XXV):

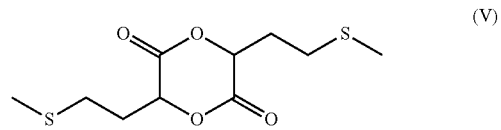

(V)

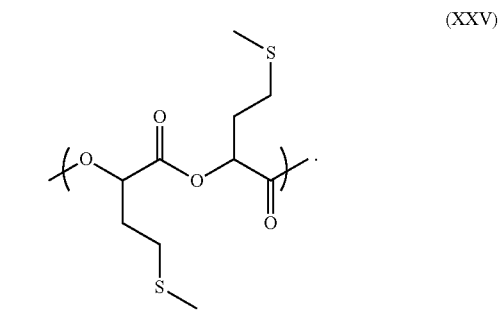

(XXV)

17. The process of claim 15, wherein the catalyst is tin(II) octanoate, aluminum(III) isopropoxide, zinc(II) lactate, an yttrium complex, a bis- or trisaryl tin complex, a heterobimetallic iron(II) complex, a titanium complex with bridged-biphenolate ligand, a cationic aluminum complex, or a pyridine catalyst; and the reaction is conducted at a temperature from about 100° C. to about 200° C. under an inert atmosphere.

18. The process of claim 15, wherein the reaction is conducted in the presence of a ring opening initiator, the ring opening initiator being a small molecule or a polymer comprising at least one hydroxyl group and/or an amine group.

19. The process of claim 18, wherein the ring opening initiator is water, an alcohol, a polyol, a polyalkylene oxide, a glycol, a polyglycol, or a low molecular weight primary or secondary amine.

20. The process of claim 15, wherein the reaction is conducted in the presence of a solvent; or the reaction is conducted in the absence of a solvent.

21. The process of claim 15, wherein the polymer comprising repeat units of Formula (XX) has a number average molecular weight of at least about 2,000 Da, at least about 10,000 Da, at least about 100,000 Da, or at least about 1,000,000 Da.

22. The process of claim 15, wherein the catalyst is tin(II) octanoate and the reaction is conducted at a temperature from about 120° C. to about 180° C. under an inert atmosphere.

23. The process of claim 22, wherein the reaction further comprise an alcohol as a ring opening initiator.

24. The process of claim 15, wherein the process further comprises contact with a plurality of additional monomers to form a copolymer comprising first repeat units of Formula (XX) and second repeat units derived from the additional monomers.

25. The process of claim 24, wherein the plurality of additional monomers is chosen from acrylates, aminoacrylates, alkylene succinates, alkylene oxalates, amides, amino acids, anhydrides, arylates, carbonates, cellulose, caprolactone, caprolactam, cyanoacrylates, cyclic ethers, dihydropyrans, dioxanes, dioxanones, ether ether ketones, ethylene glycol, fumarates, hydroxy alkanoates, hydroxy esters, imides, ketals, lactides, lactones, lactams, methacrylates, methyl olefins, orthoesters, phosphazines, styrenes, terephthalates, tetrafurans, trimethylene carbonate, urethanes, vinyl acetates, vinyl ketones, or vinyl halides.

26. The process of claim 25, wherein the additional monomers are lactides, lactones, lactams, hydroxy alkanoates, or hydroxy esters.

27. The process of claim 24, wherein the catalyst is tin(II) octanoate, aluminum(III) isopropoxide, zinc(II) lactate, an yttrium complex, a bis- or trisaryl tin complex, a heterobimetallic iron(II) complex, a titanium complex with bridged-biphenolate ligand, a cationic aluminum complex, or a pyridine catalyst; and the reaction is conducted at a temperature from about 100° C. to about 200° C. under an inert atmosphere.

28. The process of claim 24, wherein the reaction is conducted in the presence of a ring opening initiator chosen from water, an alcohol, a polyol, a polyalkylene oxide, a glycol, a polyglycol, or a low molecular weight primary or secondary amine.

29. The process of claim 24, wherein the reaction is conducted in the presence of a solvent; or the reaction is conducted in the absence of a solvent.

30. The process of claim 24, wherein the catalyst is tin(II) octanoate and the reaction is conducted at a temperature from about 120° C. to about 180° C. under an inert atmosphere.

31. The process of claim 30, wherein the reaction further comprises an alcohol as a ring opening initiator.

* * * * *